(12) United States Patent
Wang et al.

(10) Patent No.: US 11,007,281 B2
(45) Date of Patent: May 18, 2021

(54) NANO/MICROMOTORS FOR ACTIVE AND DYNAMIC INTRACELLULAR PAYLOAD DELIVERY

(71) Applicant: The regents of the University of California, Oakland, CA (US)

(72) Inventors: Joseph Wang, San Diego, CA (US); Berta Esteban-Fernández de Ávila, San Diego, CA (US); Yi Chen, La Jolla, CA (US); Chava Angell, La Jolla, CA (US); Fernando Soto, La Jolla, CA (US); Liangfang Zhang, San Diego, CA (US); Malthe Hansen-Bruhn, Aarhus (DK)

(73) Assignee: THE REGENTS OF THE UNIVERSITY OF CALIFORNA, Oakland, CA (US)

( * ) Notice: Subject to any disclaimer, the term of this patent is extended or adjusted under 35 U.S.C. 154(b) by 410 days.

(21) Appl. No.: 15/939,104

(22) Filed: Mar. 28, 2018

(65) Prior Publication Data

US 2019/0070314 A1  Mar. 7, 2019

Related U.S. Application Data

(60) Provisional application No. 62/477,877, filed on Mar. 28, 2017.

(51) Int. Cl.
| | |
|---|---|
| A61K 48/00 | (2006.01) |
| A61K 38/48 | (2006.01) |
| A61K 41/00 | (2020.01) |
| A61M 31/00 | (2006.01) |
| A61M 37/00 | (2006.01) |
| C12N 15/11 | (2006.01) |
| C12N 15/113 | (2010.01) |
| C12N 9/22 | (2006.01) |
| C12N 9/64 | (2006.01) |
| C12N 15/87 | (2006.01) |
| B82Y 15/00 | (2011.01) |

(52) U.S. Cl.
CPC ...... *A61K 48/0083* (2013.01); *A61K 38/4873* (2013.01); *A61K 41/0028* (2013.01); *A61M 31/002* (2013.01); *A61M 37/0092* (2013.01); *C12N 9/22* (2013.01); *C12N 9/6472* (2013.01); *C12N 15/11* (2013.01); *C12N 15/111* (2013.01); *C12N 15/113* (2013.01); *C12N 15/87* (2013.01); *C12Y 304/22056* (2013.01); *A61M 2037/0007* (2013.01); *B82Y 15/00* (2013.01); *C12N 2310/14* (2013.01); *C12N 2310/20* (2017.05); *C12N 2320/32* (2013.01)

(58) Field of Classification Search
None
See application file for complete search history.

(56) References Cited

U.S. PATENT DOCUMENTS

| | | | |
|---|---|---|---|
| 9,352,963 B2 | 5/2016 | Wang et al. | |
| 9,698,708 B2* | 7/2017 | Wang | H01L 29/872 |
| 9,726,114 B2* | 8/2017 | Wang | F03G 7/005 |
| 9,868,991 B2* | 1/2018 | Wang | C12Q 1/6816 |
| 9,879,310 B2* | 1/2018 | Wang | G01N 33/54313 |
| 2013/0084569 A1 | 4/2013 | Wang et al. | |
| 2013/0241344 A1 | 9/2013 | Wang | |
| 2014/0045179 A1 | 2/2014 | Wang et al. | |
| 2015/0013304 A1 | 1/2015 | Wang et al. | |

OTHER PUBLICATIONS

De Avila, et al. (Jun. 2, 2015) "Single Cell Real-Time miRNAs Sensing Based on Nanomotors", ACS Nano, 9(7): 6756-54. (Year: 2015).*
Xu, et al. (2015) "Reversible Swarming and Separation of Self-Propelled Chemically Powered Nanomotors under Acoustic Fields", Journal of the American Chemical Society, 137: 2163-66. (Year: 2015).*
Aliabadi, et al. (2011) "Induction of Apoptosis by Survivin Silencing through siRNA Delivery in a Human Breast Cancer Cell Line", Molecular Pharmaceutics, 8: 1821-30. (Year: 2015).*
Esteban-Fernandez, et al. (2017) "Nanomotor-Enabled pH-Responsive Intracellular Delivery of Caspase-3: Toward Rapid Cell Apoptosis", ACS Nano, 11: 5367-74. (Year: 2017).*
Sattayasamitsathit, et al. (2014) "Fully Loaded Micromotors for Combinatorial Delivery and Autonomous Release of Cargoes", Small, 10(14): 2830-2833 (Year: 2014).*
Tu, et al. (2017) "Biodegradable Hybrid Stomatocyte Nanomotors for Drug Delivery", ACS Nano, 11: 1957-1963 (Year: 2017).*
Kuralay et al., Self-Propelled Carbohydrate-Sensitive Microtransporters with Built-In Boronic Acid Recognition for Isolating Sugars and Cells, J. Am. Chem. Soc. 2012, 134, 15217-15220.
Lee et al., Synthetically modified guide RNA and donor DNA are a versatile platform for CRISPR-Cas9 engineering, eLife 2017, 6, e25312.
Lee et al.,Gold, Poly(β-amino ester) Nanoparticles for Small Interfering RNA Delivery. Nano Lett. 2009, 9, 2402-2406.

(Continued)

*Primary Examiner* — Robert M Kelly
(74) *Attorney, Agent, or Firm* — Perkins Coie LLP

(57) ABSTRACT

Methods, systems, and devices are disclosed for intracellular payload delivery by nanomotor structures. In some aspects, a nanomotor for intracellular payload delivery includes an asymmetric body having a concave cavity at one end of the nanowire body; a functionalization layer on an outer surface of the nanowire body; and a payload substance coupled to the nanomotor by the functionalization layer in a biologically active conformation, wherein the payload substance is attached to a portion of the functionalization layer or at least partially encapsulated within the functionalization layer, in which the nanomotor is operable to propel in a biological medium and into an intracellular region of a living cell to initiate an interaction of the biologically active payload substance with an intracellular constituent of the living cell.

7 Claims, 30 Drawing Sheets

Specification includes a Sequence Listing.

(56) References Cited

OTHER PUBLICATIONS

Lee et al,. Molecularly Self-Assembled Nucleic Acid Nanoparticles for Targeted in Vivo siRNA Delivery. Nat. Nanotechnol. 2012, 7, 389-393.
Lee et al,. Target-Specific Gene Silencing of Layer-by-Layer Assembled Gold-Cysteamine/siRNA/PEI/HA Nanocomplex. ACS Nano 2011, 5, 6138-6147.
Li et al,. Micro/nanorobots for biomedicine: delivery, surgery, sensing, and detoxification, Science Robotics Mar. 1, 2017: vol. 2, Issue 4, eaam6431, DOI: 10.1126/scirobotics.aam6431.
Li et al., Rocket science at the nanoscale, ACS Nano 2016, 10, 5619-5634.
Li et al., Water-driven micromotors for rapid photocatalytic degradation of biological and chemical warfare agents, ACS Nano 2014, 8, 11118-11125.
Li et al., Enteric micromotor can selectively position and spontaneously propel in the gastrointestinal tract, ACS Nano 2016, 10, 9536-9542.
Li et al., Micromotors spontaneously neutralize gastric acid for pH-responsive payload release, Angew. Chem. Int. Ed. 2017, 56, 2156-2161.
Liang et al., Rapid and highly efficient mammalian cell engineering via Cas9 protein transfection, Biotechnol. 2015, 208, 44-53.
Lin et al,. Rolling-Circle Amplification of a DNA Nanojunction. Angew. Chem., Int. Ed. 2006, 45, 7537-7539.
Lytton-Jean et al., Five Years of siRNA Delivery: Spotlight on Gold Nanoparticles. Small 2011, 7, 1932-1937.
Ma et al., Enzyme-powered hollow mesoporous Janus nanomotors, Nano Lett. 2015, 15, 7043-7050.
Ma et al., Motion control of urea-powered biocompatible hollow microcapsules, ACS Nano 2016, 10, 3597-3605.
Mali et al., RNA-Guided Human Genome Engineering via Cas9, Science 2013, 339, 823-826.
Magdanz et al., Development of sperm-flagella driven micro-biorobot, Adv. Mat. 2013, 25, 6581-6588.
McClellan et al., Genetic Heterogeneity in Human Disease. Cell 2010, 141, 210-217.
Medina-Sanchez et al., Cellular Cargo Delivery: Toward assisted fertilization by sperm-carrying micromotors, Nano Lett., 2016, 16, 555-561.
Mhanna et al., Artificial bacterial flagella for remote-controlled targeted single-cell drug delivery, Small 2014, 10, 1953-1957.
Miao et al., Ultrasensitive Detection of MicroRNA through Rolling Circle Amplification on a DNA Tetrahedron Decorated Electrode. Bioconjugate Chem. 2015, 26,602-607.
Modi et al., A DNA Nanomachine that Maps Spatial and Temporal pH Changes inside Living Cells. Nat. Nanotechnol. 2009, 4, 325-330.
Moreno-Guzman et al., Self-propelled enzyme-based motors for smart mobile electrochemical and optical biosensing, Anal. Chem. 2015, 87, 12380-12386.
Mou et al,. Single-component TiO2 tubular microengines with motion controlled by light-induced bubbles, Small 2015, 11, 2564-2570.
Mou et al., Self-propelled micromotors driven by the magnesium-water reaction and their hemolytic properties. Angew. Chem. Int. Ed. 2013, 52, 7208-7212.
Mout et al., Direct Cytosolic Delivery of CRISPR/Cas9-Ribonucleoprotein for Efficient Gene Editing, ACS Nano. 2017, 11, 2452-2458.
Nadal et al., Asymmetric Steady Streaming as a Mechanism for Acoustic Propulsion of Rigid Bodies. Phys. Fluids 2014, 26, 082001-082028.
Peng et al., Self-guided supramolecular cargo-loaded nanomotors with chemotactic behavior towards cells, Angew. Chem. Int. Ed. 2015, 54, 11662-11665.
Peng et al. Micro-nanomotors towards in vivo application: cell, tissue and biofluid, Chem. Soc. Rev. 2017, 46, 5289-5310.
Qiu et al., Magnetic helical microswimmers functionalized with lipoplexes for targeted gene delivery, Adv. Funct. Mater. 2015, 25, 1666-1671.
Qiu et al., Artificial bacterial flagella functionalized with temperature-sensitive liposomes for controlled release, Sens. Actuator B-Chem. 2014, 196, 676-681.
Rao et al., A Force to be reckoned with: a review of synthetic microswimmers powered by ultrasound, Small 2015, 11, 2836-2846.
Sanchez et al., Chemically powered micro- and nanomotors, Angew. Chem. Int. Ed. 2014, 53, 2-33.
Sanchez et al., Chemically Powered Micro- and Nanomotors. Angew. Chem., Int. Ed. 2015, 54, 1414-1444.
Sander et al., CRISPR-Cas systems for editing, regulating and targeting genomes, Nat. Biotechnol. 2014, 32, 347-355.
Sattayasamitsathit et al., Fully loaded micromotors for combinatorial delivery and autonomous release of cargoes, Small 2014, 10, 2830-2833.
Semple et al., Rational Design of Cationic Lipids for siRNA Delivery. Nat. Biotechnol. 2010, 28, 172-176.
Sengupta et al., Self-powered enzyme micropumps, Nat. Chem. 2014, 6, 415-422.
Shalem et al., High-throughput functional genomics using CRISPR-Cas9, Nat. Rev. Genet. 2015, 16, 299-311.
Sokolov et al., Smart materials on the way to theranostic nanorobots: Molecular machines and nanomotors, advanced biosensors, and intelligent vehicles for drug delivery, Biochim. Biophys. Acta 2017, pp. 1530-1544.
Solovev et al., Catalytic microtubular jet engines self-propelled by accumulated gas bubbles. Small 2009, 5, 1688-1692.
Soto et al., Acoustic microcannons: toward advanced microballistics, ACS Nano 2016, 10, 1522-1528.
Soto et al. Acoustically propelled nanoshells, Nanoscale 2016, 8, 17788-17793.
Srivastava et al., Medibots: dual-action biogenic microdaggers for single-cell surgery and drug release, Adv. Mater. 2016, 28, 832-837.
Stanton et al., Magnetatactic Bacteria Powered Biohybrids Target *E. coli* Biofilms, ACS Nano 2017, 11, 9968-9978.
Sun et al., Self-Assembled DNA Nanoclews for the Efficient Delivery of CRISPR-Cas9 for Genome Editing, Angew. Chem. Int. Ed. Engl. 2015, 54, 12029-12033.
Thomas et al,. HEK293 Cell Line: A Vehicle for the Expression of Recombinant Proteins. J. Pharmacol. Toxicol. Methods 2005, 51, 187-200.
Tsai et al., Defining and improving the genome-wide specificities of CRISPR-Cas9 nucleases, Nat. Rev. Genet. 2016, 17, 300-312.
Tu et al., Biodegradable hybrid stomatocyte nanomotors for drug delivery, ACS Nano 2017, 11, 1957-1963.
Tu et al., Redox-Sensitive Stomatocyte Nanomotors: Destruction and Drug Release in the Presence of Glutathione, Angew. Chem. Int. Ed. Engl. 2017, 56, 7620-7624.
Agrawal et al., RNA Interference: Biology, Mechanism, and Applications. Microbiol Mol. Biol. Rev. 2003, 67, 657-685.
Ahmed et al., "Steering Acoustically Propelled Nanowire Motors toweard Cells in a Biologically Compatible Environment Using Magnetic Fields", Langmuir 2013, 29, 16113-16118.
Angell et al., DNA Nanotechnology for Precise Control over Drug Delivery and Gene Therapy. Small 2016, 12, 1117-1132.
Balasubramanian et al., Micromachine-enabled capture and isolation of cancer cells in complex media, Angew. Chem. Int. Ed. 2011, 50, 4161-4164.
Campuzano et al., Bacterial isolation by lectin-modified microengines, Nano Lett. 2012, 12, 396-401.
Campuzano et al., Motion-driven sensing and biosensing using electrochemically propelled nanomotors, Analyst 2011, 136, 4621-4630.
Campuzano et al., "Nano-microvehicles for efficient delivery and (bio) sensing at the cellular level", Chem. Sci. 2017, 8, 6750-6763.
Castanotto et al., The Promises and Pitfalls of RNA-Interference-Based Therapeutics. Nature 2009, 457, 426-33.
Chalupniak et al., Micro and nanomotors in diagnostics, Adv. Drug Deliv. Rev. 2015, 95, 104-116.

(56) References Cited

OTHER PUBLICATIONS

Chen et al., Hybrid magnetoelectric nanowires for nanorobotic applications: fabrication, magnetoelectric coupling, and magnetically assisted in vitro targeted drug delivery, Adv. Mater. 2017, 29, 1605458.
Chen et al., Transient micromotors that disappear when no longer needed, ACS Nano 2016, 10, 10389-10396.
Cheng et al,. Acceleration of Tissue Plasminogen Activator-Mediated Thrombolysis by Magnetically Powered Nanomotors. ACS Nano 2014, 8, 7746-7754.
Chng et al., Towards biocompatible nano/microscale machines: self-propelled catalytic nanomotors not exhibiting acute toxicity. Nanoscale 2014, 6, 2119-2124.
Chu et al., Increasing the efficiency of homology-directed repair for CRISPR-Cas9-induced precise gene editing in mammalian cells, Nat Biotechnol. 2015, 33, 543-548.
Davis et al., Nanoparticle therapeutics: an emerging treatment modality for cancer, Nat. Rev. Drug Discov. 2008, 7, 771-782.
Ding et al., Enhanced efficiency of human pluripotent stem cell genome editing through replacing TALENs with CRISPRs, Cell Stem Cell 2013, 12, 393-394.
Esteban-Fernandez et al., Acoustically propelled nanomotors for intracellular siRNA delivery, ACS Nano 2016, 10, 4997-5005.
Esteben-Fernandez et al., Nanomotor-enabled pH-responsive intracellular delivery of caspase-3: towards rapid cell apoptosis, ACS Nano 2017, 11, pp. 5367-5374.
Esteban-Fernandez et al., Single cell real-time miRNAs sensing based on nanomotors, ACS Nano 2015, 9, 6756-6764.
Esteban-Fernandez et al., Micromotor-enabled active drug delivery for in vivo treatment of stomach infection, Nat. Comm. 2017, 8:272.
Fan et al., Subcellular-resolution delivery of a cytokine through precisely manipulated nanowires, Nat. Nanotechnol. 2010, 5, 545-551.
Felfoul et al., Magneto-aerotactic bacteria deliver drug-containing nanoliposomes to tumour hypoxic regions, Nat. Nanotechnol. 2016, 11, 941-947.
Fu et al., Impriving CRISPR-Cas nuclease specificity using truncated guide RNAs, Nat. Biotechnol. 2014, 32, 279-284.
Gao et al., Synthetic micro/nanomotors in drug delivery, Nanoscale 2015, 6, 10486-10494.
Gao et al., Seawater-driven magnesium based Janus micromotors for environmental remediation, Nanoscale 2013, 5, 4696-4700.
Gao et al., Water-driven micromotors, ACS Nano 2012, 6, 8432-8438.
Gao et al., Highly efficient catalytic microengines: template electrosynthesis of polyaniline/platinum microtubes, J. Am. Chem. Soc. 2011, 133, 11862-11864.
Gao et al., Artificial micromotors in the mouse's stomach: a step toward in vivo use of synthetic motors, ACS Nano 2015, 9, 117-123.
Gao et al., Cargo-towing fuel-free magnetic nanoswimmers for targeted drug delivery, Small 2012, 8, 460-467.
Garcia-Gradilla et al,. Functionalized Ultrasound-Propelled Magnetically Guided Nano-motors: Toward Practical Biomedical Applications. ACS Nano 2013, 7, 9232-9240.
Garcia-Gradilla et al., Ultrasound-propelled nanoporous gold wire for efficient drug loading and release, Small 2014, 10, 4154-4159.
Ghosh et al., Controlled propulsion of artificial magnetic nanostructured propellers, Nano Lett. 2009, 9, 2243-2245.
Gilleron et al., Image-based analysis of lipid nanoparticle-mediated siRNA delivery, intracellular trafficking and endosomal escape. Nat. Biotechnol. 2013, 31, 638-646.
Guo et al., Enhanced Gene Delivery and siRNA Silencing by Gold Nanoparticles Coated with Charge-Reversal Polyelectrolyte. ACS Nano 2010, 4, 5505-5511.
Guix et al., Carbonate-based Janus micromotors moving in ultralight acidic environment generated by HeLa cells in situ, Sci. Rep. | 6:21701 | DOI: 10.1038/srep21701.
Guix et al., Nano/micromotors in (bio)chemical science applications, Chem. Rev. 2014, 114, 6285-6322.

Hansen-Bruhn et al. "Active Intracellular Delivery of a Cas9/sgRNA Complex Using Ultrasound-Propelled Nanomotors", Agnew. Chem. Int. Ed. 2018, 57, pp. 2657-2661.
Harris et al., Glutathione and Thioredoxin Antioxidant Pathways Synergize to Drive Cancer Inititation and Progression, Cancer Cell 2015, 27, 211-222.
Hong et al., Gene Silencing by siRNA Microhydrogels via Polymeric Nanoscale Condensation. J. Am. Chem. Soc. 2011, 133, 13914-13917.
Hoop et al., A smart multifunctional drug delivery nanoplatform for targeting cancer cells, Nanoscale 2016, 8, 12723-12728.
Hsu et al., Development and Applications of CRISPR-Cas9 for Genome engineering, Cell 2014, 157, 1262-1278.
Jang et al., Design of a Platform Technology for Systemic Delivery of siRNA to Tumours Using Rolling Circle Transcription. Nat. Commun. 2015, 6, 7930.
Jensen et al., Spherical Nucleic Acid Nanoparticle Conjugates as an RNAi-Based Therapy for Glioblastoma. Sci. Transl. Med. 2013, 5, 209ra152.
Kagan et al., Functionalized micromachines for selective and rapid isolation of nucleic acid targets from complex samples, Nano Lett. 2011, 11, 2083-2087.
Kagan et al., Acoustic droplet vaporization and propulsion of perfluorocarbon-loaded microbullets for targeted tissue penetration and deformation, Angew. Chem. Int. Ed. 2012, 124, 7637-7640.
Kagan et al., Rapid delivery of drug carriers propelled and navigated by catalytic nanoshuttles, Small 2010, 6, 2741-2747.
Kim et al., Highly efficient RNA-guided genome editing in human cells via delivery of purified Cas9 ribonucleoproteins, Genome Res. 2014, 24, 1012-1019.
Kim et al., Drug Delivery by a Self-Assembled DNA Tetrahedron for Overcoming Drug Resistance in Breast Cancer Cells. Chem. Commun. 2013, 49, 2010-2012.
Kim et al., Recent Progress on Man-Made Inorganic Nanomachines. Small 2015, 11, 4037-4057.
Kiristi ert al., Lysozyme-Based Antibacterial Nanomotors. ACS Nano 2015, 9, 9252-9259.
Varkouhi et al., Endosomal escape pathways for delivery of biologicals. J. Controlled Release 2011, 151, 220-228.
Wang et al., Fabrication of Micro/Nanoscale Motors. Chem. Rev. 2015, 115, 8704-8735.
Wang et al., Small Power: Autonomous Nano- and Micromotors Propelled by Self-Generated Gradients. Nano Today 2013, 8, 531-554.
Wang et al., Nano/Microscale motors: biomedical opportunities and challenges, ACS Nano, 2012, 6, 5745-5751.
Wang et al., Motion control at the nanoscale, Small, 2010, 6, 338-345.
Wang et al., Acoustic propulsion of nanorod motors inside living cells, Angew. Chem. Int. Ed. 2014, 126, 3265-3268.
Wang, Self-propelled affinity biosensors: Moving the receptor around the sample, Biosens. Bioelectron. 2016, 76, 234-242.
Wang et al., Bioinspired Spiky Micromotors Based on Sporopollenin Exine Capsules, Adv. Funct. Mater. 2017, 27, 1702338.
Wang et al., Acoustic Propulsion of Nanorod Motors Inside Living Cells, Angew. Chem. Int. Ed. 2014, 53, 3201-3204.
Wu et al., Self-propelled polymer-based multilayer nanorockets for transportation and drug release, Angew. Chem. Int. Ed. 2013, 52, 7000-7003.
Wu et al., Self-propelled polymer multilayer Janus capsules for effective drug delivery and light-triggered release, ACS Appl. Mater. Interfaces 2014, 6, 10476-10481.
Wu et al., Biodegradable protein-based rockets for drug transportation and light-triggered release, ACS Appl. Mater. Interfaces 2015, 7, 250-255.
Wu et al., Water-powered cell-mimicking Janus micromotor, Adv. Funct. Mater. 2015, 25, 7497-7501.
Wu et al., Motion-based DNA detection using catalytic nanomotors, Nat. Comm. 2010, 1:36.
Wu et al., Cell-Membrane-Coated Synthetic Nanomotors for Effective Biodetoxification. Adv. Funct. Mater. 2015, 25, 3881-3887.
Xu et al., Fuel-free synthetic micro-/nanomachines, Adv. Mater. 2017, 1603250, DOI: 10.1002/adma.201603250.

(56) References Cited

OTHER PUBLICATIONS

Xu et al., Sperm-hybrid micromotor for drug delivery in the female reproductive tract. Physics > Medical Physics, arXiv:1703.08510.
Xu et al., Glutathione- and pH-responsive nonporous silica prodrug nanoparticles for controlled release and cancer therapy, Nanoscale 2015, 7, 5859-5868.
Xuan et al,. Self-propelled Janus mesoporous silica nanomotors with sub-100 nm diameters for drug encapsulation and delivery, ChemPhysChem 2014, 15, 2255-2260.
Xuan et al., Near Infrared Light-Poweed Janus Mesoporous Silica Nanoparticle Motors, J. Am. Chem. Soc. 2016, 138, 6492-6497.
Yan et al., Growth and Origami Folding of DNA on Nanoparticles for High-Efficiency Molecular Transport in Cellular Imaging and Drug Delivery. Angew. Chem., Int. Ed. 2015, 54, 2431-2435.
Yan et al., Multifunctional biohybrid magnetite microrobots for imaging-guided therapy, Sci. Robot. 2017, 2, 14 pages.
Yu et al., Improved delivery of Cas9 protein/gRNA complexes using lipofectamine CRISPRMAX, Biotechnol. Lett. 2016, 38, 919-929.
Zhang et al., Self-powered glucose-responsive micropumps, ACS Nano 2014, 8, 8537-8542.
Zhao et al., DNA Origami Delivery System for Cancer Therapy with Tunable Release Properties. ACS Nano 2012, 6, 8684-8691.
Zhu et al., Self-Assembled, Aptamer-Tethered DNA Nanotrains for Targeted Transport of Molecular Drugs in Cancer Theranostics. Proc. Natl. Acad. Sci. U. S. A. 2013, 110, 7998-8003.
Zuris et al., Cationic lipid-mediated delivery of proteins enables efficient protein-based genome editing in vitro and in vivo, Nat Biotechnol. 2015, 33, 73-80.

* cited by examiner

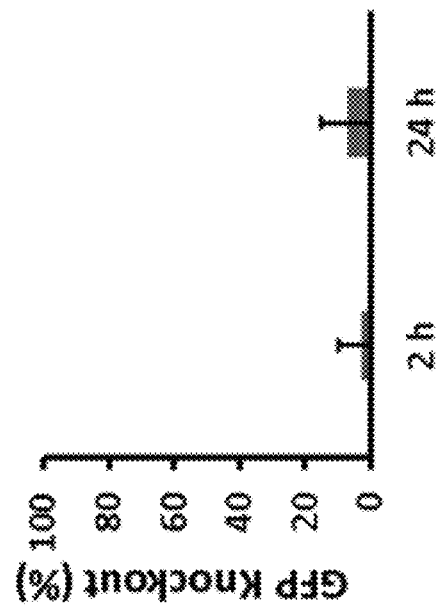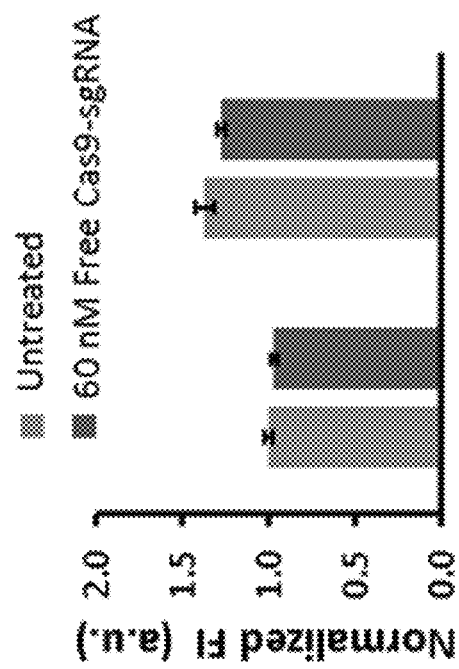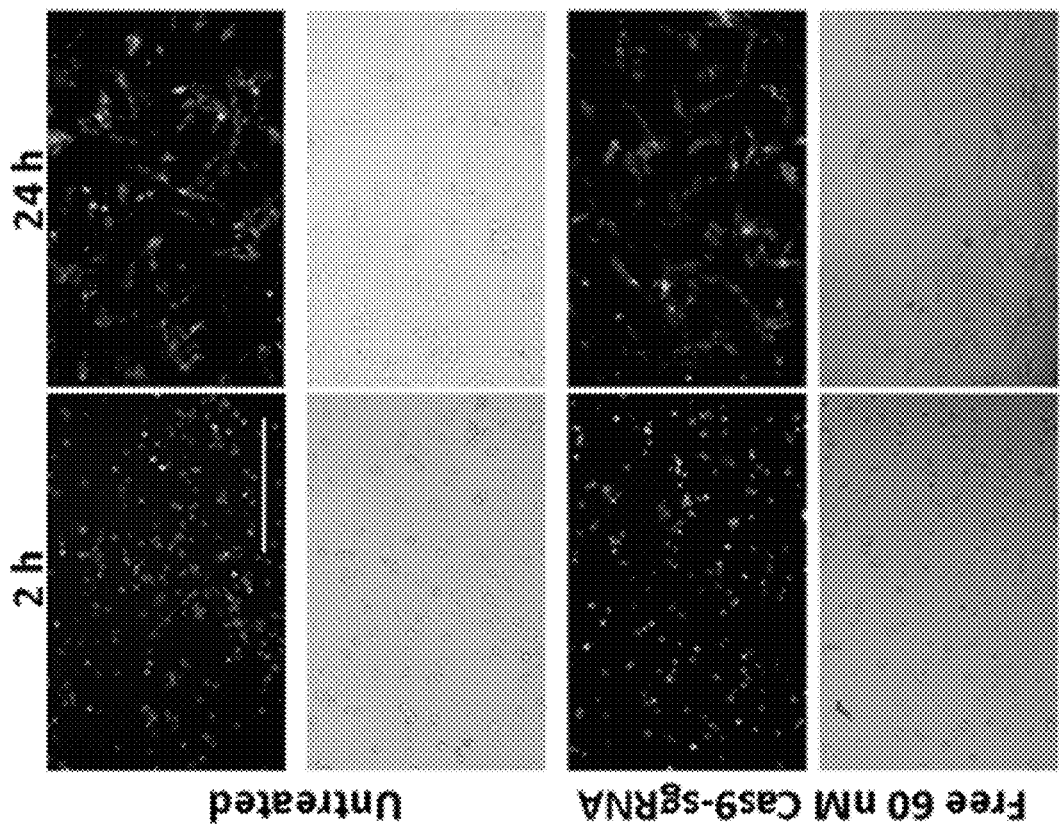
FIG. 11B
FIG. 11C
FIG. 11A

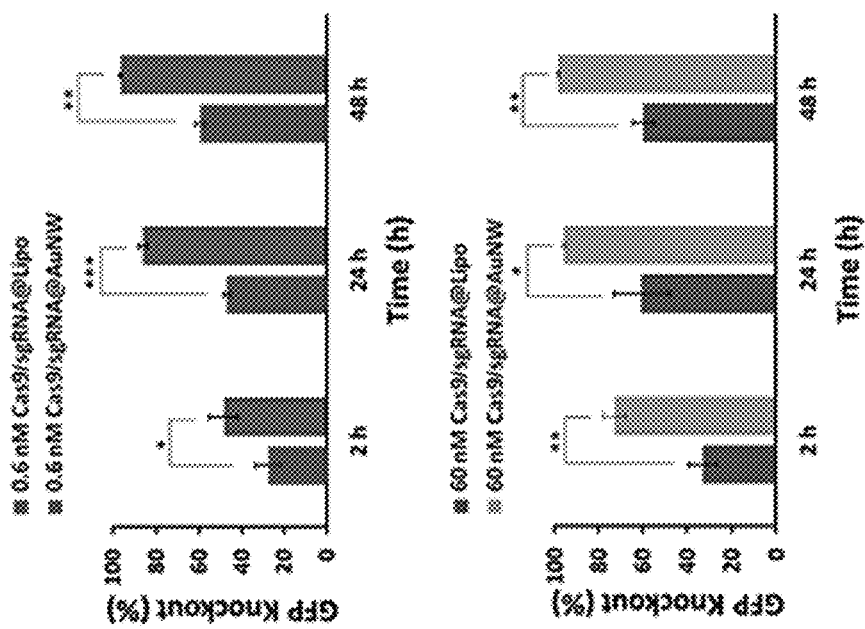
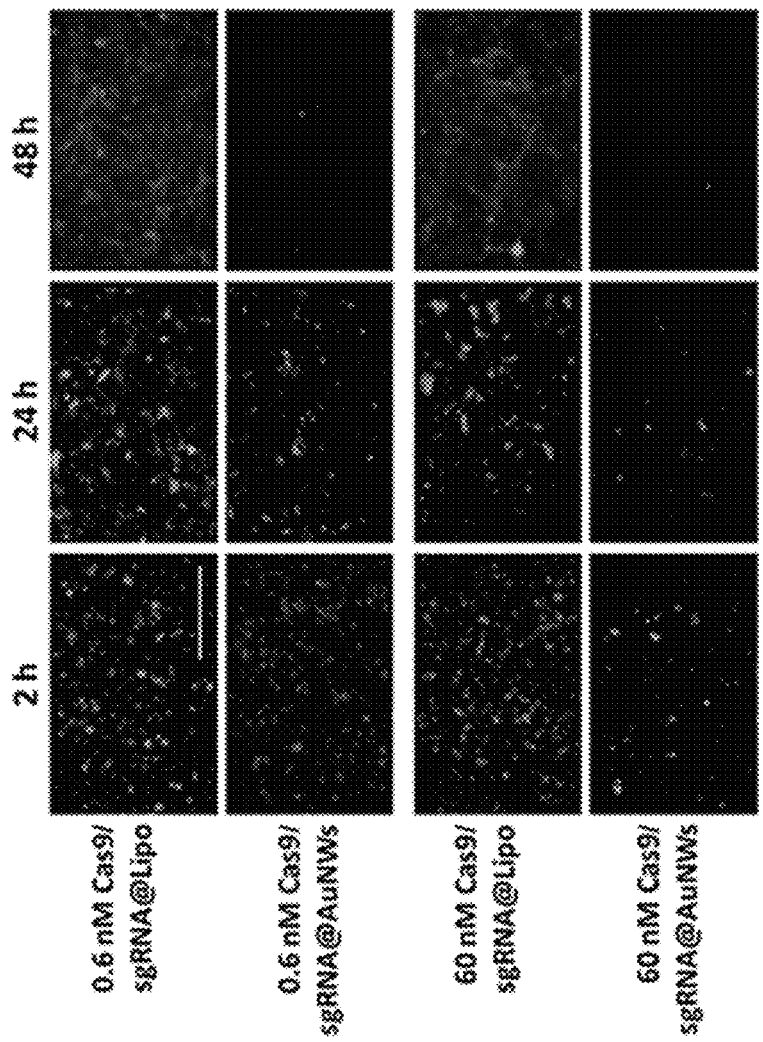
FIG. 15B
FIG. 15A

```
                       SEQUENCE LISTING

<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atacatacat aaaaaaaaaa aaaaaaaaaa a                                          31

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tatgtatttt tttt                                                            14

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
acaugaagca gcacgacuut taaaaaaaaa aaaaaaaaaa a                               41

<210> SEQ ID NO 4
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
aagucgugcu gcuucaugut t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
cuuacgcuga guacuucgat t                                             21

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
ucgaaguacu cagcguaagt taaaaaaaaa aaaaaaaaaa a                       41

<210> SEQ ID NO 7
<211> LENGTH: 20
<212> TYPE: DNA
<213> ORGANISM: Aequorea victoria

<400> SEQUENCE: 7
gggcacgggc agcttgccgg                                               20

<210> SEQ ID NO 8
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggcacgggc agcuugccgg guuuuagagc uaugcu                             36
```

NANO/MICROMOTORS FOR ACTIVE AND DYNAMIC INTRACELLULAR PAYLOAD DELIVERY

CROSS-REFERENCE TO RELATED APPLICATIONS

This patent document claims the priority to and benefits of U.S. Provisional Patent Application No. 62/477,877 entitled "NANO/MICROMOTORS FOR GENE-THERAPY" filed on Mar. 28, 2017. The entire content of the aforementioned patent application is incorporated by reference as part of the disclosure of this patent document.

SEQUENCE LISTING

The instant application contains a Sequence Listing which has been submitted electronically in ASCII format and is hereby incorporated by reference in its entirety. Said ASCII copy, created on Jun. 22, 2018, is named 009062-8350_US01_SL.txt and is 2,474 bytes in size.

TECHNICAL FIELD

This patent document relates to systems, devices, and processes that use nanomotor technologies.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, and/or a nanosystem can exhibit various unique properties, e.g., including optical properties and/or electrical, that are not present in the same materials at larger dimensions and such unique properties can be exploited for a wide range of applications. These nanostructures can be designed for use in challenging biomedical applications including diagnostics and therapeutic treatments.

SUMMARY

Disclosed are motile nano- and microstructures, devices, systems and methods thereof, for active and dynamic intracellular delivery of a payload to a target cell or tissue.

In some aspects, a nanomotor for intracellular payload delivery includes an asymmetric body having a concave cavity at one end of the nanowire body; a functionalization layer on an outer surface of the nanowire body; and a payload substance coupled to the nanomotor by the functionalization layer in a biologically active conformation, in which the payload substance is attached to a portion of the functionalization layer or at least partially encapsulated within the functionalization layer, in which the nanomotor is operable to propel in a biological medium and into an intracellular region of a living cell to initiate an interaction of the biologically active payload substance with an intracellular constituent of the living cell.

In some aspects, a method for intracellular delivery of a compound to a living cell includes providing a plurality of nanomotors operable to propel in a medium comprising a cell, in which a nanomotor of the plurality of nanomotors includes a functionalization layer on an outer surface of the nanomotor coupling a payload substance in a biologically active conformation to the nanomotor; propelling the nanomotors in the medium to cause at least some of the nanomotors to penetrate into an intracellular region of the cell; and administering the payload substance within the intracellular region of the cell to initiate an interaction of the biologically active payload substance with an intracellular constituent of the cell.

In some aspects, a device includes a nanomotor operable to propel in a medium and penetrate into a living cell in the medium; and a nucleic acid attached to the nanomotor and including a nucleotide sequence configured to affect expression of a target gene of the cell having a complementary nucleotide sequence to that of the nucleic acid.

In some aspects, a method for gene therapy includes providing nanomotors each comprising a nanowire and a nucleic acid attached to the nanowire in a medium comprising a plurality of cells, in which the nucleic acid includes a nucleotide sequence configured to affect expression of a target gene of the cell having a complementary nucleotide sequence to that of the nucleic acid; propelling the nanomotors in the medium to cause at least some of the nanomotors to penetrate into the cell; and causing suppression of the target gene of the cell based on interaction of the nucleic acid.

The subject matter described in this patent document can be implemented in specific ways that provide one or more of the following features.

BRIEF DESCRIPTION OF THE DRAWINGS

FIGS. 11A-11C show images and data plots depicting example results from free Cas9-sgRNA complex control experiments.

FIGS. 15A and 15B show images and data plots showing the comparison of the green fluorescence protein (GFP) gene knockout efficiency using Cas9-sgRNA-modified gold nanowire motors and Cas9-sgRNA-lipofectamine.

DETAILED DESCRIPTION

Figure 1A:
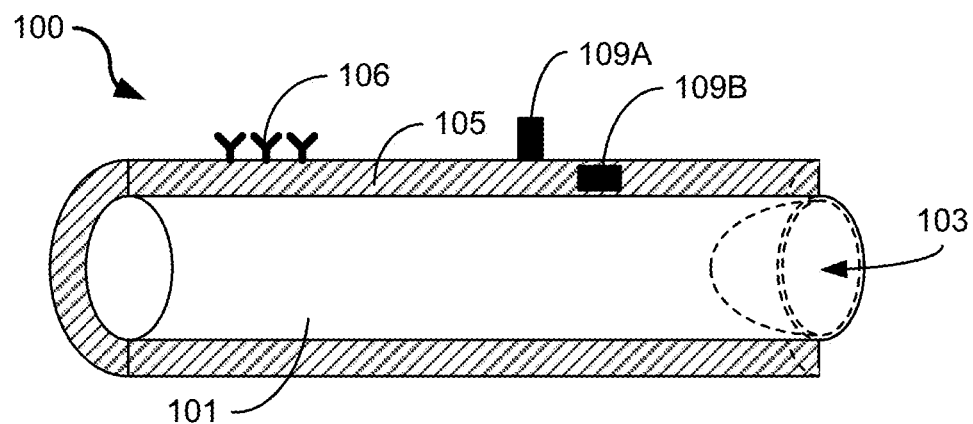
FIGS. 1A-1D show diagrams of example embodiments of nanomotors for active and dynamic intracellular payload delivery in accordance with the present technology.

Nanoscale and microscale structures (nano/microstructures) can be designed to have certain functionalities useful for various applications. One such functionality of nano/microstructures is motility for independent movement of the nano/microstructure, which can include self-propulsion with and without remote control. Such motile nanostructures and microstructures are referred to as nano- and micro-motors, nano- and micro-robots, nano- and micro-machines, nano- and micro-engines, and nano- and micro-rockets, for example.

Nanomotors and micromotors can be designed to accomplish complex and challenging biomedical tasks including biosensing at an extracellular and/or an intracellular level, facilitation of biochemical reactions between biological species in vitro and in vivo, and providing therapeutic treatment of targeted drug, gene, protein and cell delivery. However, for each biomedical application, there are several critical challenges that should be more deeply addressed for the successful implementation of the nano/micromotor in its intended use. Some examples of these specific challenges including biocompatibility of the nano/micromotor system, achievement of efficient propulsion of the nano/micromotor in complex biological media such as intravascular fluids, toxicity and the safe removal or self-degradation of the nano/micromotor system from the body upon completion of its mission, among others.

While nano/micromotor systems hold tremendous promise for providing incredible capabilities to affect biological systems for diverse applications like diagnosing and treating disease and developing deeper understanding of fundamental biology in living cells, tissues and systems, significant advancement is needed for producing a multi-functional nano/micromotor system capable of delivering on such promise and allowing for unprecedented levels of cell monitoring, manipulation and targeted intervention more specifically and safely (e.g., including at the single cell level for probing intracellular processes and ferrying their payload to sub-cellular organelles). Despite the great progress made during the past years in biosensing and delivery at cellular level, existing nano/micromotor systems are still not able to address some important challenges, such as achieving ultrasensitive detection in short time in microscale environments and releasing functional cargoes in a quick and controlled way at specific extracellular and intracellular locations with limited accessibility.

Some biomedical applications of great interest employing nanomotors or micromotors include gene therapy. Gene therapy is a medical treatment based on the use of nucleic acids as a therapeutic drug. Nucleic acid payloads can be delivered into a patient's cells to treat different diseases, such as inherited disorders and cancers. Specifically, small interfering RNA (siRNA) therapy is a promising tool for gene suppression and knockdown, offering an attractive route for treating various diseases. Despite major progress that has been done in gene silencing therapies, widespread use of RNA transfection agents is still a challenge due to the lack of targeting modalities, limited loading efficiency, internalization barriers, and biocompatibility issues. Critical needs remain to ensure safe, efficient intracellular uptake and knockdown.

Disclosed are motile nano- and microstructures, devices, systems and methods thereof, for active and dynamic intracellular delivery of a payload to a target cell or tissue, which can be used in a variety of biomedical applications including, but not limited to, gene therapy. The disclosed nanomotors and micromotors are structured to include a drive mechanism to move and navigate in a biological media, e.g., in vitro or in vivo; a cell targeting and/or attachment mechanism to locate and contact a target cell or tissue in the media; a cellular uptake mechanism to facilitate entrance of the payload-carrying nano/micromotor; and/or a payload release mechanism to selectively deploy the payload with the target cell or tissue.

Example embodiments of the motile nanostructures and microstructures in accordance with the present technology can include a tubular shape, e.g., including, but not limited to, a cylindrical or conical geometry, in which, for example, one dimension (e.g., such as the diameter of the tube) is in the nanometer regime and another dimension (e.g., such as the length of the tube) is in the micrometer regime. For example, nanoscale or microscale structures can be configured to have a particular shape and geometry, including but not limited to tubes, wires, spheres, ovals, cones, cylinders, or other. In some embodiments, for example, the motile nano/microstructures can include one or multiple structural layers, e.g., having an inner layer formed of a first material and an outer layer formed of a second material, or include the inner layer of the first material, the outer layer of the second material or the first material, and one or more interior layers between the inner and outer layers. In some embodiments, for example, the motile nano/microstructures can include one or multiple segments coupled together to form the nano/microstructure, e.g., in which multiple segments can include a first material and one or more other materials. In some embodiments, the engineered nano/micromotors do not include a fuel and instead are propelled in the fluid due to a remote energy source that triggers propulsion, such as applied ultrasound waves creating a pressure gradient across the body of the nano/microstructure by the ultrasound waves penetrating the concave rear end of the nano/micromotors. In some embodiments, for example, the motile nano/micromotor can be functionalized to attach other molecules, e.g., such as a fuel substance and/or payload to interact with a target of the biological environment. In some embodiments, for example, the nano/microstructure can be partially or fully coated by an outer coating that can provide various functionalities of the motile nano/microstructure. For example, the outer coating can include a polymer coating to protect the nano/microstructure from certain conditions in an environment that the motile nano/micromotor is deployed or travels through, such that the nano/microstructure may be passive until the outer polymer coating is removed, e.g., via environmental conditions of the biological environment.

For example, the motile nano/microstructure can be modified to attach one or more biomolecules, including but not limited to, nucleic acids, lipids, carbohydrates, peptides, proteins, enzymes, hormones, antibodies, glycoproteins, glycolipids, organelles, endotoxins, viruses, and other biological materials and biomarkers, to be delivered to delivered to the intracellular region of a living cell, e.g., including but not limited to healthy cells, cancer cells, bacterial cells, or other types of cells. The disclosed active and dynamic intracellular payload delivery nano/micromotors can be remotely-propelled or self-propelled in fluid, including biological fluids, such as but not limited to, intracellular fluid (e.g., cytoplasm) and extracellular fluid (including interstitial fluid, transcellular fluid, plasma), blood (e.g., blood serum, blood plasma), cerebrospinal fluid, aqueous humor and vitreous humor, bile, digestive fluid (including gastric juice and intestinal juice), lymphatic fluid and endolymph and perilymph, mucus (including nasal drainage and phlegm), peritoneal fluid, pleural fluid, saliva, sebum (e.g., skin oil), semen, sweat, tears, urine, vaginal fluids, and bacterial lysates. Other example fluids in which the disclosed active and dynamic intracellular payload delivery nano/micromotors can be remotely-propelled or self-propelled include non-biological fluids, such as, water, salt-containing water, sugar-containing water, juice, and oil-based fluids. The motile nanostructures and microstructures can be provided to the fluid media in a sample or solution, e.g., which can be ingested or injected into a host organism in vivo or in an in vitro container with one or more cells, e.g., such as a petri dish, well plate, test tube, microarray chip, or other container.

The motile nanostructures and microstructures are hereinafter referred to as nanomotors for brevity.

Figure 1B:
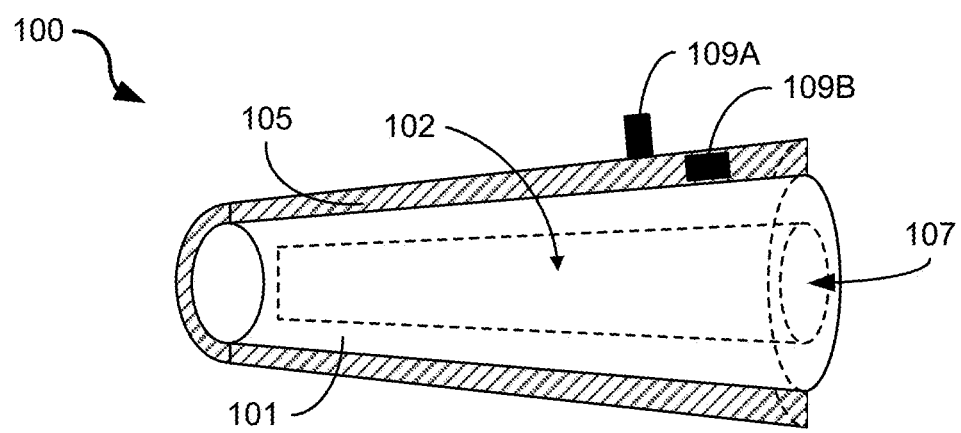
Figure 1C:
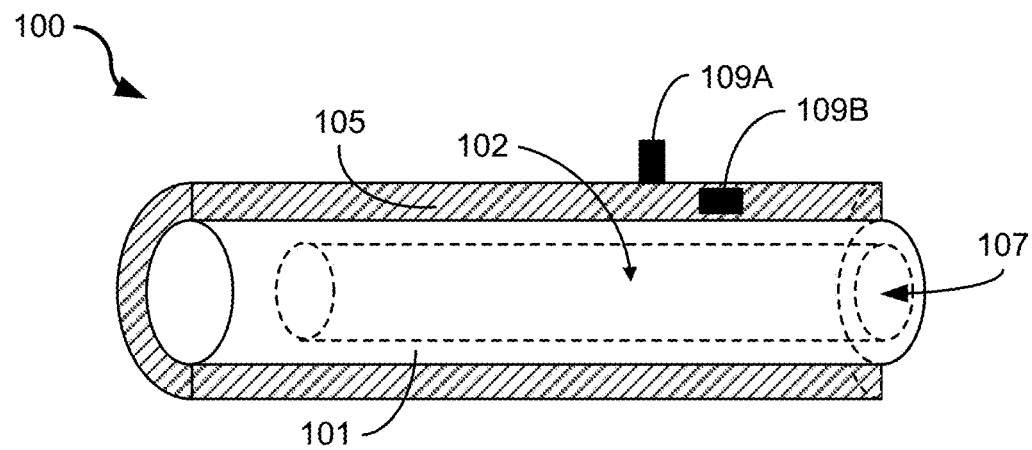
Figure 1D:
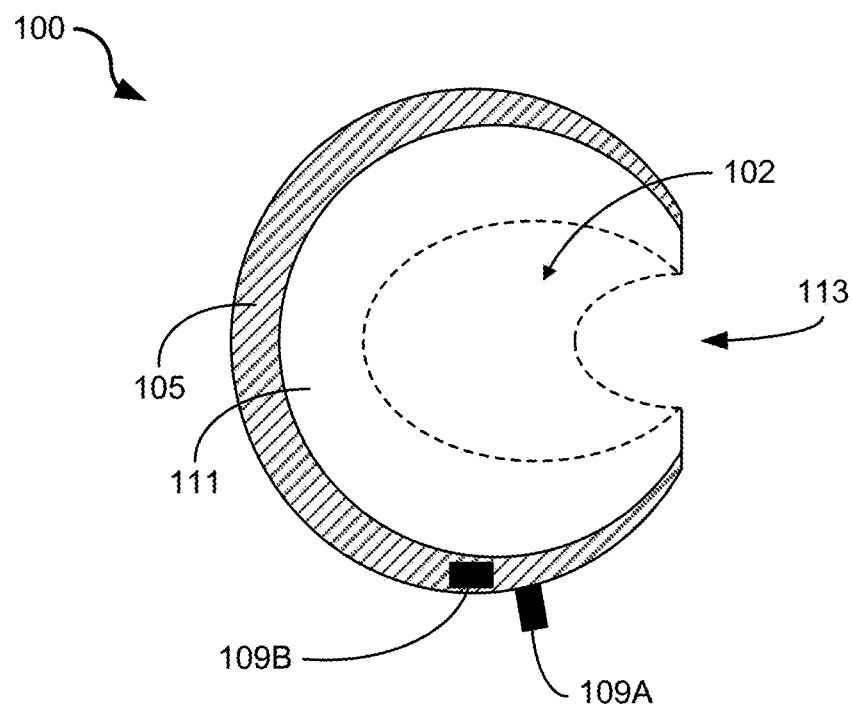

FIG. 1A shows a diagram of an example embodiment of a nanomotor 100 for active and dynamic intracellular payload delivery in accordance with the present technology. The example nanomotor 100 is depicted in a cylindrical shape in FIG. 1A, but it is understood that other shapes can also be implemented, such as a conical shape or a tubular shape as shown in FIGS. 1B and 1C, respectively, and spherical, oval or other rounded shapes as shown in FIG. 1D. In the example shown in FIG. 1A, the nanomotor 100 includes a structure or body 101 having a concave cavity or opening 103 located at one end of the body 101. In some examples, the body 101 includes a single material, e.g., gold, platinum, nickel, silver, an alloy, polyaniline (PANI) polymer, or other material. In some embodiments, the nanomotor 100 includes a diameter in the tens or hundreds of nanometer regime, e.g., 50 nm to 500 nm, and a length in the hundreds of nanometers regime to microns range, e.g., 500 nm to 10 µm. For example, the example nanomotor 100 can be configured to have an aspect ratio (diameter:length) tailored for meeting the needs of specific target or application paradigms; examples including in a range of 1:100 to 1:4. Whereas, in some embodiments, for example, the body 101 can be formed of multiple layers, e.g., such as a bi-layer body including an inner layer of a first material and an outer layer formed of a second material. For example, at least one of the multiple layers of the body 101 can include an embedded layer of a magnetic material that permits external guidance for precision steering of the nanomotor 100.

The nanomotor 100 includes a functionalization layer 105 attached to at least a portion of the outer surface of the body 101 to attach and/or encapsulate a payload 109 for active and dynamic delivery to the intracellular region of a cell by the nanomotor 100. In the example shown in FIG. 1A, the functionalization layer 105 attaches the payload 109A to the nanomotor 100, and the payload 109B is encapsulated in the functionalization layer 105. Examples of the payload 109 include a nucleic acid or nucleotide, a protein, amino acid or peptide, or a complex of biological material or compound. The nanomotor 100 is able to attach and/or encapsulate the payload 109 in a manner that preserves the bioactivity of the payload 109, such that when delivered intracellularly, the payload is available to interact with the intracellular target material without any further activation or modification of the payload 109. In this manner, the disclosed intracellular delivery mechanism provided by the nanomotor 100 is an active intracellular delivery of the payload 109. In some embodiments, for example, the nanomotor 100 can optionally incorporate specific target receptors 106 on the nanomotor surface to facilitate a cell-specific targeted delivery to target cells, e.g., tumor cells.

In some implementations, the active and dynamic intracellular payload delivery nanomotors 100 are included in a system for intracellular payload delivery including an acoustic (e.g., ultrasound) wave transmission system. The ultrasound system can produce a remote ultrasound pulse (or pulse stream) that interacts with the rigid surface of the asymmetric body of the nanomotor 100, like the concave end 103 of the example in FIG. 1A, to cause the nanomotor 100 to propel in a direction opposite the concave cavity 103. Such propulsion can include sufficient thrust and force to pierce and penetrate into a living cell, without damaging the cell to threat its viability, thereby entering the cell so as to deploy the payload intracellular. Inside the cell, the nanomotors 100 can still move, providing a dynamic delivery mechanism of the payload inside the cell.

Other example features of the nanomotors 100 can include structural and functional features of acoustically-driven nano/micromotors and ultrasound systems described in U.S. Patent Publication No. 2015/0013304 titled "ACOUSTICALLY TRIGGERED NANO/MICRO-SCALE PROPULSION DEVICES", which is incorporated by reference as part of the disclosure of this patent document for all purposes.

In some embodiments, like those shown in FIGS. 1B, 1C and 1D, the nanomotor 100 can include a hollowed interior region 102 within the body 101 that spans from an opening 107 deep into the interior of the body 101. In some examples, the interior region 102 can have a cross section spatially reducing in size along a longitudinal direction from the opening 103, like that shown FIG. 1B; whereas in other embodiments, the interior region 102 can have a uniform volume with respect to the walls provided by the body 101, like that shown in FIG. 1C. In some embodiments, for example, the interior region 102 can span between both ends of the body 101. As shown in the diagrams of FIGS. 1B and 1C, the nanomotor 100 includes the functionalization layer 105 attached to at least a portion of the outer surface of the body 101 to attach and/or encapsulate the payload 109 for active and dynamic delivery to the intracellular region of a cell.

FIG. 1D shows a diagram of an example embodiment of the nanomotor 100 having a nanoball or microball body 111 of a rounded shape (e.g., including but not limited to spherical, oval, elliptical, etc.) that includes a concave cavity or opening 113 located at one end of the nanoball or microball body 111. In some embodiments, the nanoball or microball body 111 includes the hollowed interior region 102 that spans from the opening 113. The nanoball/microball motor 100 includes the functionalization layer 105 attached to at least a portion of the outer surface of the body 111 to attach and/or encapsulate the payload 109 for active and dynamic delivery to the intracellular region of a cell. In some embodiments, the nanosphere or microsphere body 111 includes a first length in one dimension (e.g., longest diameter) in the hundreds of nanometer regime to microns range, e.g., 500 nm to 10 µm, and a longitudinal length in a direction through the concave cavity or opening 113 in the hundreds of nanometers regime to microns range, e.g., 500 nm to 10 µm. For example, the example nanoball/microball motor 100 can be configured to have an aspect ratio (diameter:length) tailored for meeting the needs of specific target or application paradigms; examples including in a range of 1:20 to 1:1. In some embodiments, the body 111 includes a single material, e.g., gold, platinum, nickel, silver, an alloy, polyaniline (PANT) polymer, or other material. Whereas, in some embodiments, the body 111 can be formed of multiple layers, e.g., such as a bi-layer body including an inner layer of a first material and an outer layer formed of a second material. For example, at least one of the multiple layers of the body 111 can include an embedded layer of a magnetic material that permits external guidance for precision steering of the nanoball/microball motor 100. In some implementations, for example, the nanoball/microball motor 100 can be driven for intracellular delivery of the payload 109 based on an applied acoustic (e.g., ultrasound) signal and/or applied magnetic field. For example, an ultrasound system can produce a remote ultrasound pulse (or pulse stream) that interacts with the rigid surface of the asymmetric body of the nanoball/microball motor 100, like the concave end or opening 113 of the example in FIG. 1D, to cause the nanoball/microball motor 100 to propel in a direction opposite the concave cavity or opening 113.

Other example features of the nanomotor 100 can include the body 101 structured as a multi-segment nanowire diode and nanowire propeller like those described in U.S. Patent Publication No. 2013/0241344 titled "FUEL-FREE NANOWIRE MOTORS", which is incorporated by reference as part of the disclosure of this patent document for all purposes. Other features of the nanomotor 100, e.g., such as features associated with the body 101 and/or the functionalization layer 105, can include structural and functional features described in U.S. Patent Publication No. 2014/0045179 title "NANO/MICROSCALE VEHICLES FOR CAPTURE AND ISOLATION OF TARGET BIOMOLECULES AND LIVING ORGANISMS", U.S. Patent Publication No. 2013/0084569 titled "NANOMOTORS AND MOTION-BASED DETECTION OF BIOMOLECULAR INTERACTIONS", U.S. Pat. No. 9,352,963 titled "NANOMOTOR-BASED PATTERNING OF SURFACE MICROSTRUCTURES", all of which are incorporated by reference as part of the disclosure of this patent document for all purposes.

Further examples of embodiments and implementations of the motile nanostructures and microstructures in accordance with the present technology are described for example applications of active and dynamic intracellular payload delivery, including nucleic acid delivery for gene therapy, Cas9/sgRNA complex for gene editing, and Caspase-3 for protein-based therapeutic treatment.

Example Implementations of Nanomotors for Intracellular siRNA Delivery

Small interfering RNA (siRNA) therapy is a promising tool for gene suppression and knockdown, e.g., offering an attractive, alternative route for treating various diseases. Such knockdown can occur once the siRNA strand is incorporated into the RNA-induced silencing complex, which is then guided to the target mRNA sequence to be excised, ensuring that certain undesirable target proteins will no longer expressed within the cell. Yet, widespread use of RNA transfection agents is challenging due to the lack of targeting modalities, limited loading efficiency, internalization barriers, and biocompatibility issues. One challenge includes the development of safe and effective delivery materials to ensure the broad clinical application of siRNA.

However, due to the negatively charged cell membrane surface and the anionic nature of siRNA, the use of cationic transfection agents or targeting ligands is necessary to ensure safe, efficient intracellular uptake and knockdown. This pitfall in RNA interference (RNAi) therapy, and more specifically siRNA delivery has been circumvented through different strategies, including the use of metal nanoparticles (NPs), cationic lipid NPs, cationically condensed siRNA microhydrogels, and polymerization along with subsequent conjugation of siRNA to receptor targeted ligands.

Example embodiments of the disclosed nanomotor structures, devices, systems and methods in accordance with the present technology provide an attractive design for siRNA carriers engineered using a framework of DNA nanotechnology. DNA is a genomic carrier and as a building material for supramolecular assemblies. The specific bonding of base pairs makes DNA strands particularly suited as building blocks to assemble highly structured materials with specific nanoscale features. In the drug delivery field, DNA nanotechnology enables the precise control of morphology and loading efficacy of delivery cargos and offers a new approach to delivering small molecules, siRNA, and diagnostic agents.

In some embodiments, the nanomotor 100 can include a nanomotor body operable to propel in a medium and penetrate into a living cell in the medium; and a nucleic acid complex attached to the nanomotor body and including a nucleotide sequence configured to affect expression of a target gene of the living cell having a complementary nucleotide sequence to that of the nucleic acid complex.

Gene therapy can be carried out by the nanomotor device by providing one or more of the nanomotors in the medium comprising a plurality of cells; driving propulsion of the nanomotors in the medium to cause at least some of the nanomotors to penetrate into the cell; and causing suppression of the target gene of the cell based on interaction of the nucleic acid.

For example, the nucleic acids are anchored to nanomotor body 101 to form a hybrid entity (e.g., nucleic acid-functionalized nano/micromotor) that acts as a carrier that can be propelled in different ways, e.g., including but not limited to localized chemical conversion (e.g., such as magnesium, zinc, glucose) of a material on the nanomotor with a substance in the medium to cause propulsion or an applied external energy source (e.g., such as ultrasound, electricity, magnetic and light actuations) to create a field that generates a force to drive the nanomotor in the medium. The nucleic acid complex attached to the nanomotor body can include DNA, RNA, and any variant thereof. This example DNA-nano/micromotor hybrid structure represents an efficient tool that addresses challenges associated with therapeutic DNA-payloads transportation and intracellular delivery, e.g., enabling the co-delivery of multiple types of therapeutics as the anchoring DNA template can be modified to allow for more binding regions. In some implementations, the present technology can be extended to include actuating DNA nanotechnology onto the nanomotor 100, thus allowing unparalleled control of site-specific therapeutic delivery.

In some embodiments, the nanomotor 100 can be configured as an acoustically-propelled nanowire structures modified with an interfering RNA's (siRNA) payload can be used to implement an effective intracellular gene silencing strategy. The example nanowires can include gold nanowires (AuNW), which can be wrapped with a rolling circle amplification (RCA) nucleic acid strand, e.g., RCA DNA, to serve as the functionalized layer 105 on the nanomotor body 101, e.g., which serves to anchor the siRNA therapy payload. For example, the ultrasound (US)-powered propulsion of the example AuNW can cause fast internalization and rapid intracellular movement and to an accelerated siRNA delivery and silencing response.

The example ultrasound-propellable AuNWs were utilized in example implementations to study and optimize a nanomotor gene silencing procedure, and the influence of motion, time and dosage of the nucleic acid payload for gene therapy. As discussed in further detail below, the example results show up to a 94% silencing after few minutes treatment with ultrasound-propelled siRNA-RCA DNA-AuNWs, and to a large improvement, e.g., ~13-fold, in the silencing response compared to the static modified nanowires. The example nucleic acid hybrid nanowires demonstrated a nanomotor-based method for gene silencing by measuring the GFP silencing response in two different cell lines (e.g., HEK-293 and MCF-7) and using detailed control experiments. The viability of the cells after the example nanomotors treatment was examined using the MCF-7 cancer cell line.

The example ultrasound triggered nanomotor delivery of protein- or genetic material-based payloads offers a promising method for active intracellular-based therapy, such as gene therapy, because of its localization abilities. For example, as demonstrated in the example implementations, using ultrasound as the trigger, the nucleic acid functionalized nanomotor was able to effectively and efficiently enhance siRNA silencing of targeted genes with decreased uptake time and increased target specificity. Another example benefit of the disclosed functionalized nanomotor technology includes the capability of increasing the therapeutic payloads on the delivery mechanism, e.g., such as providing a cocktail siRNA treatment of diverse siRNA payloads on the nanomotor carrier. Due to the biological barriers and physical limitations commonly faced by siRNA carrier methods, as well as long assay times, for example, there are challenges to develop a fast, efficient and biocompatible strategy for intracellular siRNA delivery and gene-mRNA silencing. The use of the example functionalized nanomotor hybrid carrier for gene therapy in accordance with some embodiments of the present technology represents an efficient tool that addresses the challenges associated with therapeutic nucleic acid payloads transportation and intracellular delivery, opening the doors for future implementation of nanoscale machines in broad gene therapy applications.

The example nanomotor device used in the example implementations for intracellular gene-therapy (e.g., a gene-silencing approach) includes a gold nanowire (AuNW) structure loaded with a small interfering RNA payload associated with the gene for Green Fluorescence Protein (GFP) by modification of the AuNW structure using a rolling circle amplification DNA sequence template via electrostatic interactions to produce the example active intracellular siRNA payload delivery nanomotors (siGFP/RCA DNA-AuNWs. The modified siGFP/RCA DNA-AuNWs were propelled under an acoustic energy (e.g., ultrasound (US)) field, and, upon entry into a living cell, the siGFP/RCA sequence starts to suppress the gene-mRNA expression and thus turns the green cell-fluorescence "OFF". Such a process, for example, is facilitated by the ultrasound-induced pre-concentration of AuNWs and cells into localized pressure nodes. Once in there, for example, the ultrasound-propelled nanomotors bombard the cell's exterior (e.g., cell membrane), leading to aggregation, piercing and penetration, enabling intracellular delivery of siRNA.

Figure 2A:
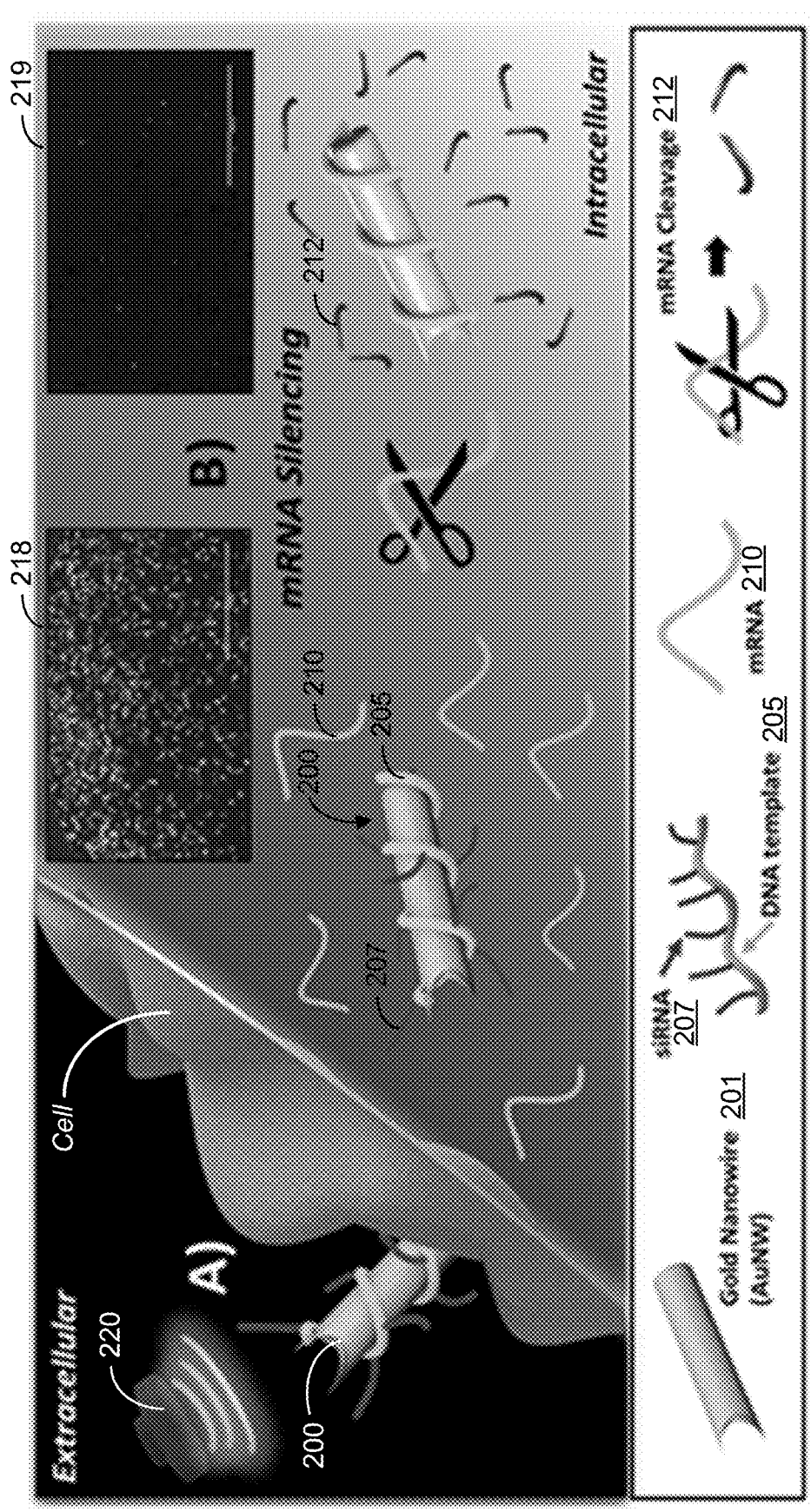
FIG. 2A shows an illustrative diagram depicting an intracellular gene-therapy implementation using an example siRNA nanomotor delivery device for gene silencing in accordance with the present technology.

FIG. 2A shows an illustrative diagram of an example intracellular gene-therapy application using the siRNA nanomotor-based gene silencing approach in accordance with the present technology. The diagram depicts an example implementation of a nanomotor-based silencing approach including fluorescence images, and optical images of the acoustic movement of nanomotors inside living cells. As shown in the left-side of the diagram of FIG. 2A, extracellular side (A), an example green fluorescence protein siRNA payload/rolling circle amplification DNA template functionalized-gold nanowire, siGFP/RCA DNA-AuNW 200, penetrates inside a cell (e.g., HEK293-GFP cell) due to the movement of the nanomotor 200 under an applied acoustic field (e.g., ultrasonic waves) by an ultrasound system 220. As shown in the right-side of the diagram of FIG. 2A, intracellular side (B), a natural process for gene-mRNA silencing and knockdown inside living cells occurs by the molecular interaction of the siRNA 207 deployed from the functionalized nanomotor 200 with the mRNA 210 in the cell, cleaving the miRNA 212. For example, data described below depicts mRNA cleavage 212 observed in the images 218 and 219 by the cell-fluorescence decrease, in which the example scale bar is 1000 μm. Coupled with rapid intracellular motion and release of the siRNA, and along with the optimal siRNA loading capacity, this example approach can result in efficient suppression of target gene expression, as compared to existing gene-silencing methods. Such acceleration represents an important advantage for the potential treatment of many diseases. The example ultrasound-propelled nanomotors 200 demonstrate that the nanomotor 201 modified with the RCA DNA template 205 and a small interfering RNA's (siRNA) payload 207 can provide an accelerated gene-mRNA silencing, as compared to their static counterpart and other controls.

In the example implementations, the gold nanowires 201 were wrapped with the rolling circle amplification DNA strand template 205, which serves to anchor the siRNA therapy payload 207. The ultrasound-powered propulsion of the modified AuNWs 200 leads to fast internalization and rapid intracellular movement and hence to an accelerated siRNA delivery and silencing response. Once inside the cell, the siGFP is responsible for silencing the formation of new fluorescent proteins, e.g., as indicated by the rapid loss of the green fluorescence, which reflects an effective intracellular siRNA delivery. For example, these example gene therapy nano-/micro-motors differ from other approaches using either membrane fusion or receptor related endocytosis to enter the cell, as these ultrasound-powered nanomotors pierce and travel inside the cell.

Example implementations described herein discuss the study of different parameters related with the silencing efficiency (e.g., ultrasound propulsion time and siRNA dosage). Example results of the implementations showed the ultrasound-propelled nanomotors were attractive candidates to overcome biological barriers and physical limitations commonly faced by siRNA carrier methods. For example, these nanoscale motors can be used in a wide range of applications, including triggered drug release, decontamination, and intracellular motion and miRNA detection. The example studies demonstrate that the ultrasound propulsion facilitates the internalization of functionalized nanowire motors into cells.

Referring to FIG. 2A, an example gene-mRNA-silencing technique for delivering the siRNA payload inside the living cell, e.g., human embryonic kidney 293 cells that express GFP (HEK293-GFP), is illustrated. The fast propulsion thrust and force of the ultrasound-propelled siRNA-wrapped AuNWs lead to efficient piercing and penetration into these HEK293-GFP cells. Coupling the rapid intracellular motion, fast release of the siRNA, and optimal siRNA loading capacity, this approach results in efficient and rapid suppression of target gene expression, depicted in intracellular side (B) of FIG. 2A. The fluorescence images 218 and 219 show a natural process for gene-mRNA silencing inside living cells. For example, the images 218 and 219 show a decreased cell-fluorescence after the HEK293-GFP cells were treated during a 5 min treatment with the example US-propelled siGFP/RCA DNA-modified nanomotors 200 (image 218), and following an overnight incubation (image 219); the example scale bar in the images is 1000 µm. Such acceleration represents an important advantage for the potential treatment of many diseases. The short silencing time, efficient knockdown, high selectivity and other characteristics of the disclosed nanomotor approach are further discussed as follows.

Figure 2B:
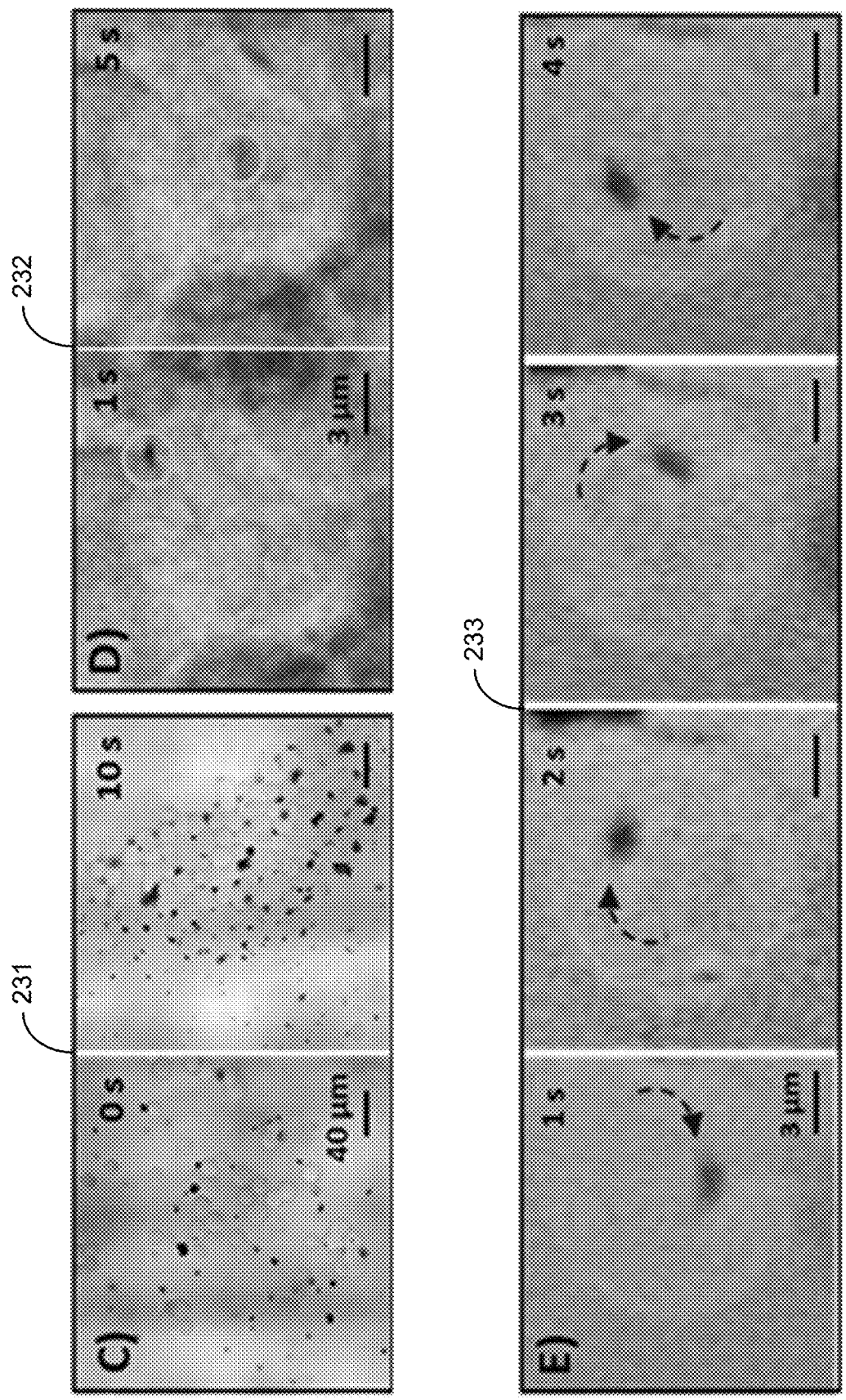
FIG. 2B shows optical time-lapse images at various intervals showing pre-concentration of example siRNA nanomotors with a cell, penetration of the siRNA nanomotors into the cell, and the spinning motion of the example siRNA nanomotors inside the cell.

FIG. 2B shows optical images depicting the pre-concentration, penetration, and motion of the example siRNA nanomotors with HEK293-GFP cells. The example time-lapse images shown in panel 231 were taken at 10 s intervals and illustrate the pre-concentration of the example siGFP/RCA DNA-modified nanowires (black dots) and HEK293-GFP cells (light spheres) under an ultrasound field. The example time-lapse images shown in panel 232 were taken at 4 s intervals and illustrate the penetration of the siGFP/RCA DNA-modified AuNWs into a HEK293-GFP cell. The example time-lapse images shown in panel 233 were taken at 1 s intervals and show the spinning motion of the siGFP/RCA DNA-modified AuNWs inside the HEK293-GFP cell. The arrows shown in the images of panel 233 indicate the direction of the motion. The ultrasound field included the following parameters, e.g., 6 V and 2.66 MHz.

Referring back to intracellular side (B) of the illustration in FIG. 2A, it is shown that, upon entry into the cell, the GFP/RCA sequence, attached to a positive cysteamine-functionalized gold nanowire surface via electrostatic interactions and wrapping, starts to suppress the gene-mRNA expression and turn the cell-fluorescence "OFF". The fluorescence images 218 and 219 confirm the intracellular the result of the example siRNA delivery. For example, the successful delivery of the siRNA payload can be assisted by the ultrasound-induced pre-concentration of the modified AuNWs and cells into localized pressure nodes, e.g., also shown in the images of panel 231 of FIG. 2B. Once concentrated in these nodes, the ultrasound-propelled nanomotors bombard the cell's exterior, leading to aggregation, piercing and penetration (e.g., shown in images of FIG. 2B, panel 232), enabling intracellular delivery of siRNA. Further evidence of internalization is illustrated by the spinning motion of AuNWs inside the cell (e.g., shown in images of FIG. 2B, panel 233). Once inside the cell, the speed of the ultrasound-propelled nanomotors is dependent on several parameters, for example, such as higher intracellular viscosity, imperfection in the nanomotor's shape, and the applied voltage.

Figure 3A:
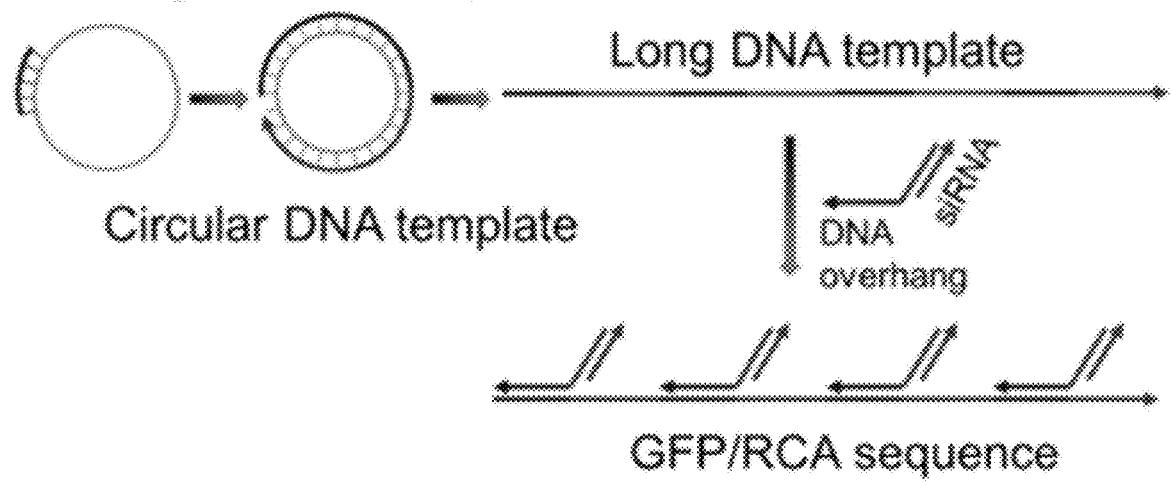
FIG. 3A-3D show illustrative diagrams and images of example data illustrating an a rolling circle amplification (RCA) technique for modifying a nanomotor structure in accordance with the present technology.
Figure 3C:
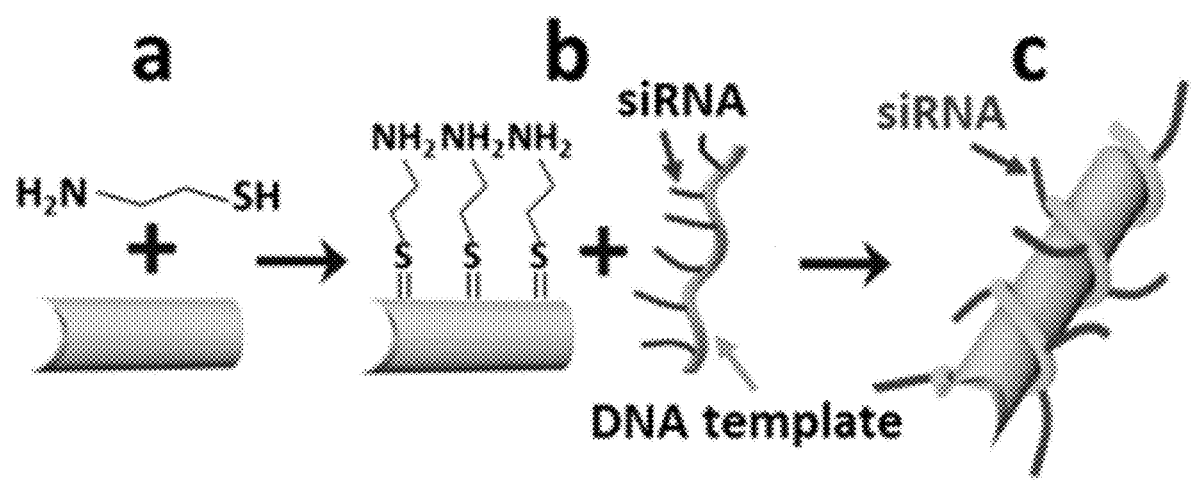
Figure 3B:
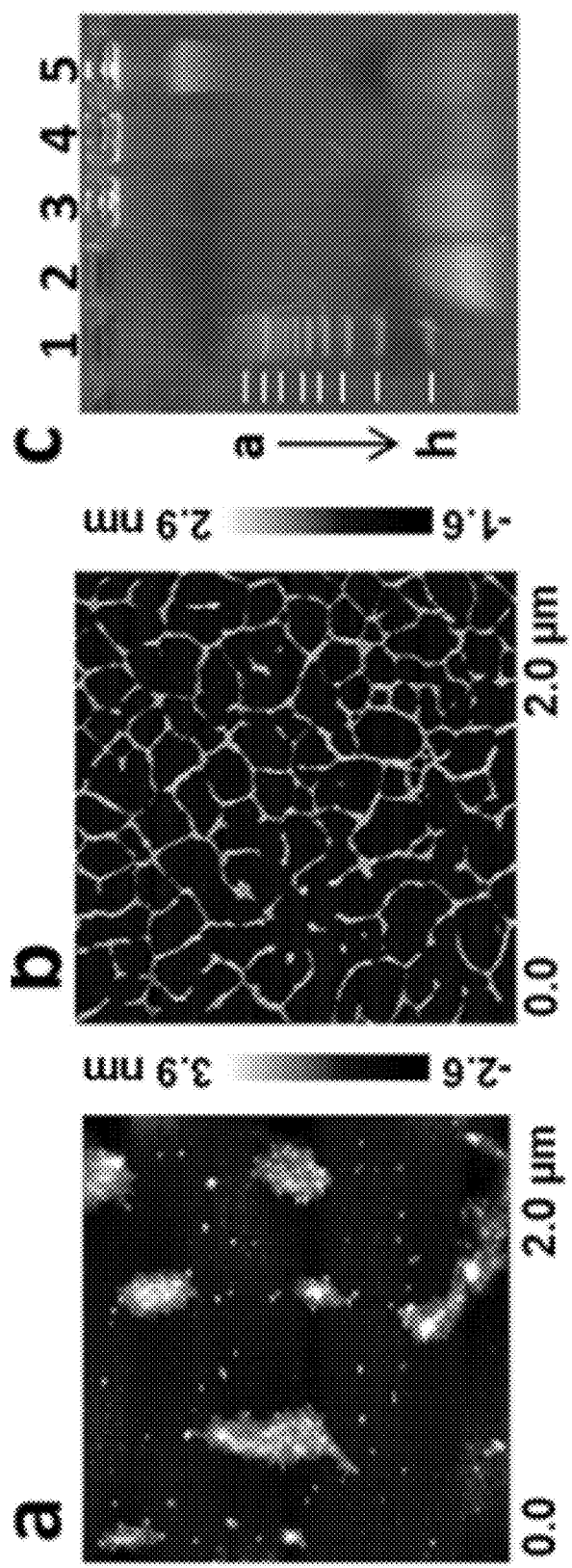

FIGS. 3A-3D show illustrative diagrams and images of example data illustrating an a rolling circle amplification (RCA) technique for modifying a nanomotor structure in accordance with the present technology. FIG. 3A shows an illustrative diagram of an example rolling circle amplification technique where a short DNA sequence is amplified to form a long single stranded DNA using a circular DNA template with repeating units, and subsequently modified with a complementary DNA overhang-siRNA sequence. FIG. 3B shows AFM images of a 2 µm scan of the RCA strand without siRNA (image (a)) and a 2 µm scan of the RCA strand with siRNA (image (b)), and shows a 0.5% native agarose gel to confirm the binding of the siRNA to the RCA product in gel image (c), in which: well 1 corresponds to marker ladders, from a to h: 8 Kb, 5 Kb, 3.5 Kb, 2.5 Kb, 2 Kb, 1.5 Kb, 1 Kb, 500 bp, respectively; wells 2-5 contains 1 µg of siRNA and 0, 5, 10 and 20 µL of RCA, respectively). FIG. 3C shows an illustrative diagram of an example functionalization of the AuNWs with GFP/RCA, including (a) coating with cysteamine, (b) amine activation and conjugation with GFP/RCA sequence; (c) the resulting GFP/RCA-modified AuNW. FIG. 2 panel (D) shows SEM images characterizing a GFP/RCA-AuNW: SEM image and EDX analysis of Au and P (corresponding to the GFP/RCA phosphate backbone).

RCA is a process that utilizes a circular nucleic acid template, created by ligating a single strand of DNA or RNA closed with ligase and then amplifying that template through the use of polymerase. The length of the final product is determined by the polymerase concentration and its reaction time. This process can be extrapolated to develop sensors or complex 3D DNA structures via origami techniques that are used to deliver therapeutics and diagnostic agents. The circular template for the RCA product used in these experiments contains two repeating units, a non-coding spacer region and a binding region of 20A base pairs (bp) that binds to the target siRNA (e.g., GFP in the example implementations). When amplified by RCA, these segments repeat and allow for the binding of multiple units of siRNA, e.g., illustrated in FIG. 3A.

The 20A bp region, when transcribed by phi29 DNA polymerase, through RCA, creates a 20T region which can then bind to the GFP-targeting siRNA which is modified with an additional 20A DNA nucleotide region on the sense strand. Once the siRNA has bound to the long stranded RCA product, the RCA product transitions from a large clump of DNA and straightens out into long stranded regions, resulting in the final GFP/RCA product. This can be clearly seen in the example AFM images of FIG. 3B, which show the RCA product without the siRNA as large coiled balls of long-stranded DNA (image (a)), and, when hybridized to the siRNA, as a spread out network of strands (image (b)). This expanded structure leads to a smaller diameter that facilitates a higher volume of the RCA/siRNA product entering into a 0.5% agarose gel in image (c) of FIG. 3B.

Each volume of RCA in the gel was hybridized with the same amount of the double stranded siRNA product. As shown, the upper RCA/siRNA bands (e.g., 2-5 wells) become more intense with increasing amounts of RCA, for example, which can be due to the fact that the siRNA acts as a "declumping" agent, thus allowing more bound product to enter the gel. The intensity change in the lower siRNA bands (e.g., 2-5 wells) becomes fainter upon adding more RCA, indicating the successful binding of the siRNA and subsequent shift in size. Once bound, an alternating single and double-stranded RCA product is created, which allows the product to wrap onto the positively-charged surface of the gold nanomotor. This provides the ability to localize siRNA in a controlled fashion onto the motor and increase the knockdown efficiency.

Figure 3D:
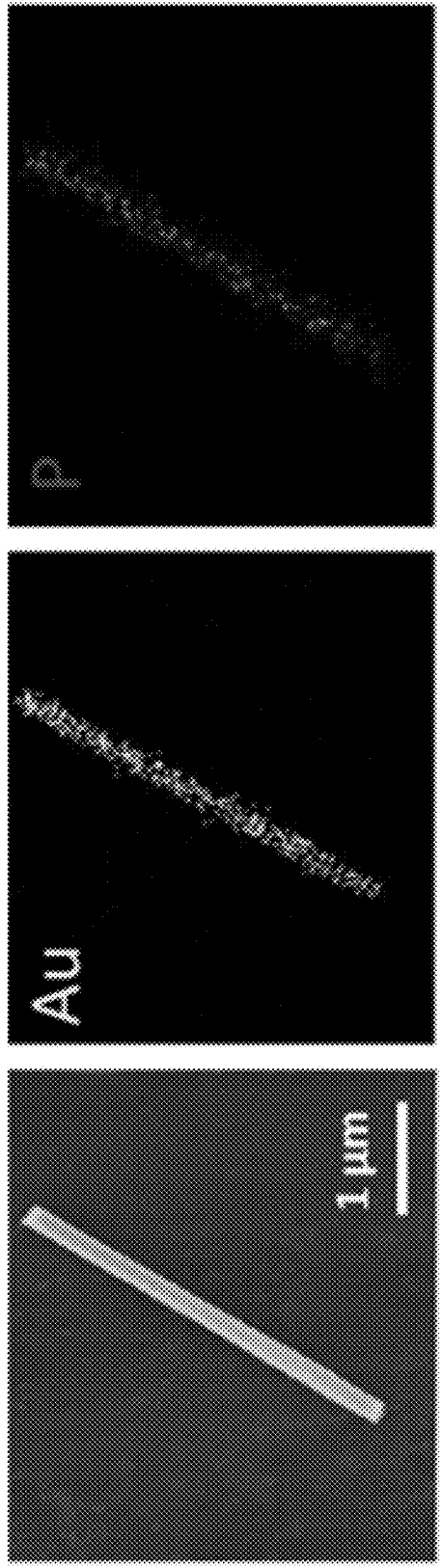

In the example implementations, the gold nanowires were synthesized by a template electrodeposition method and further functionalized with cysteamine to obtain the appropriate self-assembly monolayer (SAM), and later with the GFP/RCA sequence. Briefly, the example template-directed electrodeposition protocol includes depositing the gold within the cylindrical micropores of an alumina membrane template, followed by dissolution of the membrane and release of the AuNWs. The nanomotor design and functionalization was characterized to assure an efficient siRNA loading and intracellular delivery. Scanning electron microscopy (SEM) image was carried out to examine the structural morphology of the siGFP/RCA-AuNWs. The SEM images of FIG. 3D show an example siGFP/RCA-modified AuNW with ~4 µm length and a diameter of 200 nm, which reflects the electrical charge and pore size of the anodic aluminum oxide (AAO) membrane template, respectively, used in the fabrication process. Furthermore, the acoustic propulsion mechanism relies on ultrasound streaming over the rigid metallic surface of the asymmetric AuNW, which contains a concave end used for the motion. This combined with fluid streaming leads to enhanced propulsion thrust capable of piercing and internalization of the example AuNWs into cells. In the example implementations, the AuNWs were modified via self-assembly of the cysteamine bifunctional agent on the gold surface to obtain a positively-charged nanomotors surface and allow an electrostatic interaction with the negative charge of the GFP/RCA sequence. The EDX analysis of FIG. 3D also demonstrates the composition of the gold-nanomotor and the successful modification of motor with the siGFP/RCA sequence, as confirmed by the phosphate content of the siGFP/RCA-modified AuNW, corresponding to the phosphate backbone of the siGFP/RCA sequence.

Figure 4A:
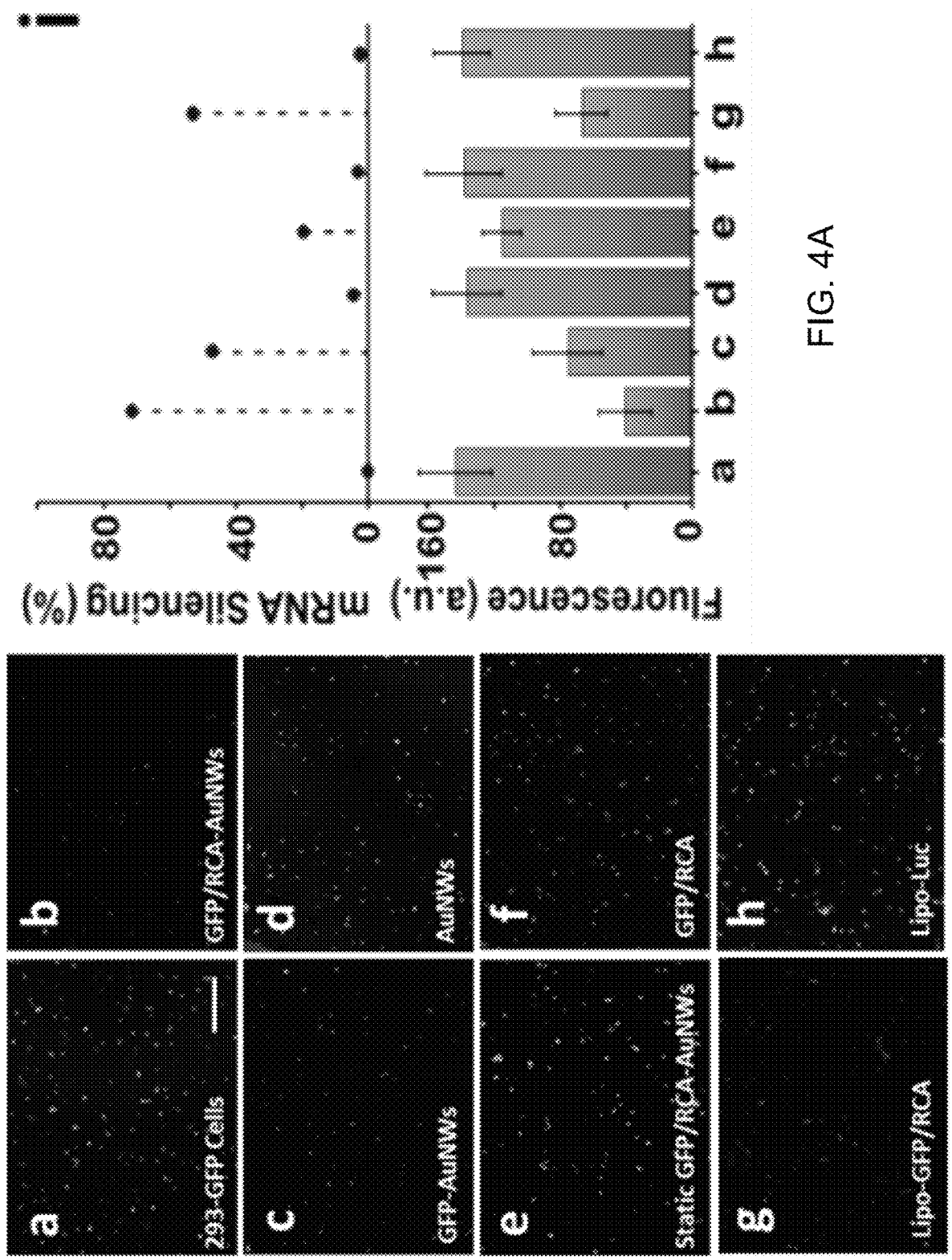
FIGS. 4A-4D show fluorescence images and data plots depicting the example HEK293-GFP cells and MCF7-GFP after exposure to different experimental and control conditions of the example nanomotors.
Figure 4B:
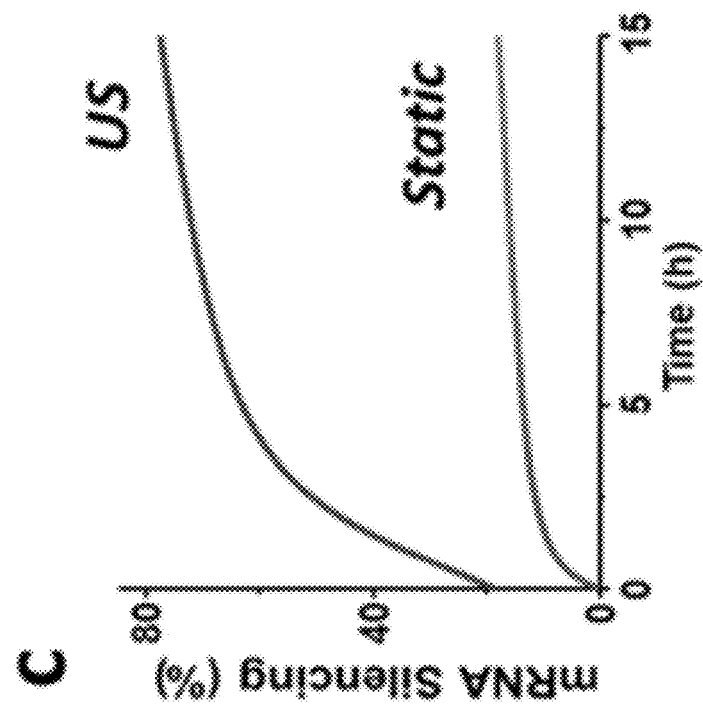
Figure 4B:
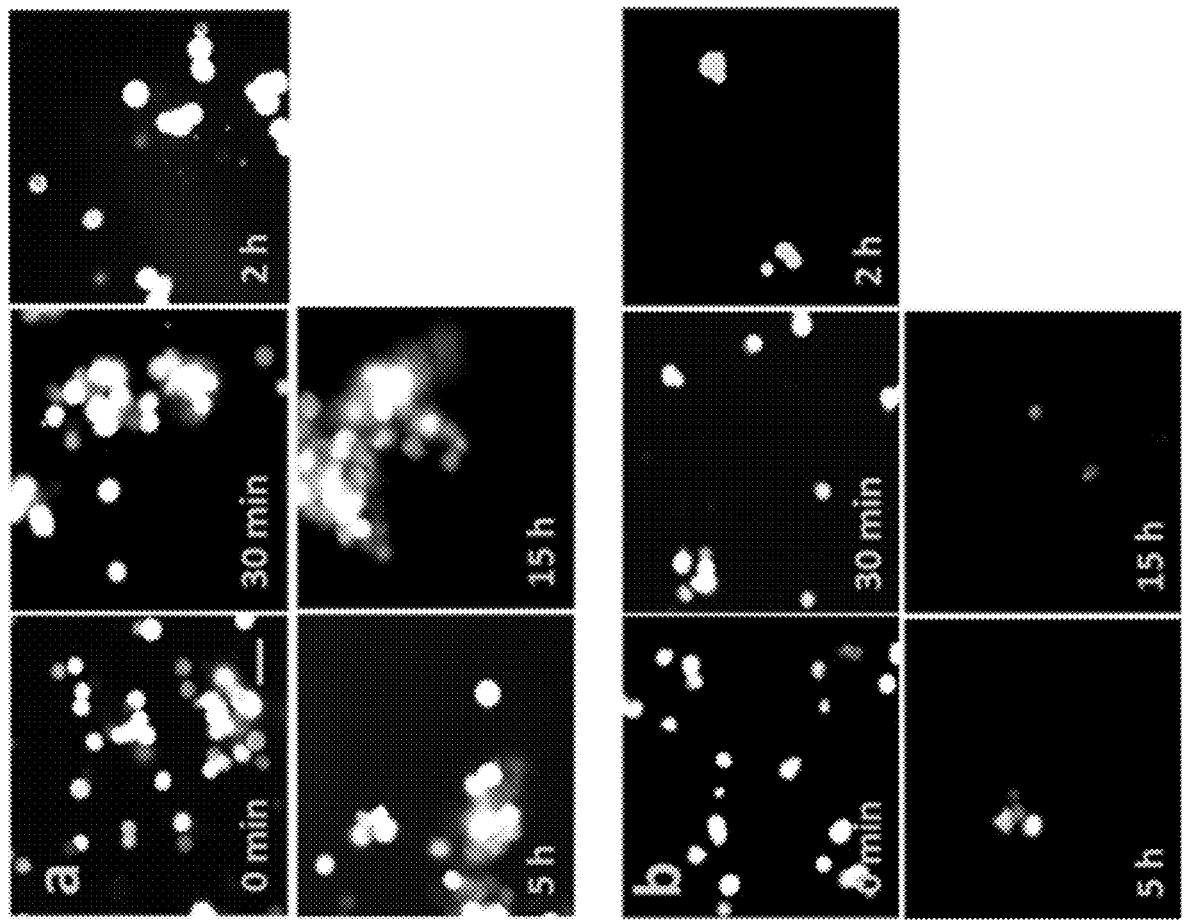
Figure 4C:
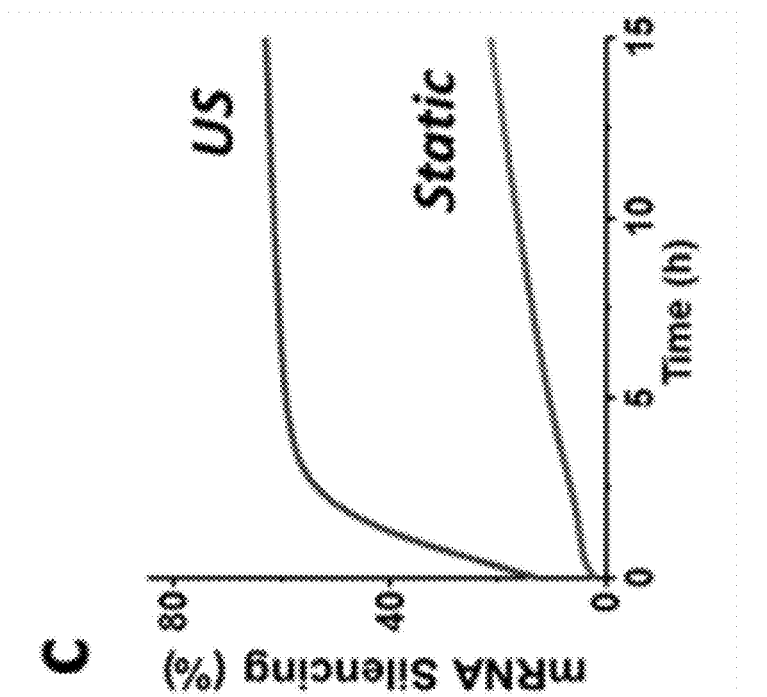
Figure 4C:
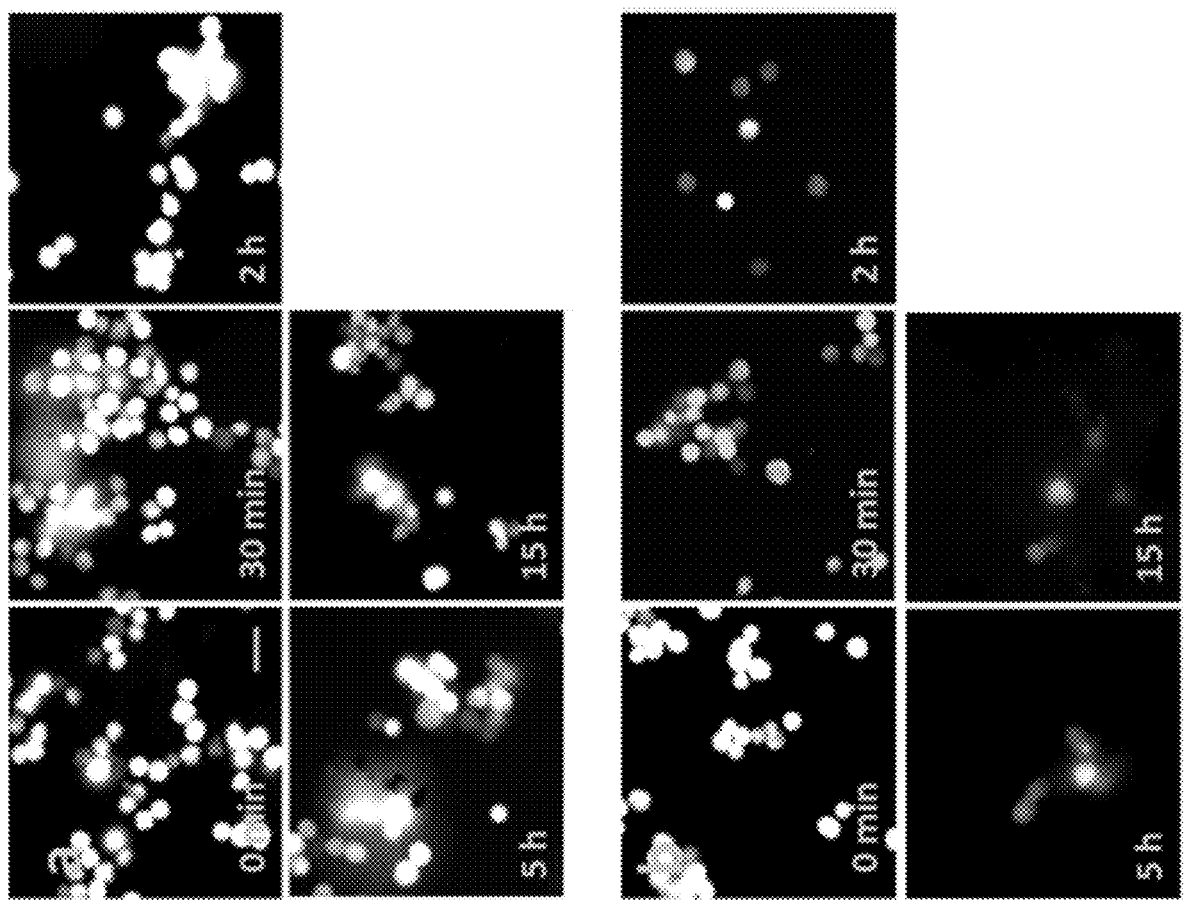

FIGS. 4A-4D show fluorescence images and data plots depicting the example HEK293-GFP cells and MCF7-GFP after exposure to different experimental and control conditions of the example nanomotors. FIG. 4A shows fluorescence images of the HEK293-GFP cells obtained after exposure to different experimental (control) conditions (a-h): (a) untreated cells, (b) cells treated with the US-powered-GFP/RCA-AuNWs, (c) cells treated with US-powered-GFP-AuNWs, (d) cells treated with US-powered-unmodified-AuNWs, (e) cells treated with static-GFP/RCA-AuNWs, (f) cells treated with free GFP/RCA, (g) cells treated with free lipofectamine/GFP/RCA, and (h) cells treated with free lipofectamine-luciferase. FIG. 4A plot (i) shows a graph depicting gene-mRNA silencing percentage and fluorescence quantification corresponding to each control, in which the example ultrasound conditions included 6 V, 2.66 MHz and 5 min; cells were incubated overnight; example scale bar of 500 µm. FIGS. 4B and 4C show images from a time-silencing study with HEK293-GFP cells (FIG. 4B) and MCF7-GFP cells (FIG. 4C), e.g., comparing in both cell lines. Panels (a) of FIGS. 4B and 4C show static GFP/RCA-AuNWs with HEK293-GFP cells and MCF7-GFP cells, respectively, after different incubation times (0, 0.5, 2, 5 and 15 h); scale bar, 50 µm. Panels (b) of FIGS. 4B and 4C show US-propelled GFP/RCA-AuNWs with HEK293-GFP cells and MCF7-GFP cells, respectively, after different incubation times (0, 0.5, 2, 5 and 15 h); scale bar, 50 µm. Plots (c) of FIGS. 4B and 4C show graphs depicting the dependence of the mRNA silencing % upon the incubation time after treating the HEK293-GFP cells and MCF7-GFP cells (FIGS. 4B and 4C, respectively) with the GFP/RCA-AuNWs in the absence and presence of the US field. US conditions: 6 V, 2.66 MHz and 5 min.

The example implementations included studies to demonstrate the feasibility of the nanomotors-based approach toward enhanced mRNA silencing. Various controls (FIG. 4A) and time-silencing dependence studies were carried out under static and US conditions (FIGS. 4B and 4C, respectively) to investigate and optimize the in vitro intracellular mRNA silencing mechanism involved in the miRNA knockdown.

FIG. 4A shows the fluorescence results of HEK293-GFP cells after having been exposed to different conditions and incubated overnight in the adequate cellular media (e.g., the controls were compared to fluorescence signal of untreated HEK293-GFP cells (FIG. 4A, image (a)), and AuNWs were modified with 80 ng of GFP/RCA sequence). For example, the HEK 293 cell line was chosen due to its common ability to easily express recombinant proteins, such as the GFP, which can then be targeted with siRNA sequences such as GFP-targeting siRNA. As illustrated in the fluorescence image (b) of FIG. 4A, a 74% gene-silencing was obtained with the US-powered-GFP/RCA-AuNWs (e.g., 6 V, 2.66 MHz for 5 min) (FIG. 4A, graph (i): line b), as compared to 20% achieved with the GFP/RCA-AuNWs under static conditions (FIG. 4A, image (e), and FIG. 4A, graph(i): line e), e.g., ~3.7 times higher silencing when ultrasound was applied. It was demonstrated that the propulsion of the nanomotors greatly facilitates the siRNA internalization process, as this nanomotor route offers a 21-fold enhanced silencing when compared to GFP/RCA free in solution at the same concentration level (FIG. 4A, graph (i): line b versus line f). Such enhancement and performance are extremely important since current intracellular mRNA silencing strategies commonly require prolonged incubation times (e.g., 24 h-48 h), and complex systems to overcome the problems related to escape from endosome to cytoplasm. Furthermore, to ensure that the silencing efficiency was a result of the RCA surface template, for example, cells treated with US-powered-AuNWs modified with plain GFP lacking the RCA template were also analyzed, as shown in FIG. 4A, image (c)). This control experiment resulted in a significantly lower silencing efficiency compared to the use of RCA-loaded GFP (FIG. 4A, graph (i): line c). Consequently, it can be determined that the RCA template offers a higher siRNA loading capacity and leads to an increased transfection efficiency. This reflects the strong preferential binding of the siRNA to the RCA template functionalized to the nanowire, allowing for more siRNA to be confined on the nanomotors as they enter the cells. Such efficient modification of the gold nanomotor surface has a profound effect upon the efficiency of the siRNA delivery. Cells were also treated with US-powered unmodified-AuNWs (e.g., plain gold nanowires, FIG. 4A, image (d) and graph (i): line d) to exclude the possibility of any off fluorescence switching effects resulting from the nanomotor motion. To finalize the control experiments, the silencing achieved with commonly used cationic transfection agent Lipofectamine 2000 was compared with two types of siRNA, e.g., the target GFP siRNA and Luciferase siRNA, as positive and negative controls, respectively (FIG. 4A, images (g) and (h), and graph (i): lines g and h). For example, while the Lipofectamine-GFP siRNA induced knockdown, it did not lead to the same efficacy as the RCA/GFP-modified nanomotors. This phenomenon was also confirmed with a dosage-silencing dependence study using both Lipofectamine-modified siRNAs (FIG. 4D).

Figure 4D:
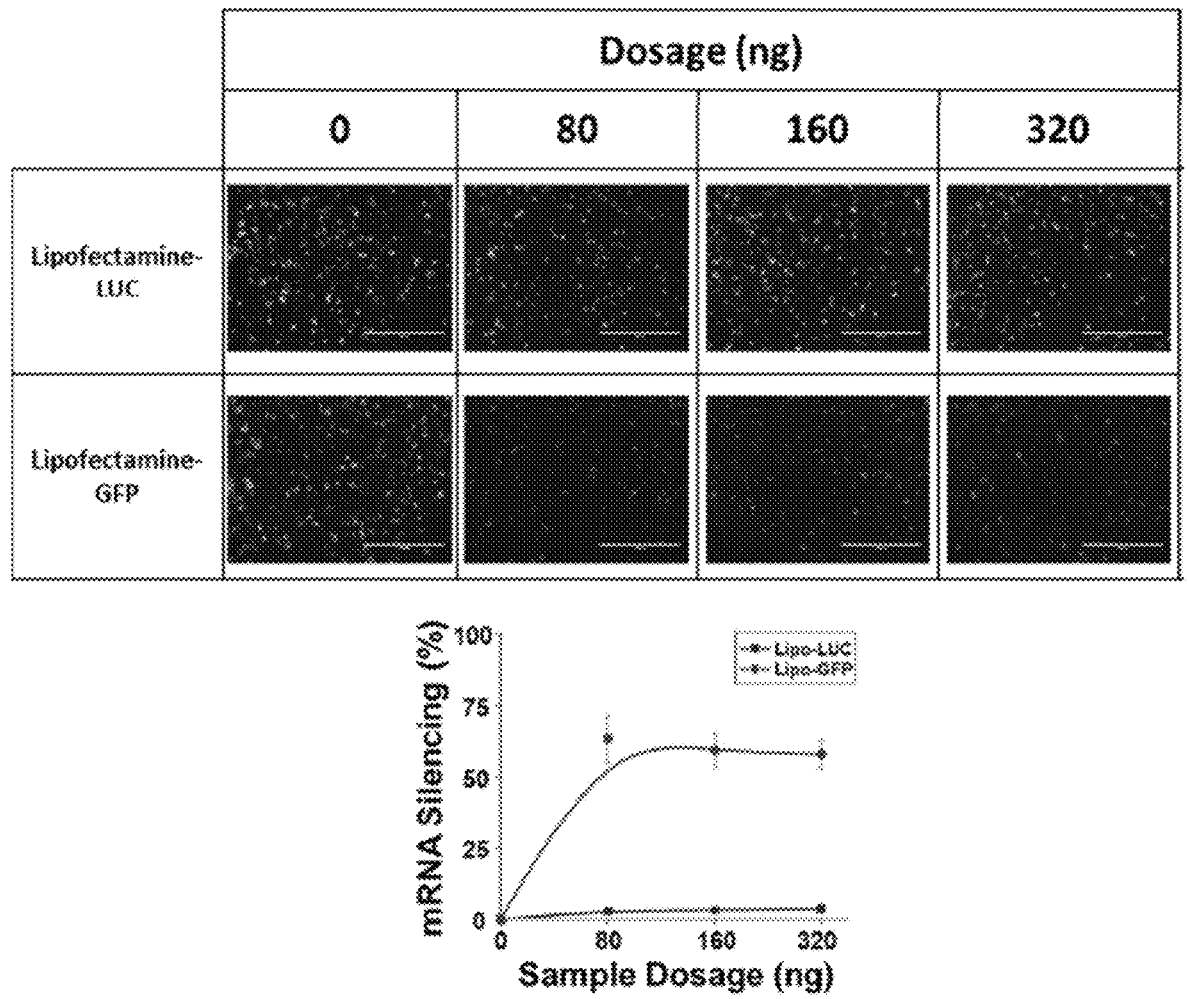

FIG. 4D shows fluorescent images and a data plot depicting the effect of amount of lipofectamine-luciferase or lipofectamine-GFP (ng) onto the gene-mRNA silencing. The mRNA silencing % increased first with the Lipofectamine-GFP siRNA dosage up to 60% knockdown with 80 ng sample, leveling off above this dosage. However, the Luciferase siRNA did not display the dosage silencing-response effect, demonstrating again the importance of the siRNA-RCA template.

The example implementations included studies to demonstrate the feasibility of the nanomotors approach toward mRNA silencing, and the fluorescence signals of HEK293-GFP and MCF7-GFP cells were compared (FIG. 4B and FIG. 4C, respectively) after different incubation times, following a 5 min treatment with the GFP/RCA-AuNWs in the absence (image panel (a) of FIGS. 4B and 4C) and presence (image panel (b) of FIGS. 4B and 4C) of the US field (e.g., 6 V, 2.66 MHz). As illustrated in FIG. 4B, image panel (a), the fluorescence of the cell did not change significantly using the static conditions, compared to the fast (e.g., 50%) silencing response after 2 h of the nanomotors treatment as illustrated in FIG. 4B, image panel (b). These example results indicate that the movement of the siRNA-modified motors leads to a ~4.3 fold enhancement in the siRNA silencing after an overnight incubation (FIG. 4B, graph (c)), which confirms the knockdown results obtained in the previous control studies. Similar results were obtained with the MCF7-GFP cancer cell line, for example, in FIG. 4C, which confirm the viability and versatility of the hybrid DNA-nanomotor-based silencing strategy. In view of the example results shown in FIG. 4B, graph (c) and FIG. 4C, graph (c), it can be said that the major advantage of the nanomotor-based siRNA delivery approach is the accelerated silencing response, with both cell lines reaching a silencing % plateau after 5 hours nanomotor treatment.

Figure 5A:
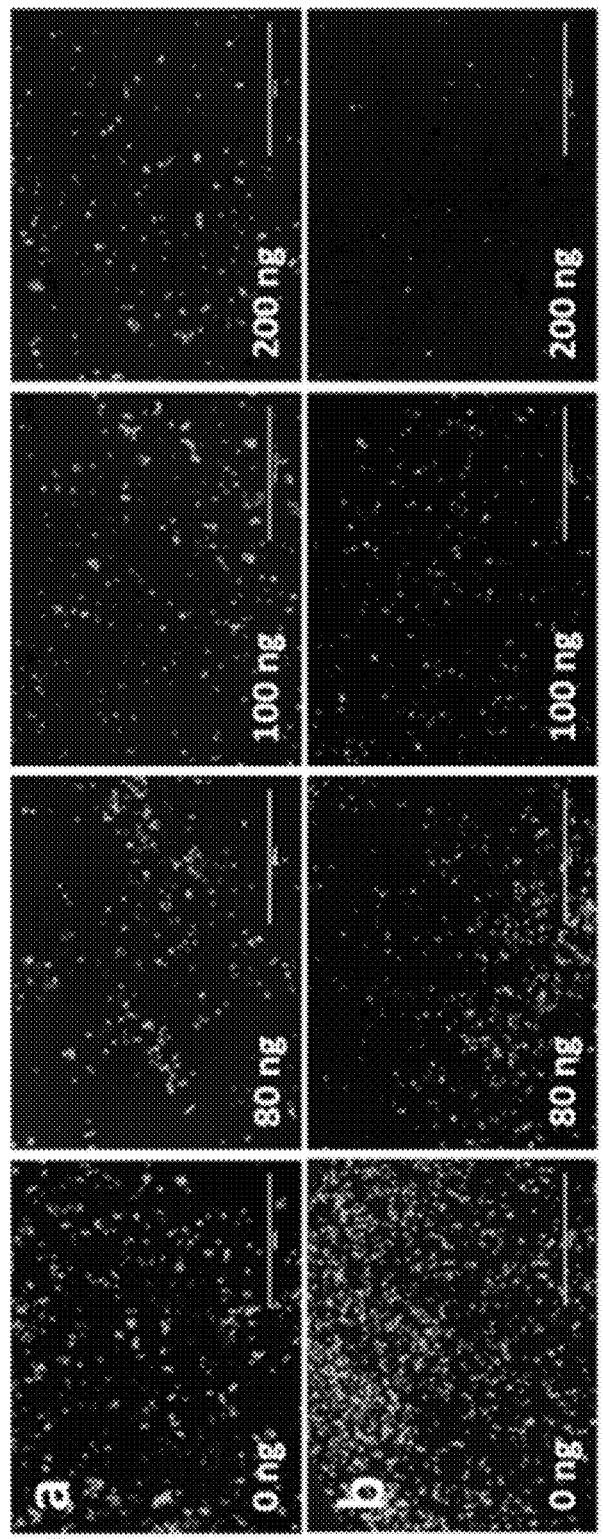
FIGS. 5A and 5B show images and graphs from example siRNA dosage studies.
Figure 5A:
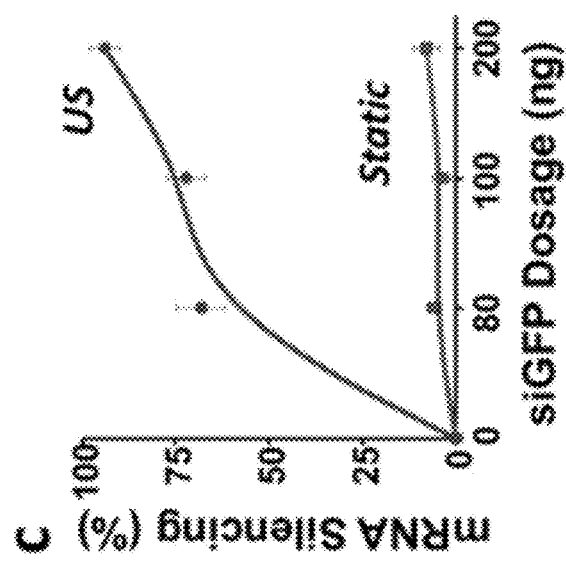
Figure 5B:
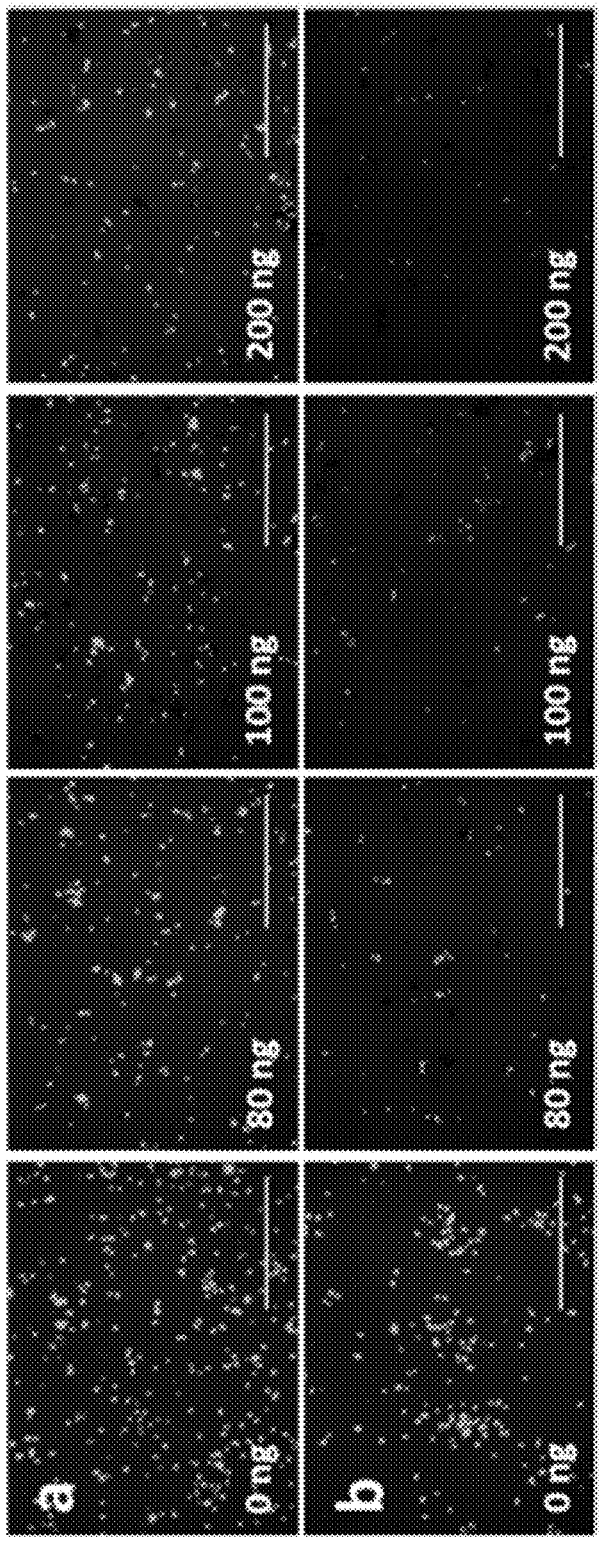
Figure 5B:
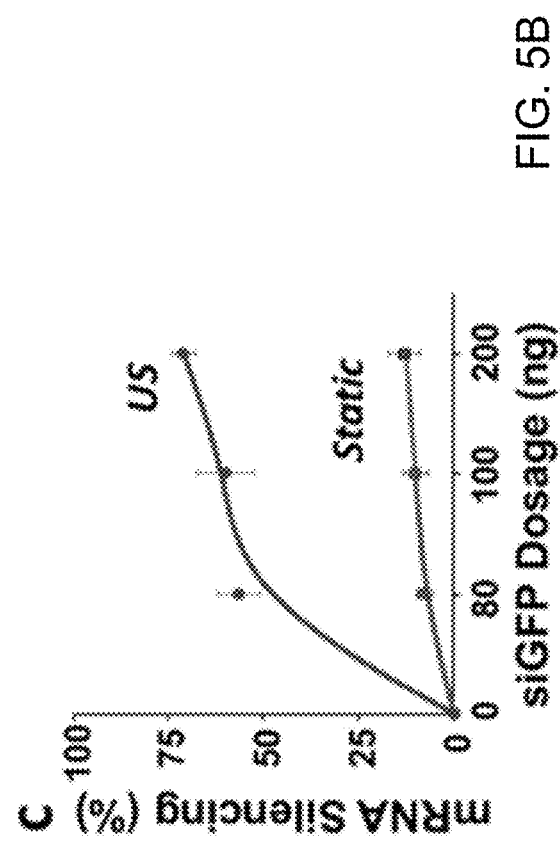

FIGS. 5A and 5B show images and data plots depicting results from example implementations that demonstrated further improvement of the silencing effect including modifying the siGFP dosage for enhancing the amount of intracellular siRNA. The example images depict the effect of the amount of siGFP (e.g., 0, 80, 100 and 200 ng) immobilized on the gold nanowires onto the efficiency of the gene-mRNA silencing inside HEK293-GFP cells (FIG. 5A) and MCF7-GFP cells (FIG. 5B), using static conditions (image panel (a)) and US-propelled micromotors (image panel (b)). The graphs shown in plots (c) of FIGS. 5A and 5B illustrate the dependence of the mRNA silencing % in both cell lines upon the GFP/RCA dosage (ng) in the absence and presence of the US field, respectively, with ultrasound parameters at 6V, 2.66 MHz, 5 min.

For the example implementations of FIGS. 5A and 5B, a concentrated RCA-siRNA product was synthesized to modify the motors, and was then diluted according to the desired dosage (e.g., 0, 80, 100 or 200 ng). Subsequently, both cell lines were treated with motors loaded with different dosages of siGFP (siRNA dosages), and the silencing effect between static and US propulsion conditions was compared (FIGS. 5A and 5B: image panel (a) vs image panel (b)). For example, using US-propelled motors, the silencing response of HEK293-GFP cells increased from a 68% to a 94% upon raising the dosage from 80 ng to 200 ng of siGFP, respectively (FIG. 5B, graph (c)). In contrast, for example, static conditions resulted in a significantly lower change of the silencing percentage (e.g., 6% to 12%) over the same 80-200 ng GFP/RCA dosage range (FIG. 5A, graph (c)). As illustrated in FIG. 5A graph (c), loading the nanomotors with 100 ng of the siRNA/RCA template and propelling them for 5 min, resulted in ~13 fold higher silencing compared to the static wires. For example, such major improvement reflects the efficient siRNA delivery associated with the fast internalization of the motor and rapid intracellular movement under the US field. Similar silencing responses were observed with the MCF7-GFP cancer cell line (FIG. 5B), e.g., demonstrating a 70% silencing when using US-propelled nanomotors loaded with 200 ng of the siRNA/RCA template, compared to the 13% silencing obtained with static nanorods (FIG. 5 B, graph (c)). Overall, the example results presented in FIGS. 5A and 5B demonstrate clear advantages of speed and efficiency of the example nanomotor mRNA-gene silencing approach in terms of knockdown method in both cell lines, e.g., which make it a competitive gene-delivery platform for the treatment of various diseases.

The example implementations included studies to exclude the possibility that the silencing of GFP signal comes from the death of cells. For example, cell viability was examined after the different treatments with static and US-propelled nanomotors, e.g., choosing the MCF7-GFP as the model cell line. The example results obtained indicated that neither the non-modified AuNWs nor the siGFP/RCA-AuNWs (using different GFP/RCA dosages), affected significantly the cell viability. These example findings are in good agreement with earlier reports that indicate that the presence of micro/nanomotors does not exhibit acute toxicity towards the cells. These example data demonstrate that after the nanomotors-treatment, the cells were still alive, but had specifically reduced their expression of the target protein.

Figure 6A:
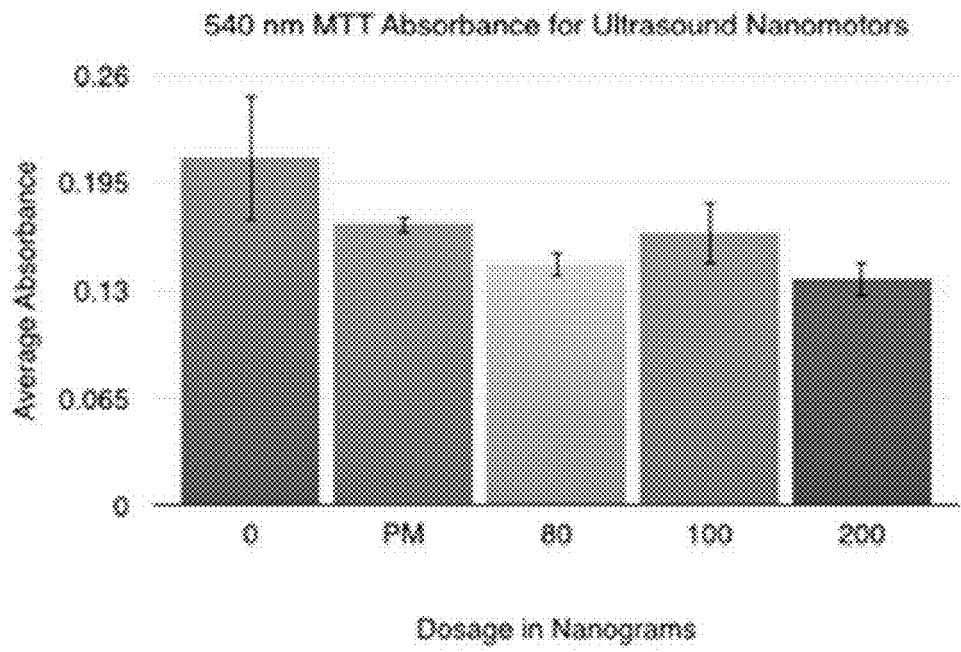
FIGS. 6A and 6B show data plots depicting example results of a cell viability test.
Figure 6B:
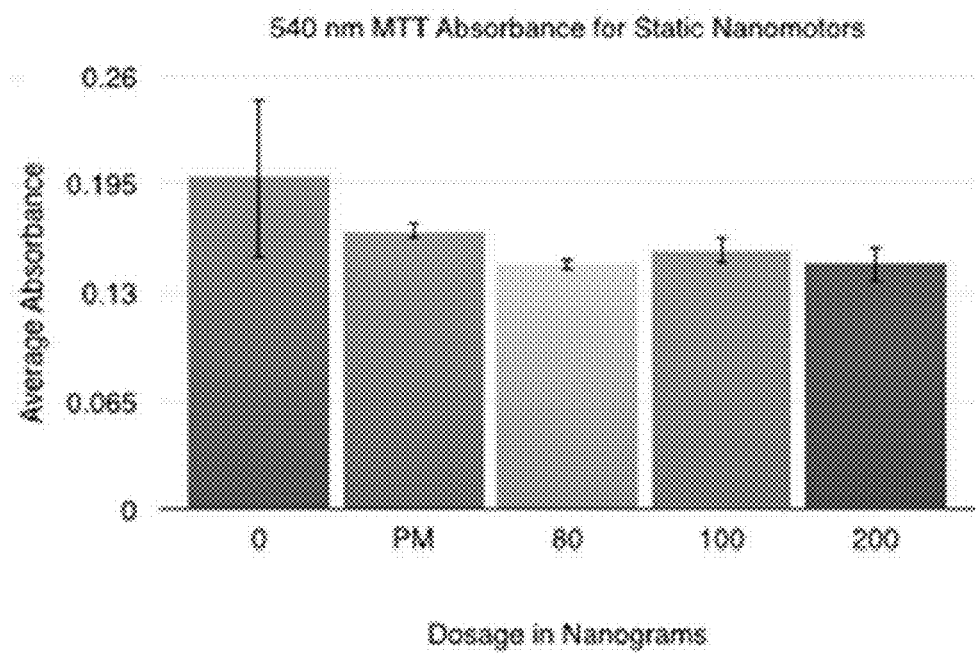

FIGS. 6A and 6B shows data plots depicting example results of a cell viability test. The graphs correspond to the average absorbance at 540 nm using an MTT assay across three wells of MCF-7-GFP cells treated with GFP/RCA-modified nanomotors propelled by ultrasound (FIG. 6A) and static GFP/RCA-modified nanomotors (FIG. 6B). The experimental conditions included GFP/RCA dosage: 0, 80, 100 and 200 ng; and ultrasound conditions: 6 V, 2.66 MHz and 5 min; and "PM" stands for plain nanomotors. The detailed mechanism of this rapid GFP silencing is believed be enhanced by the nanomotors movement within the cells. For example, compared with commonly used delivery cargos, such as lipid nanoparticles, which take a few hours for cell uptake and endosome escape, the disclosed acoustically-propelled nanowires enter the cell rapidly (with few minutes) and travel inside it. The spinning motion inside the cells accelerates the siRNA's release and diffusion at multiple locations, and thus leads to a faster mRNA silencing.

Example methods for fabrication and implementations of the siGFP/RCA DNA-modified gold nanowires are described below.

Example reagents, cells and solutions used in the example implementations included the following. Cysteamine hydrochloride was obtained from Sigma-Aldrich. RCA products were obtained from Core Bio Services. Phosphate buffered saline (PBS) solution was obtained from Gibco, Invitrogen.

Human Embryonic Kidney 293 cells imaged with Green Fluorescent Protein (HEK293-GFP) and Michigan Cancer Foundation-7 (MCF7-GFP) were obtained from the University of California-San Diego (UCSD), Nanomaterials & Nanomedicine Laboratory. The cell lines were grown in Corning cellular DMEM media with 4.5 g/L glucose, L-glutamine, and sodium pyruvate obtained from Fisher Scientific, 10% Hylcone Bovine Growth Serum (FBS) obtained from VWR International, and 1% penicillin streptomycin obtained from Core Bio Services and the cells were used immediately for the experiments. To prepare the cells suspension, after removing the cell culture media, cells were detached from the flask by treating them with 2 mL of Trypsin-EDTA (0.25%), obtained from Core Bio Services, for 2 minutes. The trypsin was then inactivated using the supplemented media, centrifuged for 5 minutes at 0.7 RCF and resuspended to the correct concentration in media using a hemocytometer. Milli-Q water was used for the modification step of AuNWs with cysteamine. PBS solution pH 7.5, prepared with Milli-Q water, was used for during the incubation of the cysteamine-modified AuNWs and siRNA samples, to perform the washing steps and during the US experiments. Chemicals used were of analytical-grade reagents, and deionized water was obtained from a Millipore Milli-Q purification system (e.g., 18.2 MΩ cm at 25° C.).

Synthesis of RCA in the example implementations included the following. DNA sequences were obtained from Integrated DNA Technologies. The circle strand (Circle-20A) and the primer strand (Primer-Poly-T) were ligated together in a 1:10 molar ratio using 148 µL of quick ligation buffer, 150 µL of DI water, and 15 µL of quick ligase for at least 16 hours at 14° C. 2 picomoles of the ligated circle was combined with the nucleotides (e.g., 12 µL-120 nmoles of dNTPS), water (up to 60 µL), the polymerase buffer (e.g., 6 µL), bovine serum albumin (1.6 µL of 10 mg/mL), and the polymerase (e.g., 3 µL-30 units). This example procedure reaction for 2 hours at 37° C. and then the polymerase was inactivated at 70° C. for 10 minutes. The GFP sense and antisense strands were combined in an equimolar ratio and diluted to 1 µg/µL using water and 10×TAE Mg diluted to a 1× concentration in the final volume. 1.5 µg of GFP siRNA was added to 30 µL of RCA product and 3.44 µL of 10× TAE Mg. This was annealed using an annealing program titled the "native 30" program using an Eppendorf Mastercycler (e.g., hold for 5 minutes at 90° C., ramp down to 65° C., hold for 30 minutes, ramp down to 50° C., hold for 30 minutes, ramp down to 37° C., hold for 30 minutes, and then ramp down to 22° C. and hold).

Table 1 show oligonucleotide sequences used in the example implementations of the siGFP/RCA DNA-modified gold nanowires.

TABLE 1

(SEQ ID NOS 1-6, respectively)

| Oligonucleotide | Sequence (5'→3') |
|---|---|
| Circle-20A | 5'-/phos/ATACATACATA AAA AAA AAA AAA AAA AAA AA-3' |
| Primer-polyT | 5'-TATGTA TTT TTT TT-3' |
| Sense-GFP-20A | 5'-rArCrArUrGrArArGrCrArGrCrArCr GrArCrUrTTT AAA AAA AAA AAA AAA AAA AA-3' |
| Antisense-GFP | 5'-rArArGrUrCrGrUrGrCrUrGrCrUrUr CrArUrGrUTT-3' |
| Sense-Luc | 5'-rCrUrUrArCrGrCrUrGrArGrUrArCr UrUrCrGrATT-3' |
| Antisense-Luc | 5'-rUrCrGrArArGrUrArCrUrCrArGrCr GrUrArArGTT AAA AAA AAA AAA AAA AAA AA-3' |

Synthesis of concentrated RCA for dosage experiments in the example implementations included the following. Six times the normal volume of RCA was created and then the phi29 polymerase was deactivated at 70° C. for 35 minutes. The DNA was precipitated out of solution using ethanol precipitation and then resuspended in 50 µL of 18.2 MΩ cm water, 6.66 µL of 10× TAE Mg, and 10 µg of 1 µg/µL GFP siRNA. This was annealed using the native 30 program. Once annealed, the RCA/GFP was combined with the nanomotors and diluted according to the desired dosage.

Characterization of GFP/RCA in the example implementations included the following. The morphology of the RCA strand with and without the siRNA was analyzed by AFM (Credit Sibai Xie). AFM imaging was performed under room temperature in dry condition. 3 µL sample DNA solution was dropped onto freshly cleaved mica surface, and incubate at room temperature for 1-2 min for surface adsorption. The drop was washed off by 30 µL 2 mM Mg(Ac)2 solution, and was dried by compressed air. Scanasyst-Air tip (Bruker, Camarillo, Calif.) with a spring constant of 0.4 N/m was used on a Multimode AFM (Vecco Metrology, Santa Barbara, Calif.). Amplitude setpoint was controlled at the lowest possible value to avoid scratching on the structure.

A 0.5% native TBE agarose gel was performed to confirm the binding of the siRNA to the RCA product as well. The gel was stained with 0.01% ethidium bromide in the gel before running at 100V for 1 hour and 20 minutes in 1× TBE buffer and exposed to ultraviolet light for imaging.

For implementations using Lipofectamine 2000, for example, 200 µL of OPTI-MEM was combined with 0.8 µg of 'native 30' annealed 1 µg/µL GFP siRNA and 5 µL of Lipofectamine 2000. Approximately, $7 \times 10^3$ cells were seeded in a 96 well plate and incubated overnight at 37° C. The media was removed and each well was treated with 80 ng of the GFP siRNA with the Lipofectamine 2000 and additional media. After 18 hour incubation at 37° C., the wells were imaged using the EVOS FL microscope. The Lipofectamine used in the dosage experiment was prepared in the same method, by increasing the amount of siRNA added into the original mixture.

Nanomotors fabrication in the example implementations included the following. The gold nanowire (AuNWs) motors were prepared by a common template-directed electrodeposition protocol. A thin gold film was first sputtered on one side of the porous alumina membrane template containing 200-nm diameter cylindrical nanopores to serve as a working electrode. The membrane was assembled in a Teflon plating cell with aluminum foil serving as an electrical contact for the subsequent electrodeposition. A sacrificial copper layer was electrodeposited into the branched area of the membrane using a 1 M cupric sulfate pentahydrate solution ($CuSO^4.5H_2O$), using a charge of 8 C and a potential of −0.90 V (vs a Ag/AgCl reference electrode, along with a Pt-wire as a counter electrode). The removal of this sacrificial layer helps to create the concave shape in one end of the gold wire motor. Subsequently, Au was plated using a gold plating solution (Orotemp 24 RTU RACK; Technic Inc., Anaheim, Calif.) at −1 V (vs Ag/AgCl), using a charge of 4 C. The resulting AuNWs had a length of around 4 μm. The sputtered gold layer and the copper sacrificial layer were simultaneously removed by mechanical polishing using cotton tip applicators soaked with 0.5 M $CuCl_2$ solution in 20% HCl. The membrane was then dissolved in a 3 M NaOH solution for 30 min to completely release the nanowires. The resulting nanomotors were separated from solution by centrifugation at 7,000 rpm for 5 min and washed repeatedly with ultrapure water (18.2 MΩ cm) until a neutral pH was achieved. Between washing steps, the nanomotors solution was mixed with ultrapure water and briefly sonicated (2-5 seconds) to ensure complete dispersion of nanomotors in the washing water. AuNWs were stored in 1 mL of ultrapure water at room temperature.

Nanomotors modification in the example implementations included the following. The external gold surface of the AuNWs was modified by an overnight immersion in a 2 mM cysteamine hydrochloride solution prepared in water, to obtain an appropriate self-assembly monolayer (SAM). After washing with ultrapure water (by centrifugation at 7,000 rpm for 5 min), the cysteamine-modified AuNWs were incubated with the corresponding sample during 1 h under gently shaking. After another washing step with ultrapure water, the GFP/RCA-modified ANWs were washed twice with PBS solution pH 7.5. Incubation steps were carried out at room temperature. Also, for example, AuNWs were prepared using the same protocol to perform the corresponding control experiments.

In vitro intracellular mRNA silencing in the example implementations included the following. The intracellular mRNA silencing mechanism involved the knockdown of the mRNA target by the siRNA (GFP/RCA) immobilized on the motors surface. To determine the percentage of mRNA silencing in intact HEK293-GFP cells, a mixture of 2 μL of the cell suspension (e.g., ~1750 cells/μL) and 2 μL of the GFP/RCA-AuNWs was prepared and put into the US holder, applying 6V and 2.66 MHz during 5 min. After each study, the total volume (e.g., ~7.0×10³ cells) of the mixture solution was placed in a well containing Corning cellar DMEM media with 4.5 g/L glucose, L-glutamine, and sodium pyruvate, 10% Hylcone Bovine Growth Serum (FBS), and 1% penicillin streptomycin, and incubated at 37° C. for 24 h. Each well was imaged using an EVOS fluorescent cell imaging system. Also, for the study of the fluorescence signal dependence upon the incubation time under static or US conditions, the fluorescence signal of each sample (static conditions or US) was checked in the microscope after different times (0, 30, 120 min and 5, 15 h). The experiments were carried out at room temperature.

Videos were captured using Cool SNAP $HQ^2$ camera, 20× and 40× objectives (unless mentioned otherwise) and acquired at the frame rate of 10 using the Metamorph 7.1 software (Molecular Devices, Sunnyvale, Calif.). A Nikon Eclipse 80i upright microscope with AT-GFP/F LP filter was used to capture fluorescence images and videos. The fluorescence intensities were estimated by analyzing the corresponding time lapse images using the software ImageJ.

Ultrasound equipment used in the example implementations included the following. The acoustic cell setup included a piezoelectric transducer (e.g., Ferroperm PZ26 disk 10 mm diameter, 0.5 mm thickness) responsible for the generation of ultrasound waves, attached by conductive epoxy glue to the bottom center of a steel plate (50 mm×50 mm×0.94 mm); then the steel plate was covered with a 240 μm kapton tape protective layer and a sample reservoir at the center (e.g., 5 mm). A glass slide was used to cover the reservoir for ultrasound reflection and to protect the sample. The continuous ultrasound sine wave was applied via a piezoelectric transducer, through an Agilent 15 MHz arbitrary waveform generator, in connection to a home-made power amplifier. The applied continuous sine wave form had a frequency of 2.66 MHz and voltage amplitude, which varied between 3 and 9 V, to modulate the intensity of the acoustic wave.

Cell viability assays in the example implementations included the following. Cell viability testing was conducted using MTT (3-(4,5-dimethylthiazolyl-2)-2,5-diphenyltetrazolium bromide) cell viability reagent to evaluate the effect of the acoustic exposure. After 20 hours of cell incubation, the media from the wells was removed and replaced with 110 μL of a mixture of 100 μL of DMEM with 10% FBS and 1% PST and 10 μL of the Biotium MTT assay kit. This work was performed in a hood without the light turned on due to the light sensitive nature of MTT. The 96 well-plate was then incubated for 4 hours at 37° C. The MTT mixture was then carefully removed using a small needle, replaced with 100 μL of DMSO, and then incubated for 10 minutes at 37° C. The absorbance was then read from 540 nm to 580 nm.

Table 2 shows example results of analysis of cells under ultrasound and static conditions. The percentage of viability was calculated assuming that the average absorbance of the wells containing pure cells represented 100% viability. Subsequent t-values were obtained by performing two-tailed, paired T-tests between each set of wells and the cells themselves. From these t-values, p-values have been calculated. In the example cases, the p-values showed that a significant difference between the pure cells and the treated samples could not be stated.

TABLE 2

|  | 200 | 100 | 80 | PM | cells |
|---|---|---|---|---|---|
| Ultrasound (540 nm) | | | | | |
| Well 1 | 0.147 | 0.154 | 0.153 | 0.166 | 0.234 |
| Well 2 | 0.127 | 0.185 | 0.143 | 0.175 | 0.23 |
| Well 3 | 0.137 | 0.152 | 0.14 | 0.167 | 0.166 |
| Average | 0.1370 | 0.1637 | 0.1453 | 0.1603 | 0.2100 |
| Standard Deviation | 0.0100 | 0.0185 | 0.0068 | 0.0049 | 0.0382 |
| Percent | 65.24 | 77.94 | 69.21 | 76.35 | 100.00 |
| T-Test | 0.0832 | 0.1357 | 0.0795 | 0.1947 | |
| P-Value | 0.9472 | 0.9142 | 0.9495 | 0.8644 | |
| Static (540 nm) | | | | | |
| Well 1 | 0.152 | 0.146 | 0.148 | 0.172 | 0.25 |
| Well 2 | 0.154 | 0.162 | 0.15 | 0.162 | 0.155 |
| Well 3 | 0.135 | 0.158 | 0.143 | 0.165 | 0.191 |
| Average | 0.1470 | 0.1553 | 0.1470 | 0.1663 | 0.1987 |
| Standard Deviation | 0.0104 | 0.0083 | 0.0036 | 0.0051 | 0.0480 |
| Percent | 73.99 | 78.19 | 73.99 | 83.72 | 100.00 |
| T-Test | 0.2072 | 0.3135 | 0.2069 | 0.3213 | |
| P-value | 0.8700 | 0.8066 | 0.8701 | 0.8021 | |

The example synthetic nanomotors functionalized with nucleic acids in accordance with embodiments of the present technology are envisioned to provide a powerful therapeutic option for siRNA delivery that greatly enhances intracellular gene delivery, as compared to existing gene-silencing methods. Example implementations of example motile nano- and microstructures for active and dynamic intracellular payload delivery in accordance with the present technology have shown that siGFP/RCA modified-gold nanowires can be propelled rapidly into different cell lines and can dramatically accelerate the siRNA delivery and gene-mRNA silencing compared with static nanowires. Up to a 94% silencing was observed after 5 min treatment with US-propelled siRNA/RCA-modified nanomotors and HEK293-GFP cells, for example. The example nanomotors were shown to undergo fast internalization and rapid intracellular movement, along with the large siRNA payloads. The latter relies on creating DNA siGFP/RCA nanostructures on the motor surface. In some implementations, the RCA template can be modified to contain different binding regions to allow for the quantitative co-delivery of multiple types of siRNA that are associated with various cancer phenotypes. Cell viability tests indicate no significant cell damage after the acoustic nanomotors treatment, even when using high nanomotor concentration. Using the localization ability of ultrasound, this nanomotor-driven platform can address the challenge of targeted delivery in vivo. Accordingly, it is envisioned that the new micromotor-based gene-silencing strategy will find considerable interest in the fields of cancer biology, drug development, functional genomics, and nanomedicine.

Example Implementations of Nanomotors for Intracellular Cas9/sgRNA Complex Delivery In some embodiments of the nanomotors in accordance with the present technology, ultrasound-propelled nanomotors are described for direct and active intracellular delivery of Cas9-sgRNA complex. In example implementations, a Cas9-sgRNA complex is loaded onto the nanomotors' surface through a reversible disulfide linkage. For example, a 5-min ultrasound treatment enabled the Cas9-sgRNA-loaded nanomotors to directly penetrate through the plasma membrane of GFP-expressing B16F10 cells. The carried Cas9-sgRNA payload was released inside the cells achieving highly effective GFP-gene knockout. For example, the acoustic Cas9-sgRNA-loaded nanomotors displayed more than 80% GFP-knockout within 2 h of cell incubation compared to 30% knockout using static nanowires. Also, for example, the nanomotors enabled high-efficient knockout with just 0.6 nM of the Cas9-sgRNA complex. This nanomotor-based intracellular delivery method thus offers an attractive route to overcome physiological barriers for intracellular delivery of functional proteins and RNAs, indicating considerable promise for highly efficient therapeutic applications.

Clustered Regularly Interspaced Short Palindromic Repeats (CRISPR)-associated protein 9 (Cas9) has become an attractive tool to perform genomic editing due to its versatility, efficiency, and accuracy. The ribonucleic acid (RNA)-guided endonuclease complex enables effective genome editing, which has been demonstrated by the production of transgenic cellular and animal models, genome-wide function screening, transcriptional modulation, epigenetic control, and intracellular genome imaging. The Cas9 nuclease needs to complex with a CRISPR RNA (crRNA) and a trans-activating crRNA (tracrRNA) to selectively target a gene and thereby achieve site-specific DNA cleavage. Practically, crRNA and tracrRNA have been fused into a single guided RNA (sgRNA), which can effectively programme Cas9 in guiding targeted gene alterations.

Numerous approaches have been developed for intracellular delivery of Cas9-sgRNA complex. For instance, a plasmid DNA encoding the Cas9-sgRNA complex can be transduced into target cells through electroporation, nucleofection, transfection, hydrodynamic injection, or viral vectors-mediated delivery approaches. The delivered plasmid DNA subsequently expresses and produces Cas9-sgRNA for intracellular gene editing. On the other hand, different nanomaterials such as lipid- and polymer-based nanoparticles have been utilized to directly deliver Cas9-sgRNA into cells following similar paths and challenges as common drug delivery technologies. While these approaches are promising in general, it remains elusive to achieve highly effective and efficient Cas9-sgRNA complex intracellular delivery.

Example embodiments of the disclosed nanomotor structures, devices, systems and methods in accordance with the present technology provide an attractive design for Cas9-sgRNA complex intracellular delivery. Herein, example methods and results of a nanomotor-based approach for active and direct intracellular delivery of Cas9-sgRNA complex are described. For these example implementations, the Cas9-sgRNA complex was immobilized onto the surface of thiol-functionalized gold nanowires (AuNWs) through a reversible disulfide linkage via cysteine residues within Cas9. The active and fast movement of these Cas9-sgRNA/AuNWs under an ultrasound field facilitates their rapid internalization into the cytoplasm of green fluorescent protein (GFP)-expressing B16F10 cells. Once inside the cells, the Cas9-sgRNA payload is released autonomously from the nanomotor surface, mediated by the high intracellular concentration of glutathione (GSH) in tumor cells. The ribonucleoprotein (RNP) is then transported to the nucleus by an encoded nuclear localization sequence to initiate the specific cleavage of the GFP genomic sequence. Compared to conventional methods for direct cytosolic delivery of Cas9-sgRNA, as shown in Table 3, the disclosed nanomotor-based approach is able to overcome physical barriers and rapidly deliver functional Cas9-sgRNA complex into cells, enabling fast and efficient genome editing inside the target cells. Overall, these example findings demonstrate considerable promise for using the acoustic nanomotors in accordance with the present technology as dynamic vehicles for direct and efficient intracellular delivery of a fully functional Cas9-sgRNA complex.

Figure 7:
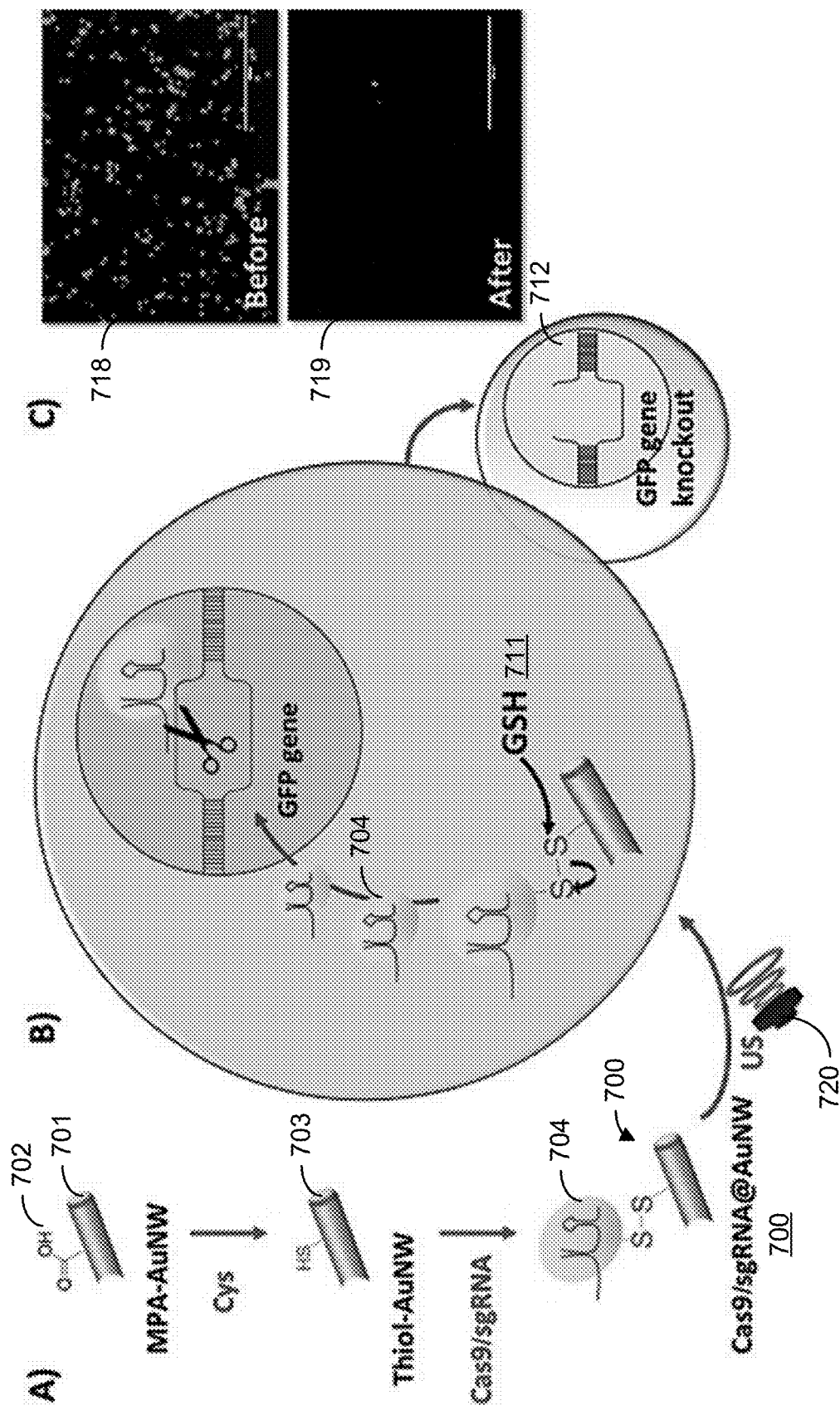
FIG. 7 shows an illustrative diagram depicting the preparation and implementation of example nanomotor delivery device for intracellular delivery of an active Cas9-sgRNA complex payload for gene therapy in accordance with the present technology.

FIG. 7 illustrates an example nanomotor modification method for the loading of Cas9-sgRNA complex. The left region (A) of FIG. 7 illustrates the surface modification and loading of Cas9-sgRNA complex 704 onto the surface of a gold nanowire (AuNW) motor 701 to produce a Cas9-sgRNA-modified AuNW motor 700; the middle region (B) of FIG. 7 illustrates US-mediated intracellular delivery of Cas9-sgRNA complex and subsequent cytosolic release mediated by the intracellular reducing environment inside GFP-B16F10 cells; and the right portion (C) of FIG. 7 shows fluorescent images of the GFP-B16F10 cells before and after treatment with US-propelled Cas9-sgRNA-modified AuNWs 700. The scale bars of the images are 400 μm.

Initially, the Cas9-sgRNA complex 704 was formed through a complexation between Cas9 protein and sgRNA oligomer, in which the sgRNA was designed for specific recognition of a GFP genomic sequence (Table 4). The gold nanowires 701 were functionalized with a self-assembled monolayer of 3-mercaptopropionic acid (MPA) 702, introducing a carboxylic acid surface moiety for further modification with cysteine through an amide bond formation, e.g., amide-functionalized AuNWs 703. The Cas9-sgRNA complex 704 was then immobilized onto the surface of the amide-functionalized AuNWs 703 through a disulfide linkage between the thiol groups on the AuNWs and the cysteine on the Cas9 protein, producing the Cas9-sgRNA-modified AuNW motor 700.

As depicted in the middle region (B) of FIG. 7, the fully functional gene editing Cas9-sgRNA-modified AuNW motor 700 enters the GFP-expressing melanoma B16F10 cells upon application of acoustic energy by an ultrasound system 720 (e.g., 5 min ultrasound-treatment). The high level of intracellular glutathione (GSH) 711, characteristic of tumor cells, facilitates the release of Cas9-sgRNA payload 704 from the nanomotor surface through the disulfide reduction or ligand exchange. The released Cas9-sgRNA payload 704 can thus enter the nucleus to initiate site-specific gene editing for GFP knockout, to create a silenced gene 712. The knockout effect with "turn-off" fluorescence can be directly observed by using time-resolved fluorescent microscopy, as shown by images 718, 719 in region (C) of FIG. 7.

Figure 8A:
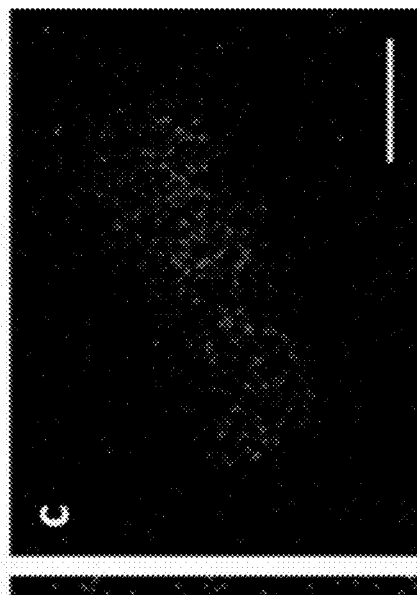
FIGS. 8A-8B show images and data plots depicting example structural and propulsion characterizations of Cas9-sgRNA modified gold nanowire motors in cells.
Figure 8A:
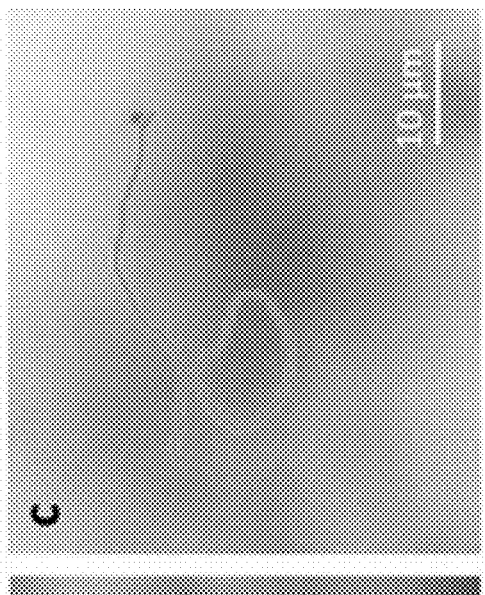
Figure 8B:
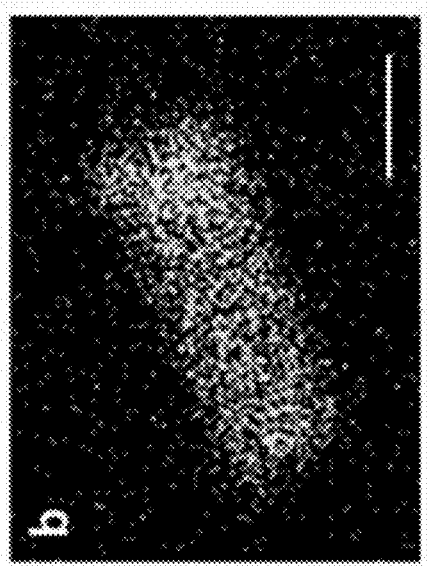
Figure 8B:
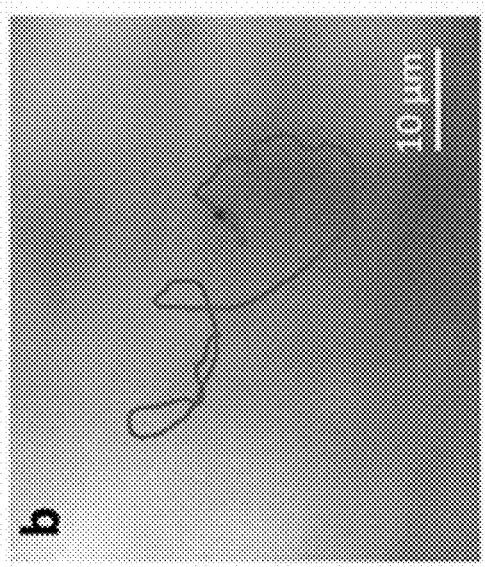
Figure 8B:
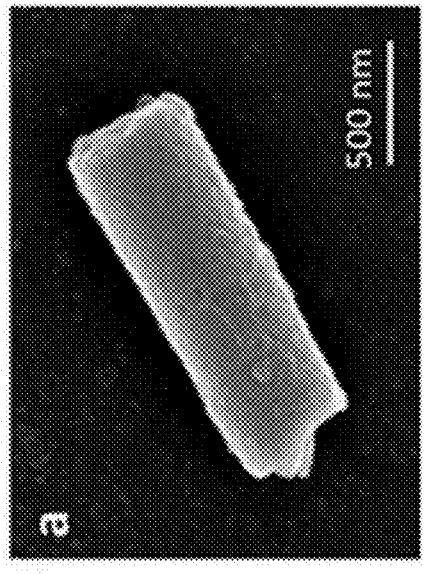
Figure 8B:
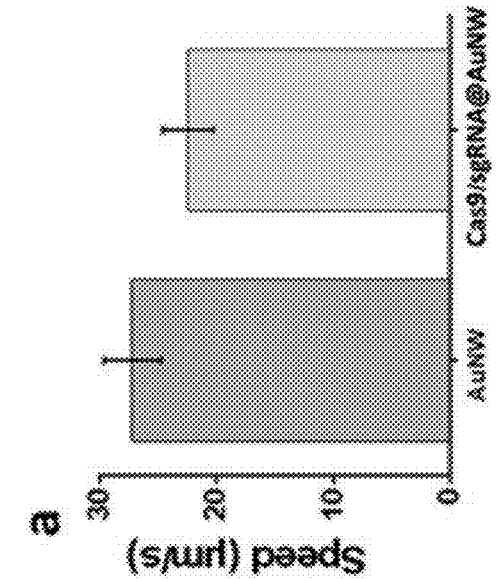

FIGS. 8A-8B show images and data plots depicting example structural and propulsion characterizations of the example Cas9-sgRNA-modified AuNWs 700. FIG. 8A shows SEM and corresponding EDX analysis of the Au and N content of an example Cas9-sgRNA-modified Au nanowire motor (images (a)-(c), respectively). FIG. 8B shows a data plot and images providing a comparison of the propulsion of non-modified gold nanowire motors (red, left bar of graph (a) and image (b)) and Cas9-sgRNA-modified AuNWs (green, right bar of graph (a) and image (c)) under an ultrasound field (e.g., 1.6V, 2.66 MHz). The bar plot (a) of FIG. 8B represents the mean and standard deviation of three independent measurements, and time-lapse images were taken to track trajectories of a non-modified motor (image (b)) and a Cas9-sgRNA-modified nanomotor (image (c)) under the ultrasound field.

Scanning electron microscopy (SEM) imaging was carried out to examine the structural morphology of the Cas9-sgRNA-modified AuNWs 700. As shown in image (a) of FIG. 8A, the SEM image displays the structure of the example Cas9-sgRNA-modified AuNW motor with a diameter of 400 nm and a length of ~2 µm. The AuNW motor was engineered to have an asymmetric shape to achieve acoustic propulsion. Energy dispersive X-ray spectroscopy (EDX) mapping was also performed (images (b) and (c) of FIG. 8A), which confirmed the presence of Au and N, corresponding to the nanomotor core and the immobilized Cas9-sgRNA payload, respectively. Further EDX analysis confirmed the successful modification of the AuNW motors with the Cas9-sgRNA complex, as displayed by the phosphorus content of the motors, corresponding to the phosphate backbone of the RNA sequence.

The propulsion performance of the Cas9-sgRNA-modified AuNWs under an ultrasound field was compared to that of the non-modified AuNWs (e.g., without Cas9-sgRNA). As shown by the bar plot (a) and corresponding time-lapse images (b) and (c) of FIG. 8B, the Cas9-sgRNA-modified AuNWs displayed efficient US-propulsion (e.g., ~22 µm/s), for example, exhibiting only a slight speed decrease compared to the non-modified AuNWs (e.g., ~26 µm/s). These results indicate that the loaded Cas9-sgRNA complex only has a small effect upon the motor propulsion. Such movement leads to effective motor penetration through the cell membrane for efficient internalization and delivery of the Cas9-sgRNA complex.

Figure 9A:
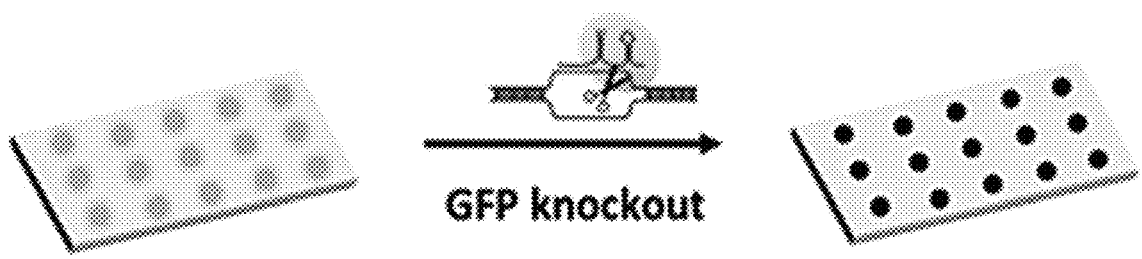
FIGS. 9A-9D show illustrations, images and data plots depicting the effect of treatment time on the knockout efficiency for the GFP-B16F10 cells treated at different conditions of the example Cas9-sgRNA-modified gold nanowire motors.
Figure 9B:
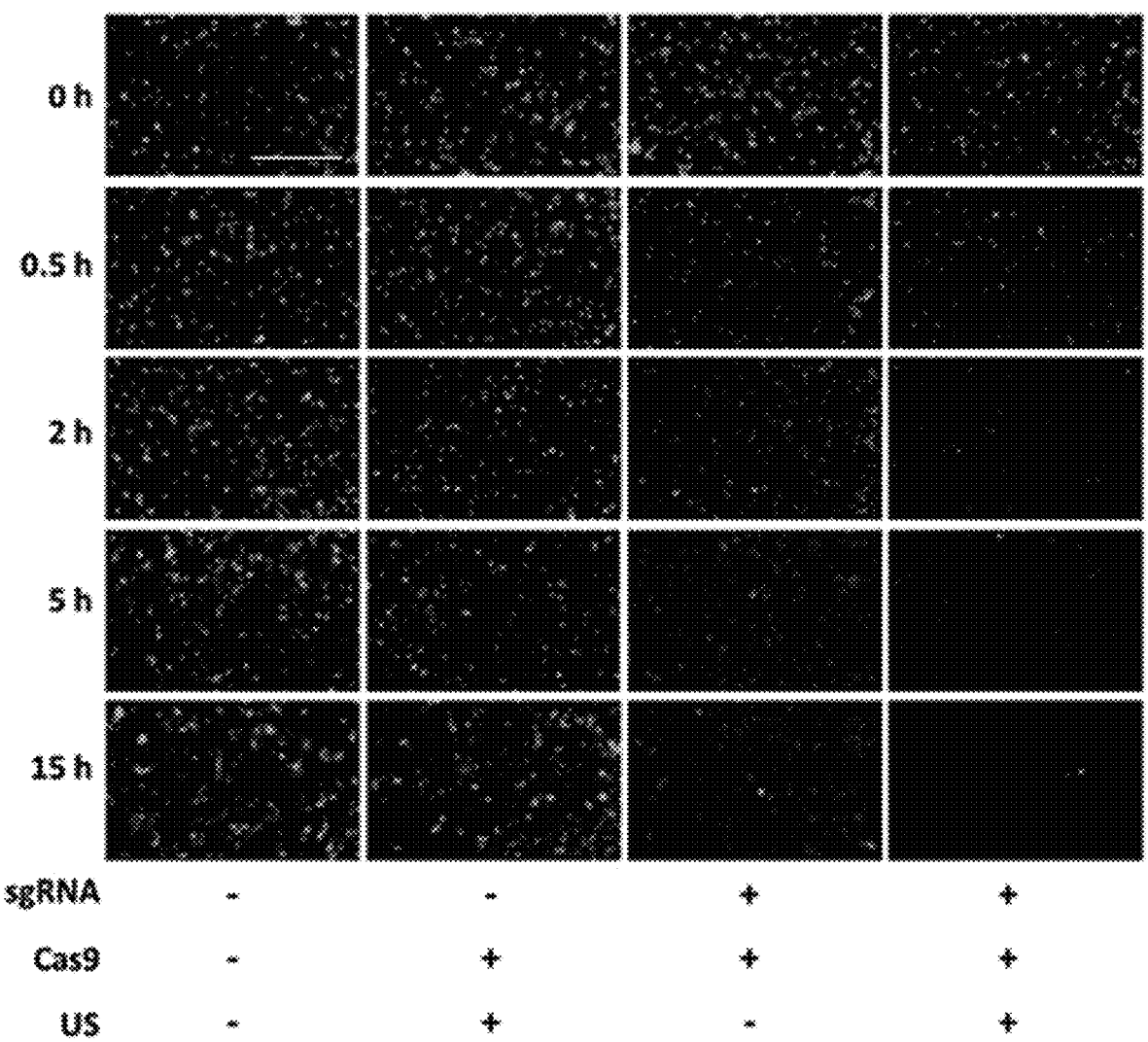
Figure 9C:
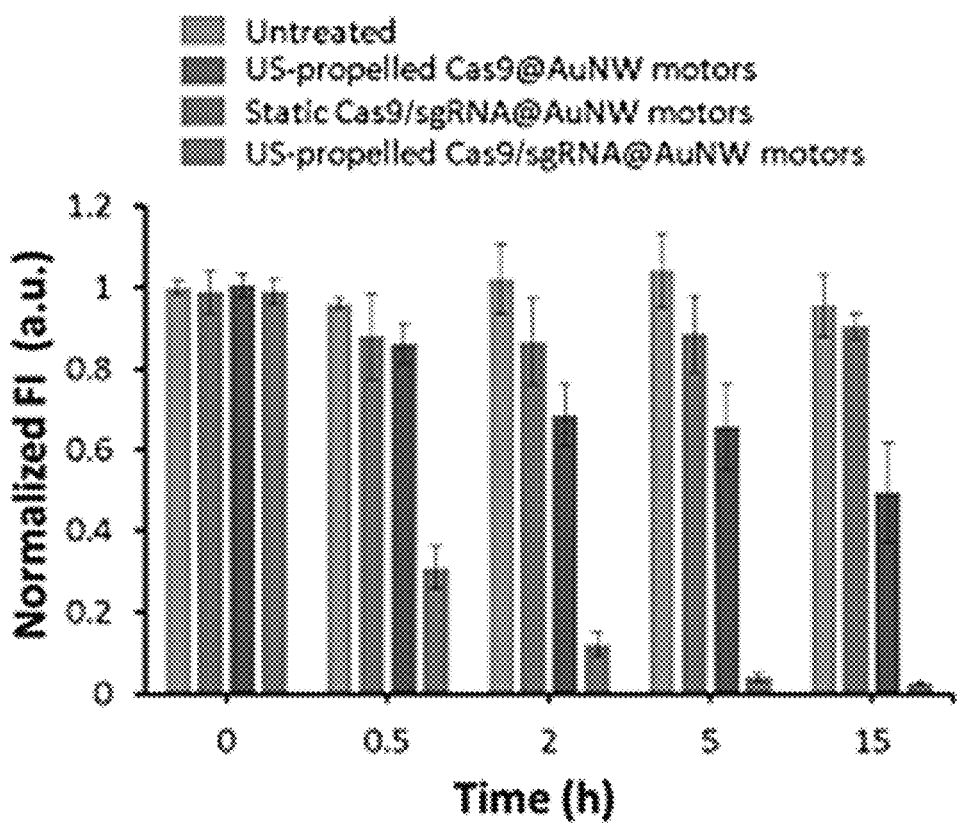
Figure 9D:
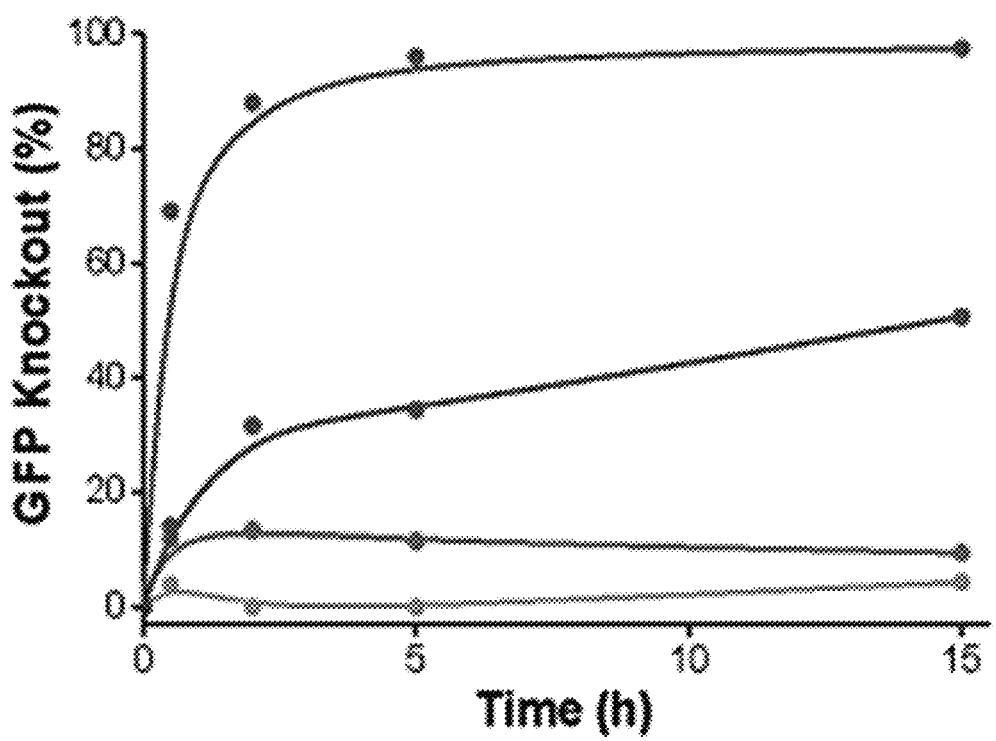

FIGS. 9A-9D show illustrations, images and data plots depicting the effect of treatment time on the knockout efficiency for the GFP-B16F10 cells treated at different conditions of the example Cas9-sgRNA-modified AuNWs 700. FIG. 9A shows an illustrative diagram depicting the GFP knockout (e.g., representation of GFP-B16F10 cells grown on a well-plate) using US-propelled Cas9-sgRNA-modified AuNWs. The GFP gene can be knocked out by delivering Cas9-sgRNA complex with the ultrasound-propelled motors, which 'turns off' the GFP-B16F10 cells fluorescence. FIG. 9B shows fluorescence images of (left to right) untreated GFP-B16F10 cells, GFP-B16F10 cells treated with US-propelled Cas9-modified AuNWs, static Cas9-sgRNA-modified AuNWs, and US-propelled Cas9-sgRNA-modified AuNWs, respectively, e.g., relevant samples loaded with 60 nM of Cas9-sgRNA. Fluorescence images were taken at 0 h (right after the 5 min treatment), and at 0.5h, 2h, 5h, and 15h post-treatment; the scale bar is 400 µm. FIG. 9C shows a data plot depicting quantitative GFP fluorescence intensity of four samples, e.g., untreated AuNW motors, ultrasound-propelled Cas9-modified AuNW motors, static Cas9/sgRNA-modified AuNW motors, and ultrasound-propelled Cas9/sgRNA-modified AuNW motors. The bar chart represents the mean and standard deviation of three independent measurements. FIG. 9D shows a data plot depicting the mean GFP knockout percentage of the GFP-B16F10 cells treated with the different conditions.

Figure 10:
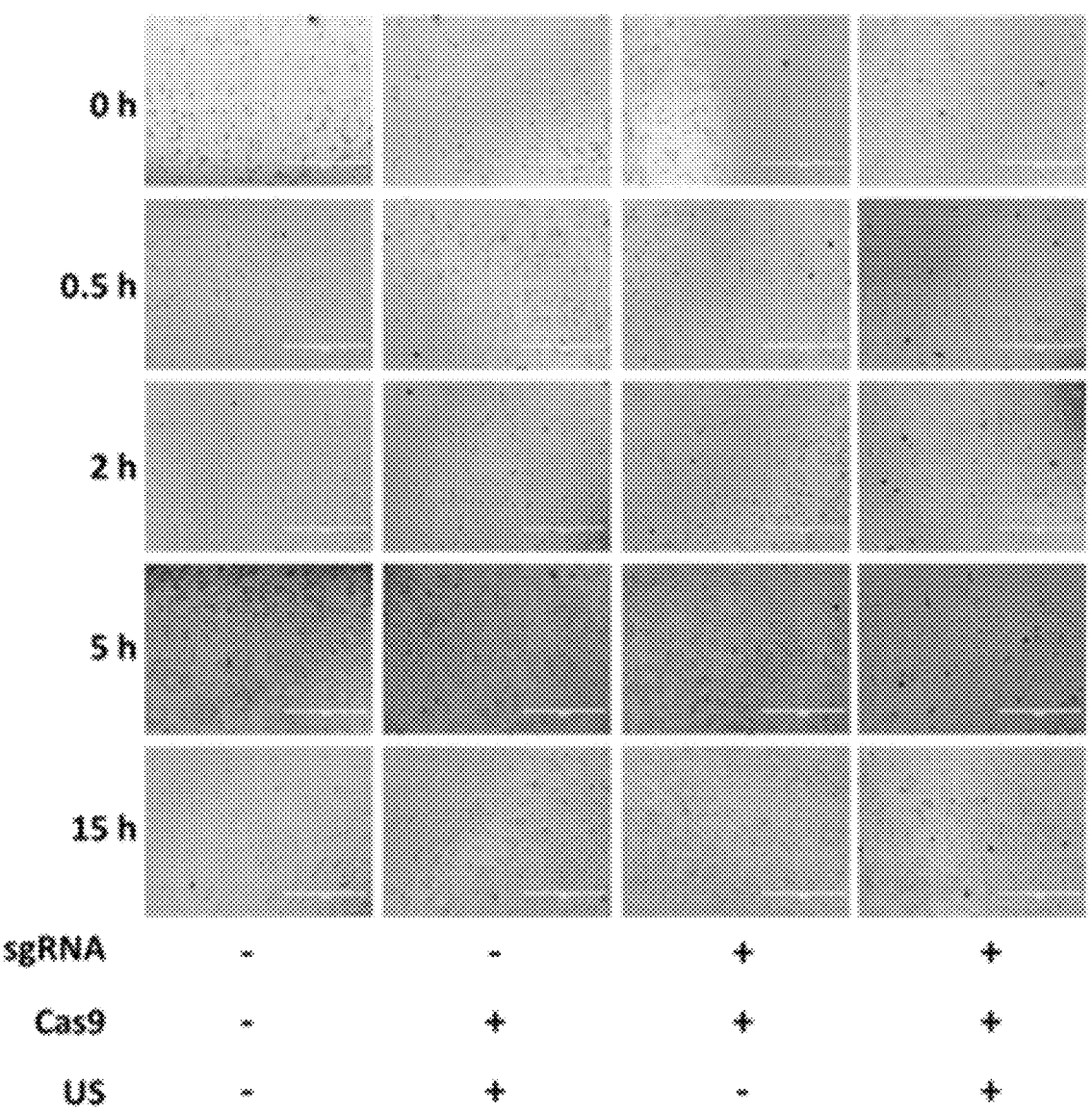
FIG. 10 shows optical images corresponding to the fluorescent images in FIG. 9B.

FIG. 10 shows optical images depicting the time-dependent knockout study comparing the incubation of B16F10-GFP cells with different controls. The Bright field images correspond to the fluorescence images of the time-dependent knockout study in FIG. 9B (from left to right), i.e., untreated GFP-B16F10 cells, GFP-B16F10 cells treated with US-propelled Cas9-modified AuNWs, static Cas9-sgRNA-modified AuNWs, and US-propelled Cas9-sgRNA-modified AuNWs, respectively. Images were taken at 0 h (right after the 5 min treatment), and at 0.5h, 2 h, 5 h, and 15 h post-treatment, and the scale bars are 400 µm.

The ability of the Cas9-sgRNA-modified AuNW motors 700 for gene editing was demonstrated by measuring the GFP knockout response in GFP-expressing B16F10 cells, and comparing the knockout efficiency with that of different control experiments. To verify the principle, the cells were treated for 5 min with the Cas9-sgRNA-modified AuNWs (loaded with 60 nM of Cas9-sgNRA) under an ultrasound field (e.g., 1.6 V and 2.66 MHz), followed by evaluating the fluorescence intensity of the treated cells at different times (0.5-15 h). Similar experiments with static Cas9-sgRNA-modified AuNWs or Cas9-modified AuNWs (i.e., gold nanowire motors loaded only with the Cas9 protein but not the sgRNA) were performed as controls. The example experiments were compared to untreated cells to calculate the corresponding GFP knockout percentage. As illustrated by the fluorescence images of FIG. 9B, corresponding bright-field images shown in FIG. 10, the normalized fluorescence intensities shown in the bar plot of FIG. 9C, and the calculated GFP knockout percentage shown in the plot of FIG. 9D, ~80% GFP knockout was obtained after 2 h treatment with the US-propelled Cas9-sgRNA-modified AuNWs. This was accompanied by a dramatic decrease of the time-dependent fluorescence intensity, shown by FIG. 9C.

In contrast, a slight decrease of the fluorescence signal was observed in cells treated with US-propelled Cas9-modified AuNWs, i.e., nanomotors loaded with the Cas9 protein but without the sgRNA. These results were similar to the untreated cells, since the presence of sgRNA is crucial for guiding the location of the endonuclease towards the correct sequence within the nucleus. Notably, cells treated with Cas9-sgRNA-modified AuNWs under static conditions also displayed GFP knockout due to the passive cell uptake of the AuNWs. However, the time-dependent decreased fluorescence, observed in these cells, was slower than that with the US-propelled Cas9-sgRNA-modified AuNWs, e.g., achieving a maximum of ~40% GFP knockout after 15 h incubation (as compared to the 80% knockout observed using the propelled Cas9-sgRNA-modified AuNW motors after 2 h). These results suggest the important role of the propulsion in mediating cell internalization of the motors without affecting the Cas9-sgRNA payload.

The dynamic Cas9-sgRNA-modified AuNWs nanomotors offered 5-fold enhanced GFP knockout after 0.5 h incubation compared to the passive uptake of static AuNWs using the same incubation time and Cas9-sgRNA loading. Another control experiment was carried out, which included incubating the cells with free 60 nM Cas9-sgRNA in solution and applying the ultrasound field for 5 min. As shown in FIGS. 11A-11C, a negligible GFP knockdown was observed after both 2 h and 24 h using the free Cas9-sgRNA complex in solution under ultrasound conditions. These example results further confirm the important role of the AuNW propulsion in the rapid intracellular delivery of Cas9-sgRNA and the subsequent efficient GFP knockout.

FIGS. 11A-11C show images and data plots depicting example results from free Cas9-sgRNA complex control experiments. FIG. 11A shows bright field and corresponding fluorescence images of untreated GFP-B16F10 cells and cells treated with 60 nM free Cas9-sgRNA complex in a solution under US conditions. FIG. 11B shows a data plot depicting the normalized fluorescence intensity. FIG. 11C shows a data plot depicting the GFP knockout percentage. The conditions of the example control experiments include the following: ultrasound conditions include 1.6 V, 2.66 MHz, 5 min; and cell incubation at 37° C. and 5% CO2. Images were taken at 2 h and 24 h post-treatment, and scale bars are 400 μm.

Figure 12:
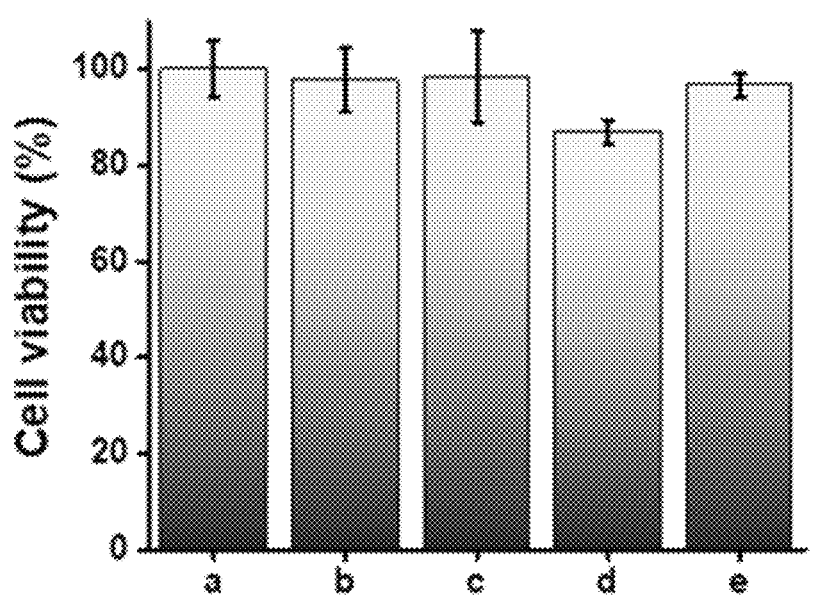
FIG. 12 shows a data plot showing example results of a cell viability test corresponding to results of FIGS. 9B-9D.

FIG. 12 shows a data plot showing example results of a cell viability test corresponding to results of FIGS. 9B-9D. The bars of the plot correspond to the average absorbance at 490 nm using a MTS assay across three wells of (from left to right): non-treated GFP-B16F10 cells (bar (a)), GFP-B16F10 cells after treatment with US-propelled Cas9-sgRNA-modified AuNW motors (bar (b)), static Cas9-sgRNA-modified AuNW motors (bar (c)), US-propelled Cas9-modified AuNW motors (bar (d)), and 60 nm free Cas9-sgRNA complex (bar (e)). The relevant nanomotors were modified with 60 nM of Cas9-sgRNA; ultrasound conditions included 1.6 V, 2.66 MHz, 5 min; and cell incubation was at 37° C. and 5% CO2, 15 h.

The viability of the B16F10 cells was evaluated using a cell proliferation spectrophotometric assay based on an MTS tetrazolium compound. Both the MTS kit results (shown in FIG. 12), and the corresponding optical images of the treated cells (shown in FIG. 11A), confirmed that the performed treatments did not significantly affect the viability of the cells after 15 h incubation, indicating absence of toxicity. Overall, these example results demonstrate that the nanomotor-based delivery method allows fast and efficient intracellular delivery of the functional Cas9-sgRNA complex, achieving up to ~80% knockout after just 2 h incubation. As will be illustrated below, such use of dynamic delivery vehicles offers a remarkably high knockout response even in the presence of ultralow levels of the Cas9-sgRNA complex.

Next the example implementations included testing the effect of Cas9-sgRNA complex concentration on the knockout efficiency. In this study, AuNWs were modified with different amounts of the Cas9-sgRNA complex (e.g., 0.6, 6, and 60 nM), and were then internalized into GFP-B16F10 cells through 5 min ultrasound-treatment. After the treatment, the fluorescence images of cells following different readout times were taken (FIG. 13A, and corresponding bright-field images in FIG. 14), the corresponding fluorescence intensity of the cells was quantified (FIG. 13B), and the GFP knockout percentage was calculated (FIG. 13C). It was clearly observed that ~60% GFP knockout was achieved after 2 h incubation even using 1% of the initial Cas9-sgRNA complex concentration (e.g., 0.6 nM), and that such GFP knockout increases up to ~95% after 48 h incubation. The possibility of achieving high GFP knockout efficiency using nanomotors loaded with 1% of the initial Cas9-sgRNA concentration results in distinctly advantageous genome editing in terms of minimizing non-desired side effects related to the use of high amounts of cargoes. Compared to other conventional approaches for intracellular Cas9-sgRNA delivery (Table 3), the present nanomotor-based strategy offers higher knockout efficiency using a shorter treatment time and a lower amount of Cas9-sgRNA. This study demonstrates also that the GFP knockout percentage depends on both the readout time and concentration of the Cas9-sgRNA complex used to functionalize the AuNW motors.

Figure 13B:
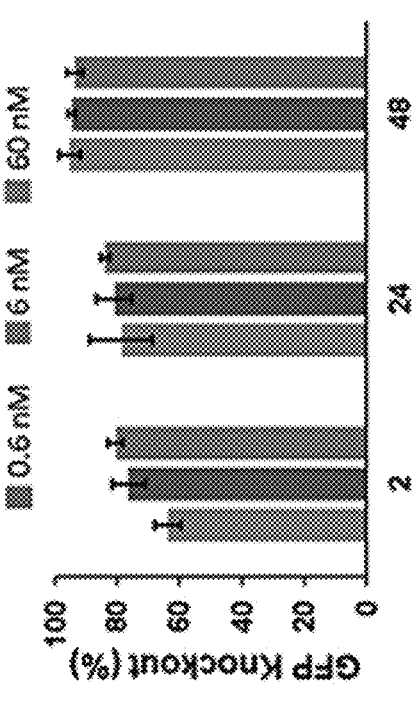
FIGS. 13A-13C show images and data plots depicting the effect of Cas9-sgRNA complex concentration on the knockout efficiency for GFP-B16F10 cells treated with example ultrasound-propelled Cas9-sgRNA-modified gold nanowire motors.
Figure 13C:
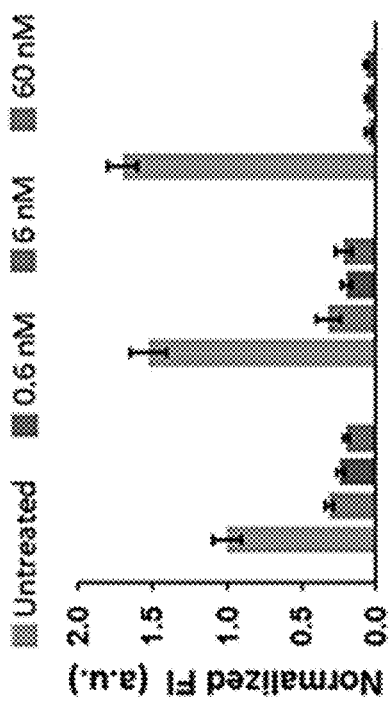
Figure 13A:
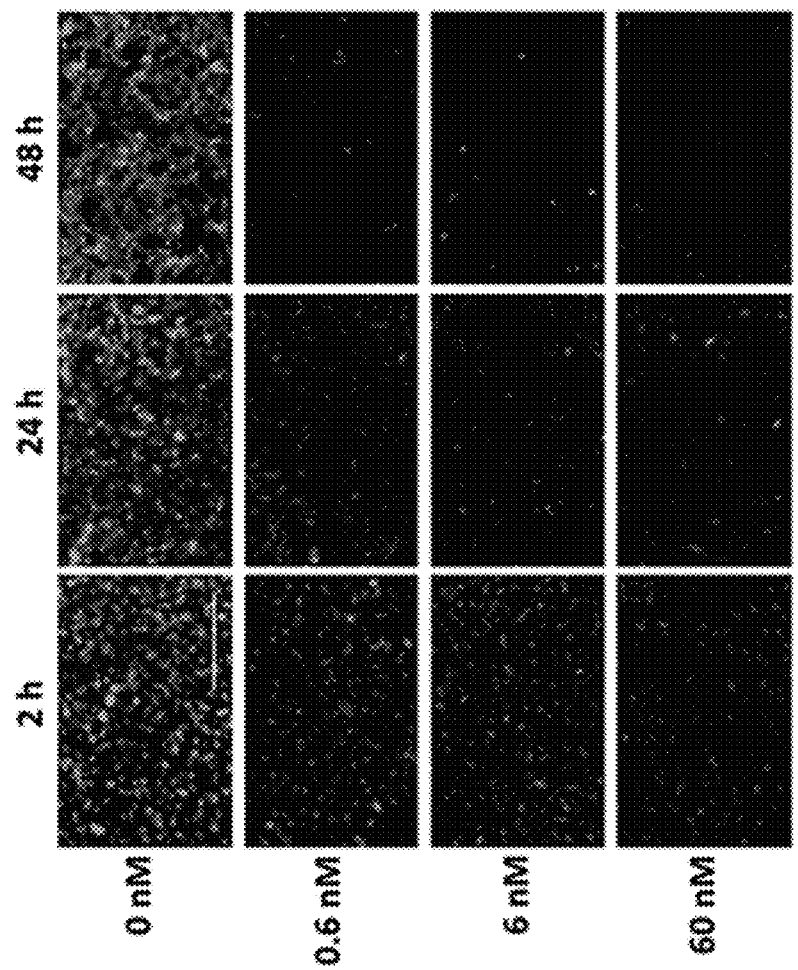

FIGS. 13A-13C show images and data plots depicting the effect of Cas9-sgRNA complex concentration on the knockout efficiency for GFP-B16F10 cells treated with US-propelled Cas9-sgRNA-modified AuNWs. FIG. 13A shows fluorescence images of (from top to bottom): untreated GFP-B16F10 cells, GFP-B16F10 cells treated with ultrasound-propelled Cas9-sgRNA-modified AuNW motors loaded with 0.6 nM, 6 nM and 60 nM of the Cas9-sgRNA complex, respectively. Fluorescent images were taken at 2 h, 24 h, and 48 h post-treatment, and the scale bar is 400 μm. FIG. 13B shows a data plot of quantitative GFP fluorescence intensity treated at different conditions as described in FIG. 13A. FIG. 13C shows a data plot of the mean GFP knockout percentage of the GFP-B16F10 cells treated at different conditions as described for FIG. 13A. The bar chart represents the mean and standard deviation of three independent measurements.

Figure 14:
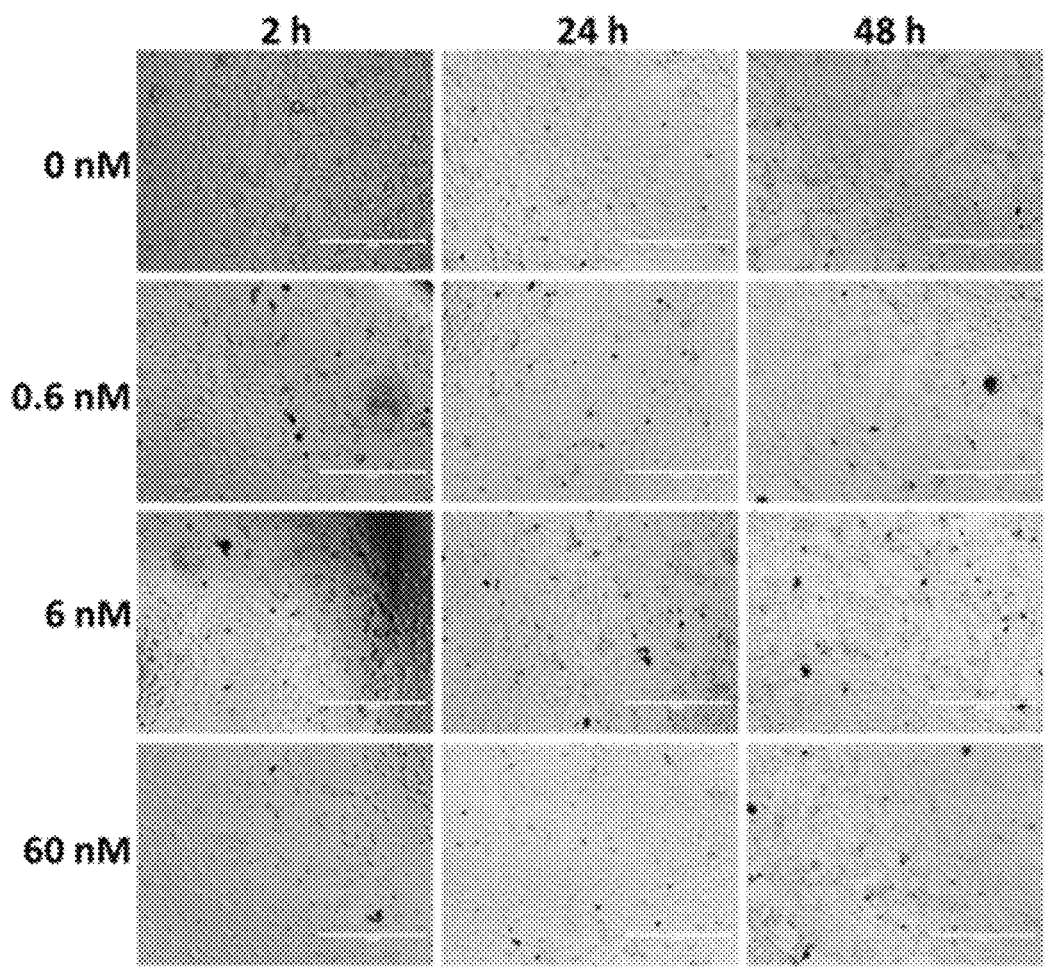
FIG. 14 shows optical images corresponding to the fluorescent images of FIG. 13A.

FIG. 14 shows optical images showing example results of the Cas9-sgRNA complex concentration-dependent knockout study comparing the incubation of GFP-B16F10 cells with Cas9-sgRNA-modified AuNW motors. These bright field images correspond to the fluorescence images shown in FIG. 13A for the Cas9-sgRNA complex concentration study (from top to bottom): non-treated GFP-B16F10 cells, GFP-B16F10 cells after treatment with US-propelled Cas9-sgRNA-modified AuNW motors loaded with 0.6 nM, 6 nM and 60 nM of Cas9-sgRNA complex. Images were taken at 2h, 24h, and 48h post-treatment, and the scale bars are 400 μm.

The motor-based delivery method was compared to the commonly used lipofectamine transfection agent using 0.6 and 60 nM Cas9-sgRNA. As shown in the fluorescence images of FIG. 15A and corresponding bright-field images in FIG. 16, a decrease of the fluorescence intensity was observed using both the lipofectamine- and motor-based transfection approaches. While both systems displayed time dependency, the efficiency of the transfection and GFP knockout obtained using US-propelled nanomotors was notably higher than using lipofectamine at both Cas9 concentration levels (FIG. 15B). Up to ~75% GFP knockout was observed after 2 h motor-treatment when using the 60 nM Cas9-sgRNA concentration; the knockout efficiency increases up to ~95% after 24 h incubation. However, in the case of lipofectamine-treated cells (using 60 nM of Cas9-sgRNA), the GFP knockout reached a maximum of ~60% after 48 h incubation (vs. 75% knockout for 2 h motor-treatment). Statistical analysis shows a superior GFP knockout using US-propelled motors at all times and concentrations (FIG. 15B). This confirms the high knockout efficiency of US-propelled nanomotors, demonstrating clear advantages in terms of intracellular delivery of Cas9-sgRNA complex and corresponding GFP knockout efficiency as compared to the use of common passive cellular transfection agents.

FIGS. 15A and 15B show images and data plots showing the comparison of the GFP knockout efficiency using Cas9-sgRNA-modified AuNWs and Cas9-sgRNA@lipofectamine. FIG. 15A shows fluorescence images of BF16F10 cells treated with (from top to bottom): 0.6 nM Cas9-sgRNA-lipofectamine, US-propelled 0.6 nM Cas9-sgRNA-modified AuNWs, 60 nM Cas9-sgRNA-lipofectamine, US-propelled 60 nM Cas9-sgRNA-modified AuNWs. Fluorescence images were recorded at 2 h, 24 h, and 48 h post-treatment, and the scale bar are 400 μm. FIG. 15B shows a data plot depicting the GFP knockout percentage upon the Cas9-sgRNA complex concentration of 0.6 nM (top) and 60 nM (bottom) at different incubation times. Unpaired student T test was performed, *=$P<0.05$, =$P<0.01$, *=$P<0.001$. Bar chart represents the mean with standard deviations from three independent measurements.

Figure 16:
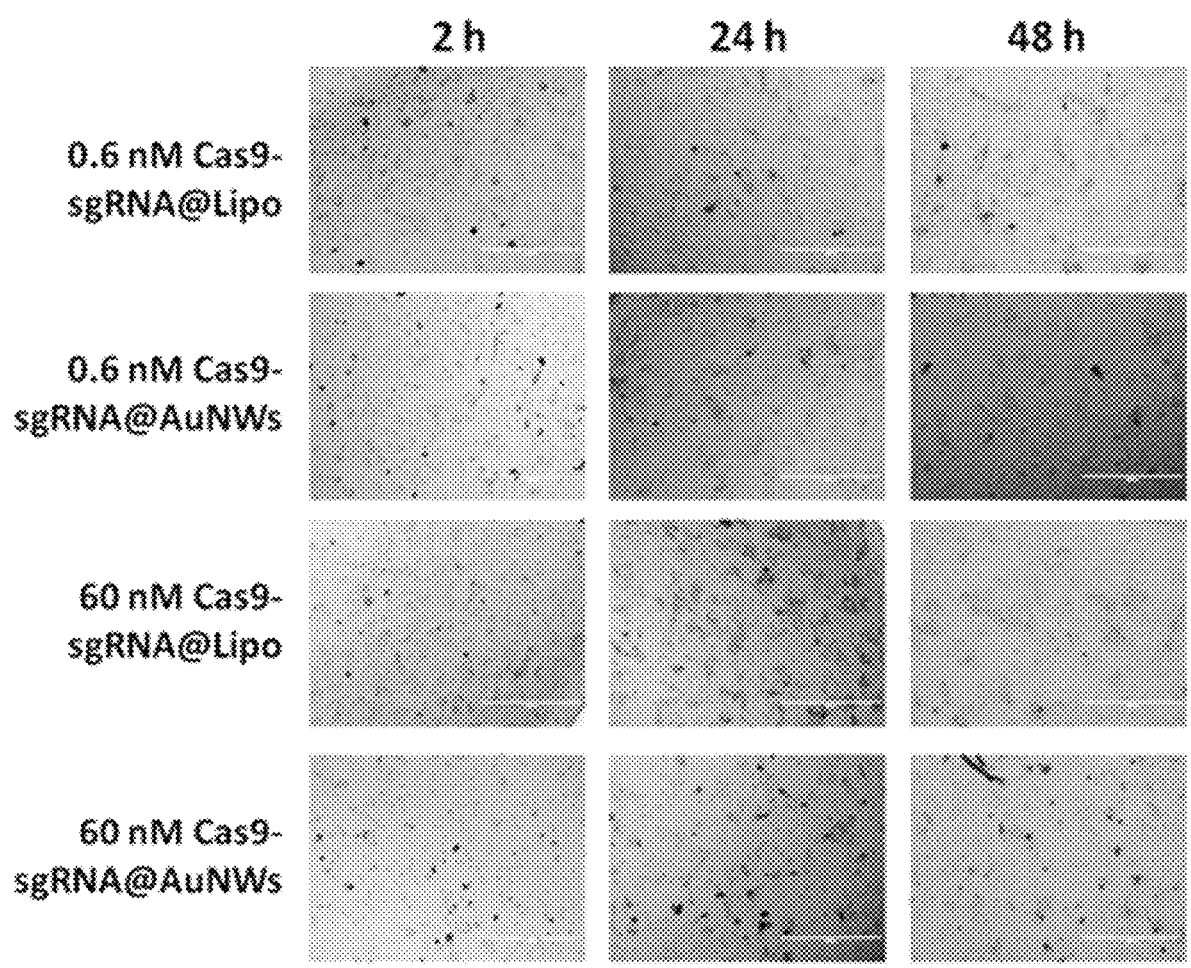
FIG. 16 shows optical images corresponding to the fluorescent images of FIG. 15A.

FIG. 16 shows optical images showing example results of a comparison of the GFP knockout efficiency using Cas9-sgRNA-modified AuNW motors and lipofectamine at two different Cas9-sgRNA complex concentrations. The bright field images correspond to the fluorescence images shown in FIG. 15A, and the scale bars are 400 μm.

Example methods for fabrication and implementations of the example nanomotors are described below.

Nanomotor Fabrication.

Gold nanowire (AuNW) motors 701 were prepared using a template-directed electrodeposition process. For example, a thin gold film was first sputtered on the surface of the porous polycarbonate membrane template with 400 nm diameter cylindrical nanopores. The membrane was then assembled in a Teflon plating cell and served as a working electrode using aluminum foil as an electrical contact for the subsequent electrodeposition. A sacrificial silver layer was electrodeposited into the branched area of the membrane using a Ag platting solution (e.g., 1025 Ag RTU, cat. no. X7522000; Technic, Inc.), using a charge of 0.1 C and a potential of −0.90 V (vs a Ag/AgCl reference electrode, and a Pt wire as a counter electrode). Subsequently, Au was plated using a gold plating solution (e.g., Orotemp 24 RTU RACK; Technic Inc., Anaheim, Calif., USA) at −1 V (vs Ag/AgCl) with a charge of 2 C. The sputtered gold layer and the silver sacrificial layer were simultaneously removed by mechanical polishing using cotton tip applicators soaked with aluminate powder (3-4 μm). For example, the removal of this sacrificial layer helped to create the concave shape in one end of the gold wire nanomotor, so the membrane was then etching with nitic acid concentrated ($HNO_3$) to remove the Ag sacrificial residual. Afterwards, the membrane was dissolved in methylene chloride (HPLC grade) for 30 min under the shaking for the complete release of the nanowires. The resulting AuNWs had a length of around 2 μm and a 400 nm diameter reflecting t deposition charge and the pore size of the polycarbonate membrane template. The nanomotors were separated from solution by centrifugation at 8000 rpm for 5 min and washed twice with isopropanol, ethanol, and ultrapure water in sequence. Between each washing steps, the nanomotor solution was mixed with desired solvent and briefly sonicated (e.g., for 3 sec) to ensure complete dispersion of nanomotors. The fabricated AuNWs were stored in 1 mL of ultrapure water at room temperature until use.

sgRNA Preparation.

CrRNA (1 μL, 100 μM) was added to tracrRNA (1 μL, 100 μM) in a nuclease-free buffer (1×IDTE) in a total volume of 100 μL. The mixture was heated to 95° C. for 5 min, and allowed to cool at room temperature. The complexed RNA was stored at 4° C. and allowed to reach at room temperature before use.

Cas9-sgRNA Complex Preparation.

The Cas9 protein was diluted directly from the supplied stock solution of 61 μM to a working concentration of 1 μM prior to use using a nuclease free HEPES buffer (e.g., 20 mM 4-(2-hydroxyethyl)-1-piperazineethanesulfonic acid, 150 mM KCl, pH 7.5). The complexed sgRNA (e.g., 1.5 μL, 1 μM) was added to the Cas9 protein (e.g., 1.5 μL, 1 μM) in a nuclease-free HEPES buffer in a final volume of 25 μL, e.g., to produce the Cas9/sgRNA complex 704. The mixture was allowed to react for 5 min. The Cas9-sgRNA complex was stored at 4° C. and allowed to reach at room temperature before use. This resulted in a 60 nM working solution. Further dilutions with nuclease-free HEPES buffer were carried out to obtain 6 nM and 0.6 nM Cas9-sgRNA solutions for motor modification. For the RNA free control, the RNA was omitted during the RNP preparation step.

Nanomotor Modification.

The external gold surface of the AuNWs (50 μL) was firstly modified by an overnight immersion in a 500 mM MPA (3-Mercaptopropionic acid) solution prepared in water, to obtain an appropriate self-assembly monolayer (SAM) for MPA-AuNWs. After washing twice with ultrapure water (by centrifugation at 7000 rpm for 5 min), the MPA-AuNWs were incubated with 100 mM cysteine and the coupling agents EDC/NHS (e.g., 400 mM EDC, 100 mM NHS in MES buffer, pH 6.5) for 2h, to obtain thiol group modified nanomotors. Following another washing step with nuclease-free buffer, SH-AuNWs were prepared for the functionalization with Cas9-sgRNA complex. Bare AuNWs were prepared using the same protocol to perform the corresponding control experiments. Cysteine-modified motors were immersed in a Cas9-sgRNA solution (e.g., 12.5 μL, 60 nM) and allowed to react for 2h at room temperature. The motors were then washed twice with nuclease free HEPES buffer (e.g., 50 μL). The supernatant was removed and the motors were resuspended in nuclease free HEPES buffer (e.g., 25 μL). Under the assumption that all protein was immobilized onto the motors surface, the resulting Cas9-sgRNA concentration was 30 nM. The incubation steps were carried out at room temperature.

Cell studies. GFP-expressing B16F10 cells (2.5 μL, containing ~7500 cells) were treated with the Cas9-sgRNA-modified AuNW motors (2.5 μL, 30 nM) in the ultrasound setup (1.6V, 2.66 MHz, 5 min) twice. A 5 min treatment was chosen. The mixture was transferred to a 96-well plate containing Dulbecco's Modified Eagle Medium (DMEM) containing 10% Fetal bovine Serum (FBS) (100 μL) buffer, and incubated up to 48 hours at 37° C. at 5% CO2. For the static control, the sonication step was omitted. For the untreated control, the motors where omitted. Each well was analyzed using an EVOS fluorescent cell imaging system at different times (e.g., 0, 0.5, 2, 5, 15, 24 and/or 48h) at room temperature. The GFP levels were quantified using ImageJ software.

Lipofection.

Lipofectamine RNAiMAX (e.g., 0.48 µL) was added to the RNP stock (e.g., 10 µL, 60 nM or 0.6 nM) and nuclease free HEPES buffer to a final volume of 20 µL. The mixture was allowed to react for 20 mins at room temperature. The Cas9-sgRNA-lipofactamine (e.g., 5 µL, 30 nM) was added to the cells (e.g., 5 µL, 15000 cells) in DMEM+10FBS serum in a total volume of 110 µL. The cells where incubated for 48 hours at 37° C. at 5% CO2.

Cell Viability Assay.

Cell viability was assessed using the CellTiter 96 Aqueous One Solution cell proliferation assay (Promega Corporation), based on a MTS tetrazolium compound. In brief, 10 µL of the MTS reagent was added into each well (containing the mix of nanomotors and cells), mixed gently, and incubated at 37° C. for 3 h. This was followed by reading the absorbance of the 96-well plate at 490 nm using a plate reader. The quantity of formazan product, measured by Abs at 490 nm, was directly proportional to the number of living cells. The percentage of viability was calculated assuming that the average absorbance of the wells containing non-treated cells represented 100% viability.

Ultrasound Equipment.

The acoustic cell setup included a piezoelectric transducer (Ferroperm PZ26 disk 10 mm diameter, 0.5 mm thickness) responsible for the generation of ultrasound waves, attached by conductive epoxy glue to the bottom center of a steel plate (e.g., 50×50×0.94 $mm^3$); then the steel plate was covered with a 240 µm kapton tape protective layer and a sample reservoir at the center (5 mm). A glass slide was used to cover the reservoir for ultrasound reflection and to protect the sample. The continuous ultrasound sine wave was applied via a piezoelectric transducer, through an Agilent 15 MHz arbitrary waveform generator, in connection to a homemade power amplifier. The applied continuous sine waveform had a frequency of 2.66 MHz and voltage amplitude of 1.6 V.

TABLE 3

Delivery methods for direct cytosolic Cas9-sgRNA delivery and together with knockout efficiency and treatment condition.

| Strategy | Knockdown, % | Amount of Cas9-sgRNA | Treatment time | Cell incubation time |
|---|---|---|---|---|
| DISCLOSED APPROACH US-propelled intracellular delivery of Cas9-sgRNA-modified AuNWs | 69%-97% | 0.024 µg, 0.006 µg sgRNA | 5 min | 0.5-15 h |
| CONVENTIONAL APPROACH Delivery of Cas9 protein/gRNA using lipofectamine CRISPRMAX | 85% genome editing efficiency in HEK293FT cells | 0.04 µg Cas9, 0.09 µg sgRNA | 3 h | 48-72 h |
| CONVENTIONAL APPROACH Mammalian cell engineering via Cas9 protein transfection | 66% indel by lipofection, up to 94% indel by electroporation | Lipofection: 0.5 µg Cas9, 0.005-0.1 µg sgRNA Electroporation: 24 µg Cas9, 4.8 µg sgRNA | 1 h | 48 h |
| CONVENTIONAL APPROACH Delivery of Genome-Editing Proteins in Vitro and In Vivo | up to ~80% eGFP negative cells (Lipofectamine 2000), 60% indel efficiency (ex vivo) | 4.4 µg Cas9, 0.3 µg sgRNA | 4 h | 48 h |
| CONVENTIONAL APPROACH Delivery of CRISPR-Cas9 for Genome Editing via Self Assembled DNA Nanoclews | 29-30% indel efficiency | 8 µg Cas9, 1.1 µg gRNA | 3 h | 48 h |
| CONVENTIONAL APPROACH Modified guide RNA and donor DNA for CRISPR-Cas9 engineering | ~20% NHEJ/HDR efficiency(Positive gating captured the top 20% of Alexa647 positive cells and negative gating captured the bottom 20% of cells) | 8 µg Cas9, 1.33 µg sgRNA | 16 h | 72 h |
| CONVENTIONAL APPROACH Cytosolic Delivery of CRISPR/Cas9-Ribonucleoprotein | up to ~40% GFP loss, 28% mutation frequency (ex vivo) | 10 µg CAs9, 2 µg sgRNA | 3 h | 48 h |
| CONVENTIONAL APPROACH RNA-guided genome editing in human cells via delivery of purified Cas9 ribonucleoproteins | Up to 79% Indel efficiency | 15 µg Cas9, 20 µg sgRNA | 24 h | 48 h |

Table 4 shows an example sequence for example oligonucleotides.

| Oligonucleotide | Sequence (5'→3') |
|---|---|
| GFP target sequence | 5'-GGGCACGGGCAGCTTGCCGG-3' (SEQ ID NO: 7) |
| crRNA | 5'-GGGCACGGGCAGCUUGCCGGGUUUUAG AGCUAUGCU-3' (SEQ ID NO: 8) |

The example implementations of the example motile nano- and microstructures for active and dynamic intracellular payload delivery in accordance with the present technology have demonstrated the successful application of ultrasound-propelled nanomotors for rapid and efficient intracellular delivery of functional Cas9-sgRNA complex using the knockout of GFP encoding gene as a model. The example implementations demonstrate that ultrasound-propelled Cas9-sgRNA functionalized gold nanowires 700 were able to rapidly internalize into GFP-expressing B16F10 cells and dramatically decrease the fluorescence intensity through knockout of GFP encoding gene, after GSH-mediated release of Cas9-sgRNA from the nanomotors. These Cas9-sgRNA loaded nanomotors were shown to rapidly penetrate the cell membrane and to markedly improve the efficiency and speed of GFP gene knockout process, inducing up to ~80% GFP knockout within 2h of cell incubation, e.g., as compared to ~30% with their static counterparts. Moreover, the high intracellular delivery and gene editing efficiency were confirmed by dramatically reducing the loading amount of the Cas9-sgRNA complex. Even with 1% of the initial Cas9-sgRNA complex concentration, the nanomotors led to ~60% knockout of target gene within 2h and ~95% after 48h. The Cas9-sgRNA-modified AuNWs also displayed improved cell transfection and faster GFP knockout compared with common lipofectamine-based cell transfection agent. The example implementations indicated the capability of utilizing US-propelled nanomotors as a dynamic delivery vehicle for direct and efficient intracellular delivery of large and active payloads, e.g., such as Cas9-sgRNA toward different therapeutic purposes.

Example Implementations of Nanomotors for Intracellular Caspase-3 Delivery

Direct and efficient intracellular delivery of enzymes to cytosol holds tremendous therapeutic potential despite remaining technical challenges. While intracellular delivery of functional proteins offers tremendous therapeutic potential, the difficulty of rapid cytosolic delivery of proteins in active conformation is massive and still represents an unmet challenge. The disclosed nano- and microscale motors can be implemented to deliver enzymes in their active conformation intracellularly to target cells. Herein, an example remote propulsion nanomotor approach uses caspase-3 (CASP-3) as a model enzyme for active and dynamic delivery in a cell. Gold nanowire (AuNW) motors were functionalized with a pH-responsive polymer coating, in which the CASP-3 is loaded, and the resulting polymer modified nanomotors protect the enzyme from release and deactivation prior to reaching an intracellular environment. Upon entering a cell and exposure to the higher intracellular pH, the polymer coating is dissolved, thereby directly releasing the active CASP-3 enzyme to the cytosol and causing rapid cell apoptosis. In vitro studies using gastric cancer cells as a model cell line demonstrates that such motion-based active delivery approach leads to remarkably high apoptosis efficiency within significantly shorter time and lower amount of CASP-3 compared to other control groups without involving ultrasound-propelled nanomotors. For example, the disclosed nanomotor system can achieve 80% apoptosis of human gastric adenocarcinoma (AGS) cells within only 5 min, which dramatically outperforms other CASP-3 delivery approaches. These results indicate that the ultrasound-propelled nanomotors may act as a powerful vehicle for cytosolic delivery of active therapeutic proteins, which would offer an attractive means to enhance the current landscape of intracellular protein delivery and therapy. While CASP-3 is selected as a model protein in the described implementations, for example, the same nanomotor approach can be readily applied to a variety of different therapeutic proteins.

CASP-3 is a highly promising therapeutic protein. This cysteine protease catalyzes the specific cleavage of key cellular proteins and thus plays a crucial role in programmed cell death (apoptosis). Intracellular delivery of sufficient levels of active CASP-3 into the cytosol of target cells can induce the cells to undergo apoptosis by cleaving essential substrates while minimizing side effects to healthy tissues and cells associated with current therapeutics. Moreover, since the native form of CASP-3 is an endogenous cell component that requires external stimuli to activate it, the delivery of a functionally active form of this enzyme obviates side effects and toxicity issues associated with external stimuli such as the use of chemical and radioactive therapeutics for inducing targeted cell apoptosis. However, the intracellular delivery of active CASP-3 enzyme is extremely challenging, due to its negative charge, heterotetrameric state, and the fragile nature of its active site. Although some conventional strategies have been described for intracellular delivery of CASP-3, such as those based on the use of lipid or poly(disulfide)s mediated mechanisms or different nanovehicles or delivery reagents, these existing approaches relied on complex protocols and required long incubation times and high amounts of the apoptotic enzyme.

The example ultrasound-powered polymer-modified nanowire motors in accordance with the present technology represent a particularly attractive platform to overcome biological barriers and physical limitations associated with the conventional methods for functional protein internalization, and provide a simple and efficient strategy for intracellular delivery of enzymes like CASP-3. The disclosed nanomotor-based apoptosis strategy relies on the accelerated intracellular delivery of active enzyme (e.g., CASP-3), encapsulated within a biocompatible pH-responsive polymeric coating on the nanomotors. In the example implementations described herein, a pH-responsive polymer (e.g., Eudragit® L30 D-55) was used for encapsulating CASP-3 enzyme, e.g., which provides rapid dissolution above pH 5.5 and, thereby, safe arrival of the active enzyme to the intracellular environment while preventing the CASP-3 release in the extracellular space.

Figure 17A:
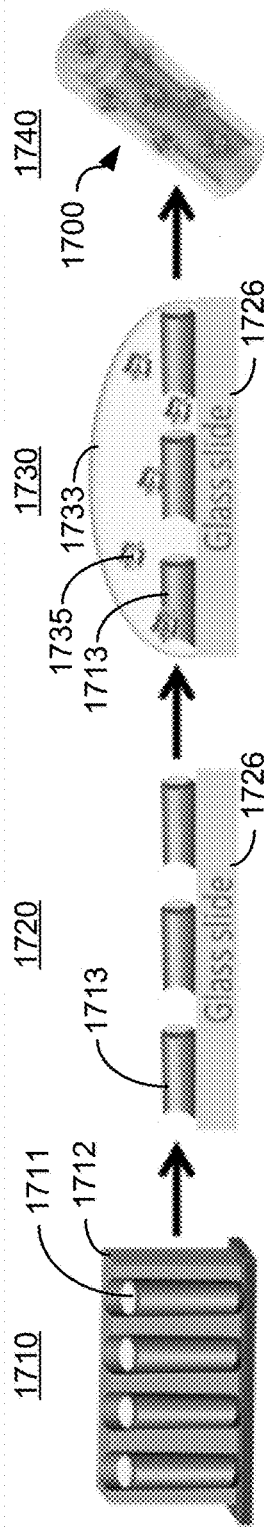
FIGS. 17A and 17B show illustrative diagrams depicting the preparation and implementation of an example nanomotor delivery device for intracellular delivery of an enzyme in active confirmation in accordance with the present technology.
Figure 17B:
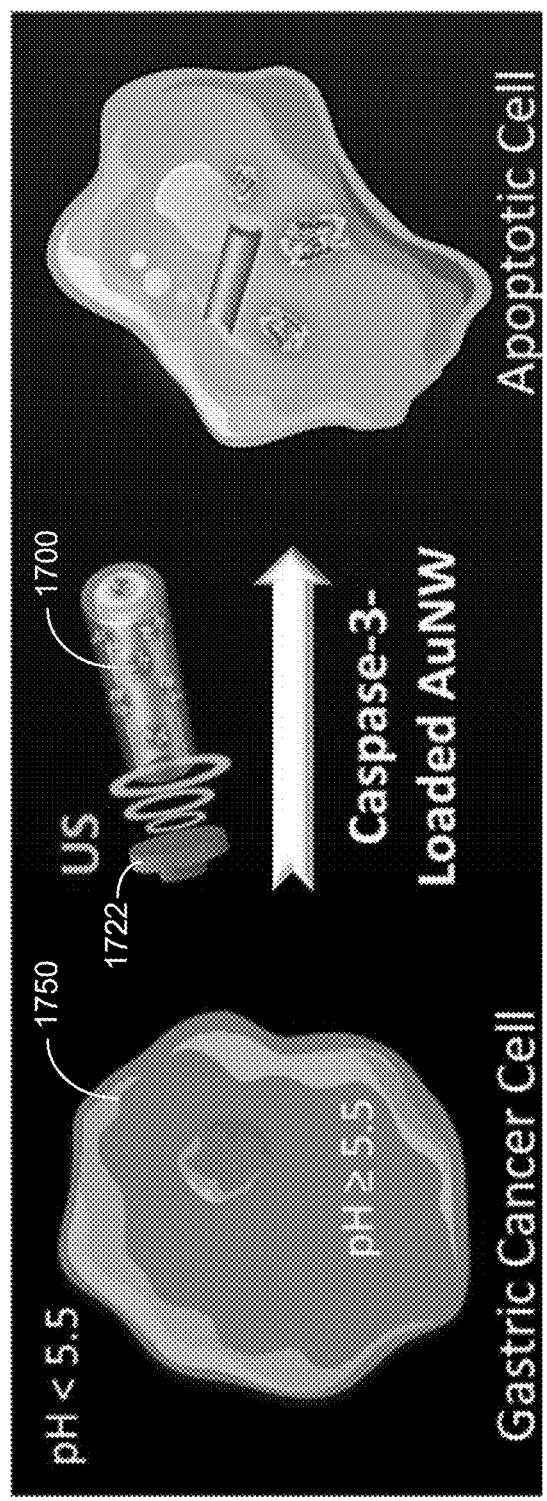
Figure 17C:
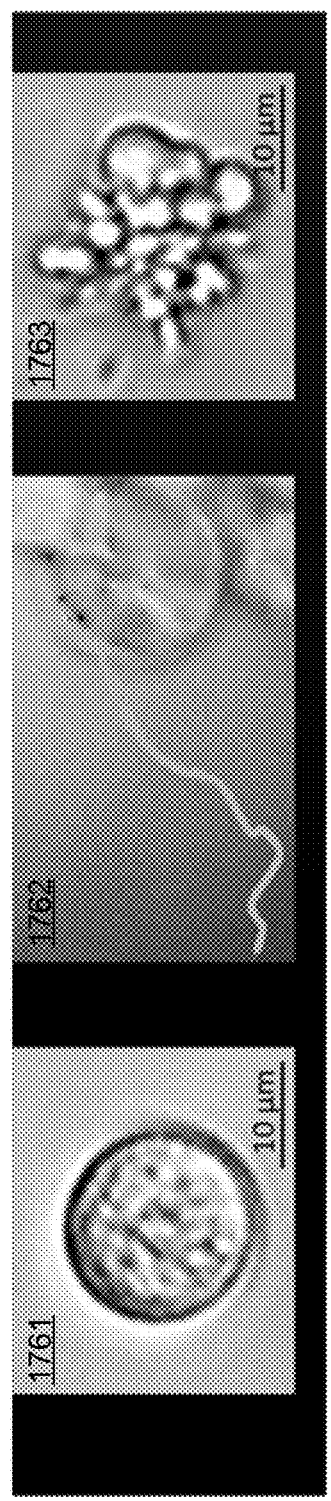
FIG. 17C shows optical images of an example implementation of an example casepase-3/polymer-modified gold nanowire motor with a human gastric adenocarcinoma cell before, during and after propulsion.

FIG. 17A-17C show illustrative diagrams and images depicting the preparation and implementation of example pH-responsive polymer/CASP-3 coated AuNW motors (CASP-3/polymer-modified AuNWs) for intracellular delivery of the enzyme caspase-3 in active confirmation. FIG. 17A shows a diagram illustrating an example method for producing an example embodiment of the intracellular delivery nanomotor device in accordance with the present technology. In this example, gold nanowire motors are fabricated using an example membrane-template electrodeposition method that includes electrodeposition of a conductive material 1711 (e.g., gold) within the nanopores of a template membrane 1712 (e.g., an alumina membrane) as shown in panel 1710, and dissolution of the membrane 1712 and release of the resulting nanostructures to produce the nanowire motors 1713 as shown in panel 1720. In some implementations of the fabrication method, the produced nanowire motors 1713 are immersed in a fluid and released on a substrate 1726 (e.g., glass slide), e.g., for surface modification and/or transfer. For example, a droplet of the fluid containing the nanowire motors 1713 can be dispersed onto the substrate 1726 and subsequently dried. The fabrication method includes coating the nanowire motors 1713 with a pH-responsive polymeric layer 1733 containing the active enzyme 1735 (e.g., CASP-3 enzyme), as shown in panel 1730, to produce the active enzyme-polymer coated nanowire motors 1700 (e.g., CASP-3/polymer-modified AuNWs) as shown in panel 1740. In some implementations of the fabrication method, for example, the pH-responsive polymer/CASP-3 film was completely dried, and the produced CASP-3/polymer-modified AuNWs were collected by softly scratching the glass slide. In some implementations, for example, the nanowire motors 1703 can be fabricated to include a magnetic material in the nanowire segment, which can allow the nanowire motors to be easily and specifically guided to the target cell or tissue, e.g., limiting the apoptosis strictly to the target cancer cells and minimizing the toxicity evoked to normal cells.

FIG. 17B shows a diagram illustrating an example method for intracellular delivery of the active enzyme-loaded nanomotor device 1700 in a target cell, e.g., gastric cancer cell. For example, in situ CASP-3 delivery using the remotely propelled active enzyme-loaded nanomotors 1700 accelerates cell apoptosis process through delivery of the caspase-3 enzyme 1735 in active conformation within the cell 1750. As shown in the diagram of FIG. 17B, the CASP-3/polymer-modified AuNWs 1700 enter the target cell 1750 through ultrasound-propelled motion of the nanomotors applied by an ultrasound system 1722, causing the CASP-3/polymer-modified AuNWs 1700 to penetrate and pass through the cell exterior into the cell. Within the cell, the pH-responsive polymer coating dissolves, releasing the enzyme payload to induce cell apoptosis.

FIG. 17C shows images of an example implementation of the CASP-3/polymer-modified AuNWs 1700 with an example human gastric adenocarcinoma (AGS) cell before propulsion of the nanomotors (image 1761), during propulsion of the nanomotors (time-lapse image 1762), and during resultant apoptosis of the AGS cell due to intracellular delivery of the active caspase-3 enzyme by the nanomotors (image 1763). For example, the time-lapse image 1762 illustrates that the CASP-3/polymer-modified AuNW motors 1700 move under an applied ultrasound field, approaching the target cell. Upon entering the cell, the nanomotors are subject to intracellular pH environment (e.g., pH >5.5), leading to dissolution of their pH-sensitive coating and concomitant release of active CASP-3 enzyme, which subsequently induces rapid cell apoptosis (shown in image 1763).

Table 5 shows a comparison of the example CASP-3/polymer-modified nanomotors 1700 for intracellular delivery of active caspase-3 as compared to conventional approaches for intracellular CASP-3 delivery, which demonstrates that the disclosed nanomotor-based apoptotic strategy offers the highest apoptosis efficiency using significantly shorter time and a lower amount of CASP-3.

TABLE 5

| Strategy | CASP-3 amount | Apoptosis time | Apoptosis, % |
| --- | --- | --- | --- |
| DISCLOSED APPROACH Intracellular delivery by US-propelled CASP-3/polymer-modified AuNWs 1700 | 3.4 ng | 5 min | 80.0 |
| CONVENTIONAL APPROACH Lipid-mediated intracellular delivery | 3.3 ng | o/n | 58.0 |
| CONVENTIONAL APPROACH BioPorter ™ Protein delivery reagent | 250 ng | 2 days | 80.0 |
| CONVENTIONAL APPROACH Intracellular delivery with NP-Stabilized Nanocapsules | $7.5 \times 10^8$ ng | 1 h | 72.0 |
| CONVENTIONAL APPROACH Intracellular delivery by PLGA-CNTs conjugates | 3,000 ng/mL | 3 days | 70.0 |
| CONVENTIONAL APPROACH Intracellular delivery by cell-penetrating Poly(disulfide)s | 50 nM | 2 h | 50.0 |
| CONVENTIONAL APPROACH Intracellular delivery based on reversible and specific assembly of His-tagged CASP-3 onto soluble Ni-immobilized polymer | 1,536 ng | 1 day | 80.0 |
| CONVENTIONAL APPROACH Au-nanosurface energy transfer probe for real-time monitoring of cell apoptosis | 3.75 ng | 3 h | 70.0 |

Figure 18A:
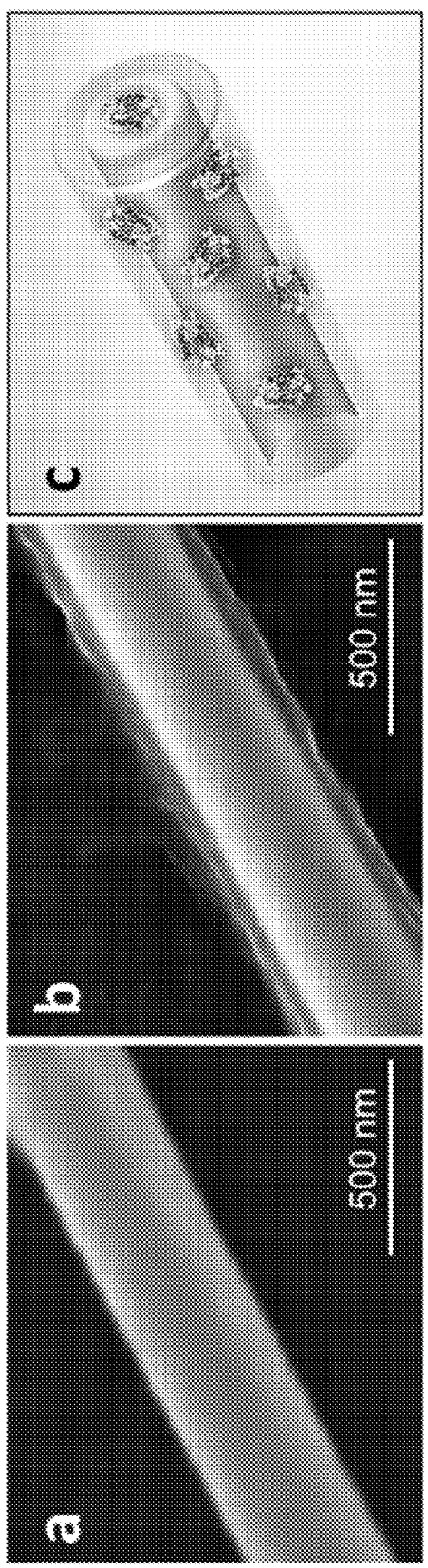
FIGS. 18A-18C show characterization images of example nanomotors including an example active enzyme-loaded nanomotor device.
Figure 18B:
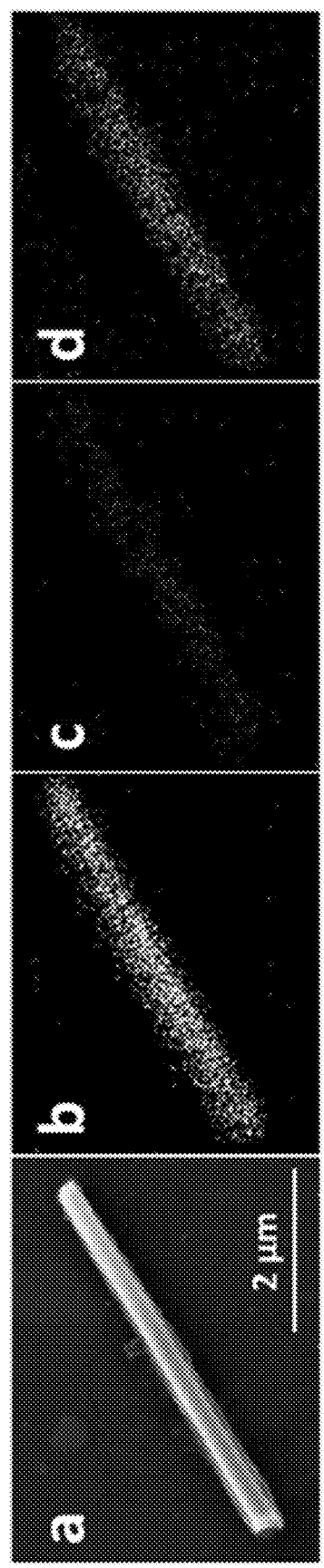
Figure 18C:
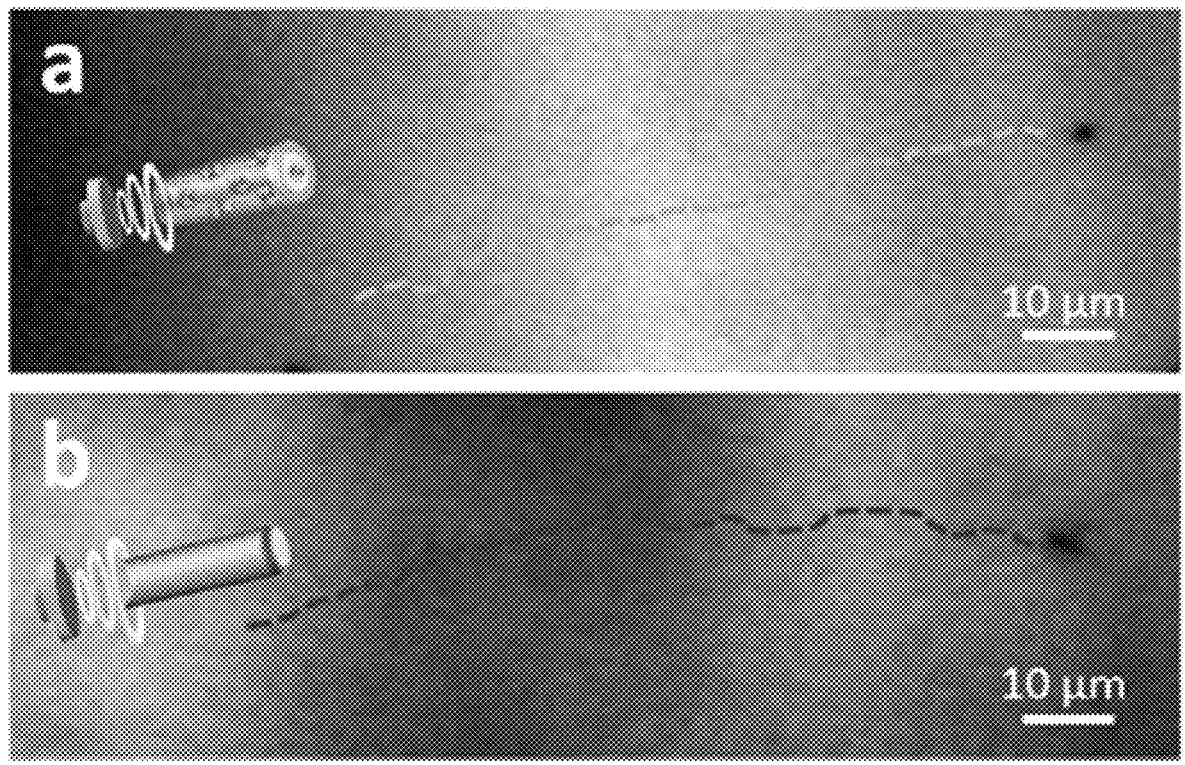

FIGS. 18A-18C show characterization images of example nanomotors including an active enzyme-loaded nanomotor device. FIG. 18A shows scanning electron microscopy (SEM) images that compare an uncoated AuNW (image (a)) and the example CASP-3/polymer-modified nanomotor 1700 (image (b)), along with an illustration of the CASP-3/polymer-modified nanomotor (diagram (c)). FIG. 18B shows an SEM image of a CASP-3/polymer-modified nanowire motor (image (a)), and corresponding energy-dispersive X-ray spectroscopy (EDX) images showing the distribution of gold (image (b)), carbon (image (c)), and nitrogen (image (d)). FIG. 18C show time-lapse optical images showing the propulsion behavior of an example CASP-3/polymer-modified nanowire motor (top image (a)) and an uncoated gold nanowire motor (bottom image (b)).

The SEM images examined the structural morphology of the gold nanowire motors. The SEM image (a) of FIG. 18A shows the wire structure of the uncoated nanomotor with a 200 nm diameter, which reflects the pore size of the alumina membrane template. The SEM image (b) of FIG. 18A and SEM image (a) of FIG. 18B show the polymer/enzyme coating along the nanomotor structure, in which the diameter of the coated nanomotors is estimated from these images to be 280±8 nm, e.g., indicating an average coating thickness of ~40 nm. The presence of Au, C, and N (from the motor core, polymer, and enzyme, respectively) was confirmed from the corresponding EDX mapping images shown in FIG. 18B images(b), (c), and (d), respectively. The ultrasound-propulsion of the example CASP-3/polymer-modified nanomotors was compared to that of uncoated AuNWs, shown from the time-lapse images of FIG. 18C image (a) and image (b), respectively.

Figure 18D:
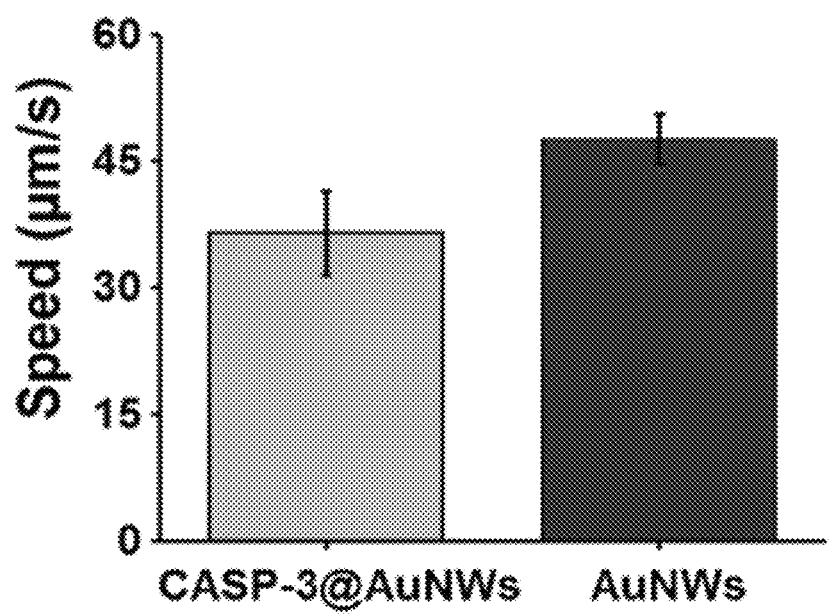
FIG. 18D shows a data plot comparing the speed of example ultrasound-powered enzyme/polymer-modified nanowire motors and uncoated nanowire motors.

FIG. 18D shows a data plot comparing the speed of example ultrasound-powered CASP-3/polymer-modified nanowire motors 1700 (left bar) and uncoated gold nanowire motors (right bar), in which the applied ultrasound field conditions were at 6 V, 2.56 MHz. The example CASP-3/polymer-modified nanomotors displayed efficient propulsion when compared to uncoated AuNWs, e.g., yielding average speeds of 37 and 47 µm/s, respectively. Such behavior indicates that coating of the motors with the polymer/CASP-3 film has a small effect upon their propulsion speed. Such fast movement allows for efficient internalization of the CASP-3/polymer-modified nanomotors into the cells.

In the example implementations, prior to demonstrating the in vitro cell apoptosis induced by the CASP-3/polymer-modified AuNWs, the enzymatic loading yield of the nanomotors was quantified by using a CASP-3 activity assay. Such assay relies on measuring the production of a CASP-3-dependent luminescent signal. Initially, a luminescence intensity calibration plot was constructed using different concentrations of pure CASP-3 (FIG. 19A).

Subsequently, AuNWs were loaded with CASP-3, and the loaded CASP-3 was released in vitro by increasing the solution pH from 5.0 to 7.0, e.g., ensuring complete dissolution of the polymer and the consequent release of the enzyme. After separating the nanomotors, the supernatant containing the released enzyme was analyzed with the CASP-3 assay kit. The loading yield of the enzyme was then calculated by interpolating the luminescence intensity of the released CASP-3 into the CASP-3 calibration plot. The estimated CASP-3 loading yield of 3.4 ng per batch of $6 \times 10^5$ motors was obtained, which was considered optimal to induce apoptosis also by other researchers. This loading yield was thus used for the example implementations.

Figure 19A:
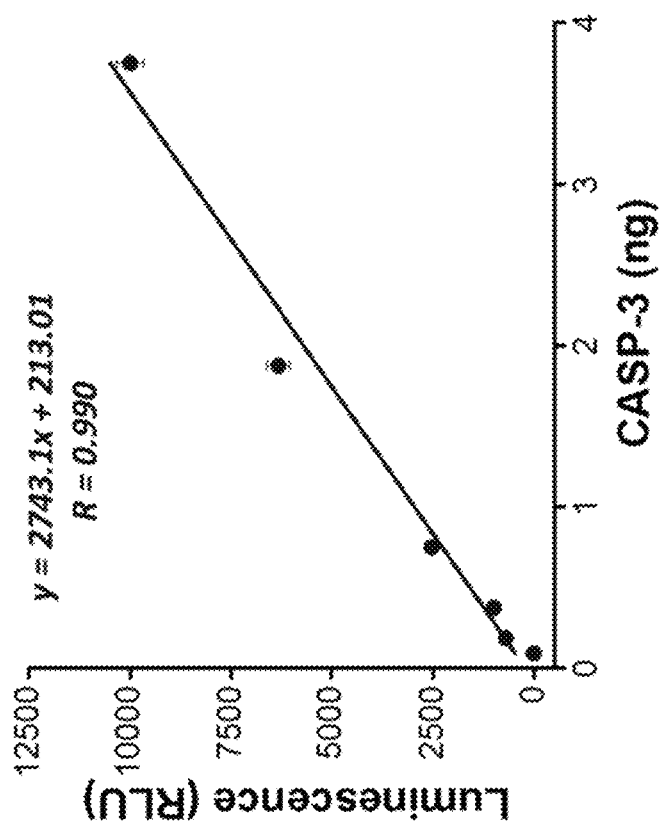
FIGS. 19A and 19B show estimations of CASP-3 loading on example nanomotors.
Figure 19B:
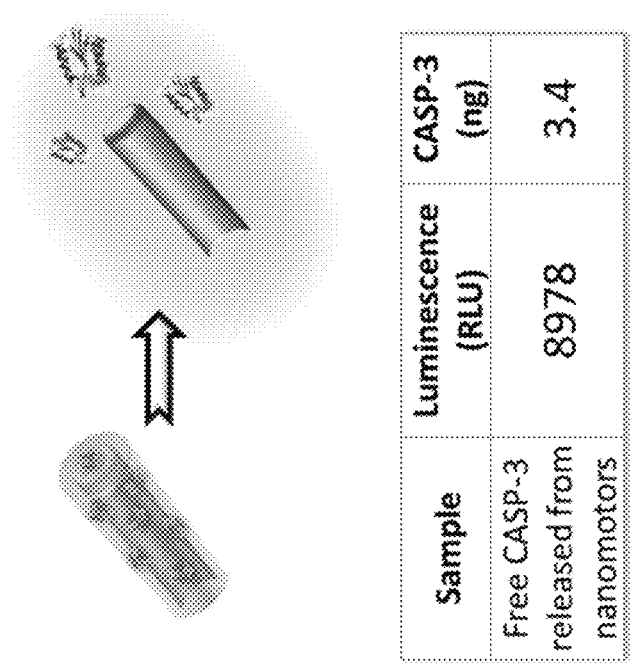

FIGS. 19A and 19B show estimations of CASP-3 loading on example nanomotors. FIG. 19A shows a data plot of the calibration of CASP-3 obtained by using the Caspase-Glo® 3/7 Assay, and FIG. 19B shows the calculated amount of CASP-3 from enzyme-loaded nanomotors (e.g., mean value calculated from the average of 3 measurements).

Figure 20:
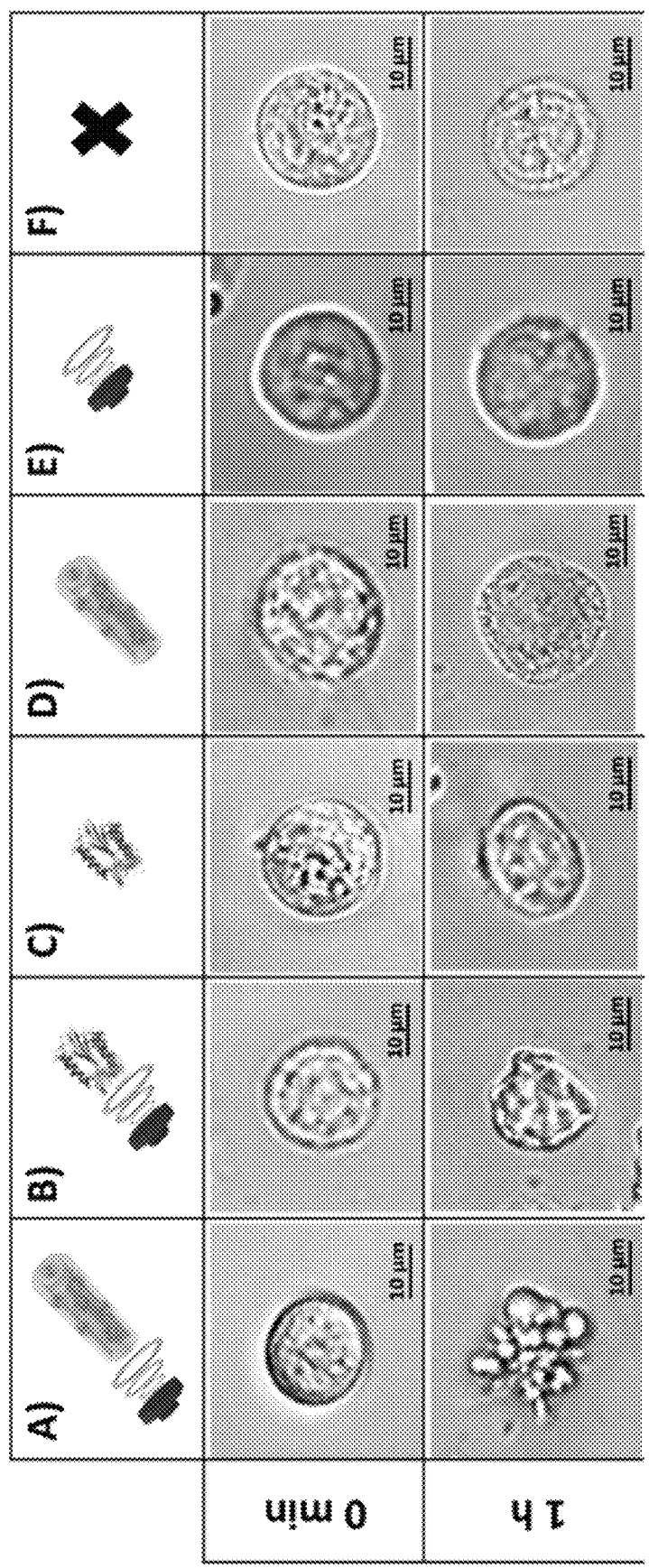
FIG. 20 shows optical images from an example implementation evaluating morphological changes of AGS cells treated with various nanomotor conditions.

FIG. 20 shows optical images from an example implementation evaluating morphological changes of AGS cells treated with the ultrasound-propelled CASP-3/polymer-modified nanowire motors and with control conditions before and after 1 h treatment. Comparison of optical microscope images are taken at different times (i.e., 0 min and 1 h) of AGS cells treated with US-propelled CASP-3/polymer-modified AuNWs (column A); 3.4 ng of free CASP-3 and applying ultrasound (column B); 3.4 ng of free CASP-3 without ultrasound (column C); CASP-3/polymer-modified AuNWs without ultrasound (column D); ultrasound alone, i.e., no nanomotors (column E); and untreated AGS cells, e.g., used as a negative control (column F).

Clear changes in the cell morphology, indicative of cell apoptosis (i.e., irregular shape with blebs), were observed after treating the cells with the ultrasound-propelled CASP-3/polymer-modified nanowire motors shown in column A, as compared to the untreated AGS cells shown in column F. A morphological change was also observed when treating cells with the free solution-phase CASP-3, with or without an ultrasound field (shown in column B and column C, respectively). On the other hand, negligible morphological changes of the AGS cells were observed following treatment with static CASP-3/polymer-modified AuNWs (shown in column D), which demonstrates the important role of the nanomotor propulsion to enable effective internalization of the nanomotors by the cells. Also, no apparent morphological changes were observed using cells treated with US field alone (shown in column E).

Figure 21A:
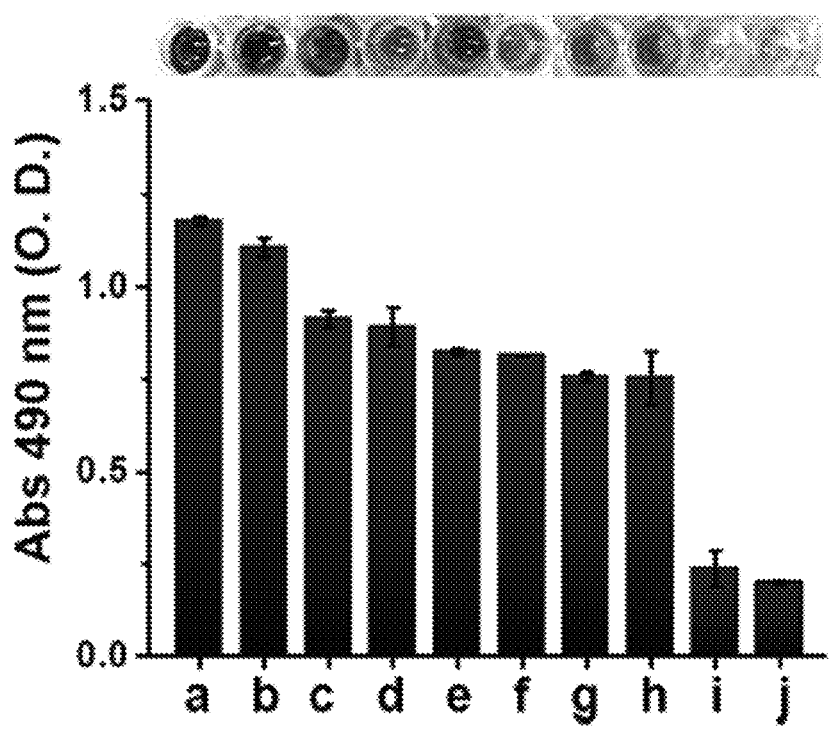
FIGS. 21A and 21B show data plots of example results from an implementation characterizing apoptosis of gastric cancer cells induced by the example enzyme/polymer-modified nanowire motors and control conditions.
Figure 21B:
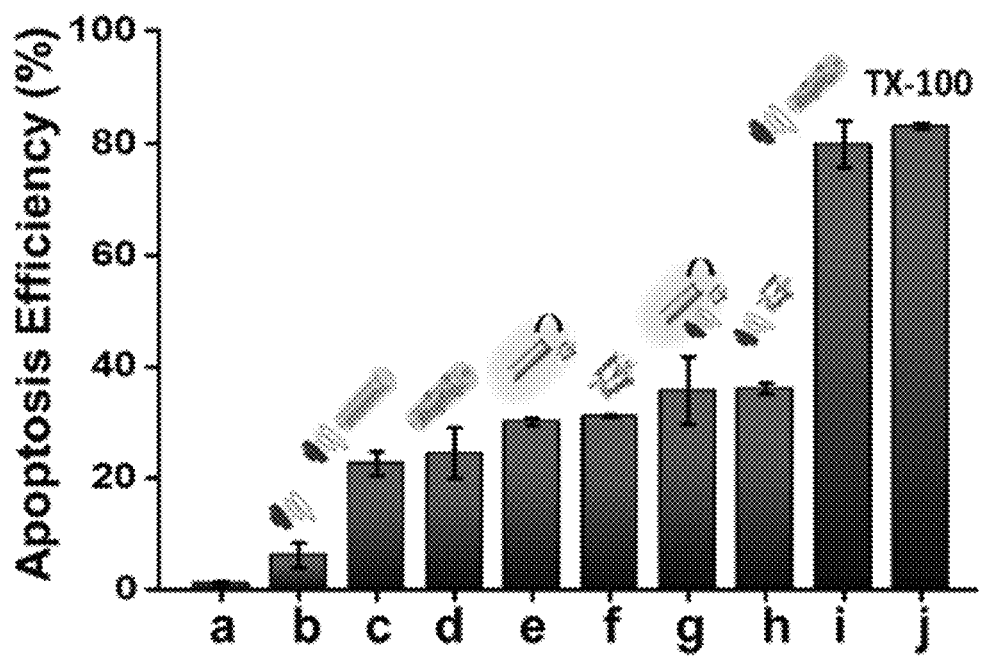

FIGS. 21A and 21B show data plots of example results from an implementation characterizing apoptosis of gastric cancer cells induced by the example CASP-3/polymer-modified AuNW motors and control conditions. The data plot of FIG. 21A shows MTS cytotoxicity assay results, in which the absorbance measured at 490 nm from cells incubated under different conditions: (a) untreated cells, (b) cells only treated with ultrasound, (c) cells treated with ultrasound-powered polymer coated AuNWs (i.e., no CASP-3), (d) cells treated with static CASP-3/polymer-modified AuNWs (i.e., no ultrasound), (e) cells treated with CASP-3 released from motors and static conditions, (f) cells treated with same amount of free CASP-3 under static conditions, (g) cells treated with CASP-3 released from motors and ultrasound conditions, (h) cells treated with same amount of free CASP-3 under ultrasound conditions, (i) cells treated with the example ultrasound-powered CASP-3/polymer-modified AuNWs, and (j) cells treated with 2% Triton X-100 used as a positive control. The cells were incubated with the MTS reagent at 37° C. for 3 h before measuring the corresponding absorbance. FIG. 21B shows a bar plot illustrating the cell apoptosis efficiency observed in the different treatment groups, in which the ultrasound conditions included: 6 V, 2.56 MHz and 5 min; and the other conditions included: 110 µL total solution volume; $6 \times 10^5$ nanomotors; $5 \times 10^3$ AGS cells; 3.4 ng of CASP-3; Dulbecco's Modified Eagle Medium (DMEM).

Figure 21C:
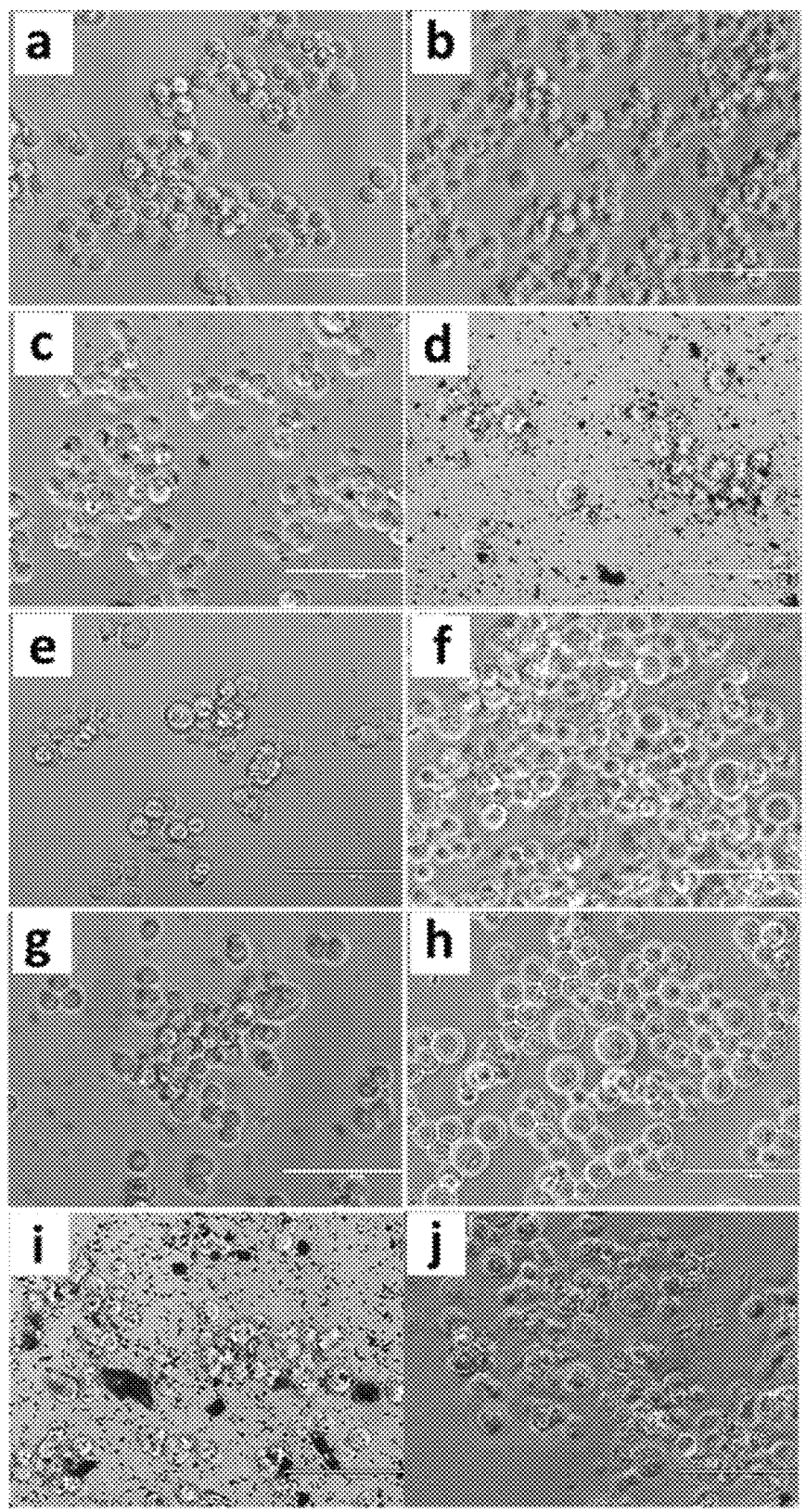
FIG. 21C shows corresponding optical images of the cells in the conditions assayed for FIGS. 21A and 21B.

FIG. 21C shows the corresponding optical images of the cells in the conditions assayed. The corresponding optical microscope images include (a) untreated cells, (b) cells only treated with ultrasound, (c) cells treated with ultrasound-powered polymer coated AuNWs (i.e., no CASP-3), (d) cells treated with static CASP-3/polymer-modified AuNWs (i.e., no ultrasound), (e) cells treated with CASP-3 released from motors and static conditions, (f) cells treated with 3.4 ng of free CASP-3 under static conditions, (g) cells treated with CASP-3 released from motors and ultrasound conditions, (h) cells treated with 3.4 ng amount of free CASP-3 under ultrasound conditions, (i) cells treated with the example ultrasound-powered CASP-3/polymer-modified AuNWs, and (j) cells treated with 2% Triton X-100.

For example, the different control experiments were carried out to further confirm the role and performance of the ultrasound-propelled CASP-3/polymer-modified AuNWs in rapidly inducing cell apoptosis. This example study involved evaluation of the AGS cell viability using a standard cell proliferation spectrophotometric assay based on a MTS tetrazolium compound. The measured absorbance values and the estimated apoptosis efficiency (%) are shown in FIGS. 21A and 21B, respectively.

The example control experiments were compared to untreated AGS cells (negative control, bar a), and to AGS cells treated with 2% Triton X-100 (positive control, bar j). An initial control experiment, for example, was carried out using only ultrasound indicated minor apoptosis efficiency (bar (b)). In agreement with the qualitative observations of the cell morphology experiments, the highest apoptosis efficiency was observed using the example ultrasound-powered CASP-3/polymer-modified nanowire motors. For example, these coated nanomotors resulted in 80.0% apoptosis efficiency, which was 3.3-times higher than the 24.4% efficiency observed with the static ones (shown by bar (i) versus bar (d) of FIG. 21B). Such dramatic enhancement of the apoptosis efficiency demonstrates the effect of the propulsion in the CASP-3 induced apoptosis process. Moreover, the 80.0% apoptosis achieved using ultrasound-propelled CASP-3/polymer-modified AuNWs, e.g., compared with the 36.1% apoptosis using free CASP-3 released from the motor under the same US conditions (bar (i) versus bar (h) of FIG. 21B), demonstrates the significant role of AuNWs in cytosolic delivery of CASP-3. Notably, for example, a similar apoptosis efficiency was observed using the same amount of free CASP-3 in solution and CASP-3 released in vitro from the nanomotors under static conditions (e.g., 31.0% versus 30.1%, shown in bar (f) and bar (e) of FIG. 21B, respectively) or under ultrasound condition (e.g., 36.1% versus 35.7%, shown in bar (h) and bar (g) of FIG. 21B, respectively). Overall, these example results demonstrate the high efficacy of the disclosed intracellular protein delivery approach using the example pH-responsive polymer-coated nanowire motors. The data shows that CASP-3 maintains its activity after immobilization on the motors using the example pH-responsive polymer. Notably, caspases are delicate enzymes that are susceptible to inactivation during delivery process, and these example results reflect the protective action of the pH-responsive polymer and indicate their stability throughout the nanomotor-based delivery process. For example, the stability of the loaded enzyme (e.g., caspase) may be attributed to the entrapment of the enzyme within the polymer coating that retains a stable CASP-3 structure similar to that observed after its confinement in polyethylene glycol (PEG).

The disclosed nanomotor strategy for intracellular delivery of proteins in active conformation can provide among the highest apoptosis efficiency, while using significantly shorter times and smaller amounts of the protein. The example implementations using an example embodiment of the nanomotor technology, i.e., CASP-3/polymer-modified gold nanowire motors, have shown substantially faster apoptosis and lower amounts of caspase-3 that reflect the movement of the remotely-propelled AuNWs and their efficient delivery of active CASP-3 to the cytosol of target cells, as well as the stability of the active caspase-3 in the pH-responsive polymer.

Example methods for fabrication and implementations of the example nanomotors are described below.

Example reagents and solutions included the following. A pH-responsive coating (e.g., enteric polymer Eudragit® L30 D-55) was obtained from Evonik Industries (Germany). Active Recombinant Human Caspase-3, (CASP-3, 5 µg, 37.5 KDa) was obtained from BioVision, Inc. (Milpitas, Calif.). The lyophilized CASP-3 was reconstituted in phosphate buffer saline (PBS) solution pH 7.4 containing 15% glycerol. The enzyme was divided into 90 nM aliquots, and immediately stored at −70° C. until use. Standard solutions of the enzyme were prepared daily from the 90 nM stored aliquots in the same buffer solution. AGS cells (human gastric adenocarcinoma, ATCC® CRL-1739™) were cultured in Ham's F-12K medium (Gibco) supplemented with 10% fetal calf serum (Hyclone), penicillin-streptomycin (Gibco) at 37° C. in a humidified atmosphere containing 5% $CO_2$. Before the experiments, cell cultures were detached with 0.25% trypsin-EDTA (Gibco) and resuspended in fresh cell culture media. Concentrations of cells in suspension were measured by hemocytometer and adjusted to $50 \times 10^3$ cells/mL by cell culture media. The example chemicals used were of analytical-grade reagents, and deionized water was obtained from a Millipore Milli-Q purification system (18.2 MΩ cm at 25° C.).

Example nanomotor fabrication processes included the following. The gold nanowire (AuNW) motors were prepared by a template-directed electrodeposition protocol. A thin gold film was first sputtered on one side of the porous alumina membrane template containing 200-nm diameter cylindrical nanopores to serve as a working electrode. The membrane was assembled in a Teflon plating cell with aluminum foil serving as an electrical contact for the subsequent electrodeposition. A sacrificial copper layer was electrodeposited into the branched area of the membrane using a 1 M cupric sulfate pentahydrate solution ($CuSO_4.5H_2O$), using a charge of 8 C and a potential of −0.90 V (vs a Ag/AgCl reference electrode, along with a Pt-wire as a counter electrode). For example, the removal of this sacrificial layer helped to create the concave shape in one end of the gold wire nanomotor. Subsequently, Au was plated using a gold plating solution (e.g., Orotemp 24 RTU RACK; Technic Inc., Anaheim, Calif.) at −0.95 V (vs Ag/AgCl), using a charge of 3.5 C. The resulting AuNWs had a length of around 4 µm. The sputtered gold layer and the copper sacrificial layer were simultaneously removed by mechanical polishing using cotton tip applicators soaked with 0.5 M $CuCl_2$ solution in 20% HCl. The membrane was then dissolved in a 3 M NaOH solution for 30 min to completely release the nanowires. The resulting nanomotors were separated from solution by centrifugation, e.g., at 7,000 rpm for 5 min, and washed repeatedly with ultrapure water (18.2 MΩ cm) until a neutral pH was achieved. Between washing steps, the nanomotors solution was mixed with ultrapure water and briefly sonicated (e.g., 3s) to ensure complete dispersion of nanomotors in the washing water. The AuNWs were stored in 1 mL of ultrapure water at room temperature until use.

Example CASP-3 loading onto nanomotors included the following. The Eudragit® L30 D-55 enteric polymer was loaded with CASP-3 enzyme and coated on the AuNW motors to prevent the release of CASP-3 from the nanomotors in the extracellular environment, thus ensuring the safe arrival of the active enzyme to the intracellular space. First, a batch of AuNWs (e.g., ~$6 \times 10^5$ motors) was collected in water, and the micromotor suspension was dispersed onto a glass slide and let it until dried. The CASP-3-loaded nanomotors were prepared by using a mixture of Eudragit® L30 D-55 polymer and 90 nM CASP-3 solution. The nanomotors were coated with a 100 µL film of the enzyme-polymer mix solution. Finally, after the enzymatic-polymeric film was completely evaporated, the pH-responsive-polymer-CASP-3@AuNWs were collected in a 1.5 mL tube by lightly scratching the motors off the glass slide. The steps were carried out at room temperature. pH-responsive polymer-coated AuNWs without CASP-3 were also prepared using the same protocol to perform the corresponding control experiments. The polymeric-enzyme coating thickness was examined by SEM. The 200 nm original diameter of the nanomotors (e.g., defined by the micropores of the alumina membrane template) was compared with the 280±8 nm coated-nanomotors, e.g., calculating an average coating thickness of ~80 nm.

Example quantification of the CASP-3 loading yield included the following. To estimate the CASP-3 loading on the nanomotors, a luminescent assay that measures caspase-3 activity (CaspaseGlo® 3/7 Assay; Promega Corporation) was used. First, a luminescence intensity calibration plot using different concentrations of pure CASP-3 was constructed, e.g., being the luminescent signal proportional to the amount of caspase activity. Then, AuNWs were loaded with CASP-3 following the protocol described above. After that, the loaded CASP-3 was in vitro released by increasing the pH of the solution from 5.0 to 7.0, thus ensuring the complete dissolution of the polymer and the consequent release of the enzyme. After separate the nanomotors, the supernatant containing the released enzyme was mixed with the CaspaseGlo® 3/7 reagent following the specifications of the kit. Luminometer readings were taken after 1 hour incubation at room temperature. The luminescence intensity of the released CASP-3 was interpolated into the luminescence intensity calibration plot, from which the loading yield of enzyme was calculated. The estimated CASP-3 loading yield was 3.4 ng per batch of nanomotors (e.g., average value based on the values calculated from 3 different batches of nanomotors).

Example in vitro intracellular apoptosis induction included the following. The nanomotor-based cell apoptosis induction mechanism involved the in vitro apoptosis induction of AGS cells by the intracellular CASP-3 released from the pH-responsive polymer-CASP-coated nanomotors. To perform these experiments, a mixture of 2.5 µL of the cell suspension (e.g., ~600 cells/µL) and 2.5 µL of the CASP-3/pH-responsive polymer AuNWs (e.g., ~6×10$^5$ nanomotors) was prepared and put into the US holder, applying 6 V and 2.56 MHz during 5 min. After performing 3 incubations, for example, the total volume (e.g., ~5.0×10$^3$ cells) of the mixture solution was placed in a well containing 90 µL Corning cellar DMEM media (e.g., pH adjusted to 5.0) with 4.5 g/L glucose, L-glutamine, and sodium pyruvate; 10% Hylcone Bovine Growth Serum (FBS); and 1% penicillin streptomycin.

Example cell viability/apoptosis assay included the following. To determine the apoptosis efficiency, cell viability was assessed using the CellTiter 96® AQueous One Solution Cell Proliferation Assay (Promega Corporation), based on a MTS tetrazolium compound. In brief, 10 µL of the MTS reagent were added into each well (containing the mix of nanomotors and cells), mixed gently, and incubated at 37° C. for 3 h. This was followed by reading the absorbance of the 96 well-plate at 490 nm using a plate reader. The quantity of formazan product as measured by Abs at 490 nm was directly proportional to the number of living cells. The percentage of apoptosis was calculated assuming that the average absorbance of the wells containing non-treated cells represented 100% viability.

Example ultrasound equipment included the following. The acoustic cell setup included a piezoelectric transducer (e.g., Ferroperm PZ26 disk 10 mm diameter, 0.5 mm thickness) responsible for the generation of ultrasound waves, attached by conductive epoxy glue to the bottom center of a steel plate (e.g., 50 mm×50 mm×0.94 mm$^3$); then the steel plate was covered with a 240 µm kapton tape protective layer and a sample reservoir at the center (e.g., 5 mm). A glass slide was used to cover the reservoir for ultrasound reflection and to protect the sample. The continuous ultrasound sine wave was applied via a piezoelectric transducer, through an Agilent 15 MHz arbitrary waveform generator, in connection to a home-made power amplifier. The applied continuous sine wave form had a frequency of 2.56 MHz and 6 V voltage amplitude. Videos and images were captured using Cool SNAP HQ$^2$ camera, 20× and 40× objectives (unless mentioned otherwise) and acquired at the frame rate of 10 using the Metamorph 7.1 software (Molecular Devices, Sunnyvale, Calif.). A Nikon Eclipse 80i upright microscope was also used to capture time course images of the morphological changes of AGS cells treated with ultrasound-propelled CASP-3/pH-responsive polymer-modified nanomotors and other conditions.

The example implementations of the example motile nano- and microstructures for active and dynamic intracellular payload delivery in accordance with the present technology have demonstrated that the combination of synthetic nanomotors with apoptotic enzyme caspase-3 enabled direct and rapid intracellular protein delivery with significantly enhanced cell apoptosis efficacy and efficiency compared to other delivery approaches. Specifically, the example ultrasound-propelled CASP-3/pH-responsive polymer-modified nanomotors were shown to be rapidly internalized into cancer cells and dramatically improve the apoptosis efficiency, e.g., as compared with static nanomotors or free enzyme-based approaches using similar CASP-3 levels. Up to 80% apoptosis of AGS cells was observed after 5 min treatment with the example intracellular active protein delivery nanomotors. Such improvement reflects the necessity and importance of fast internalization and rapid intracellular movement of nanomotors for effective cytosolic protein delivery. A series of control experiments supported the important role of the nanomotor movement in the efficient induction of apoptosis, and of the pH responsive polymer in ensuring the functional activity of the delivered enzyme. The example implementations clearly indicate that the propulsion nanomotors may act as an efficient vehicle for direct cytosolic delivery of active therapeutic proteins.

EXAMPLES

The following examples are illustrative of several embodiments in accordance with the present technology. Other exemplary embodiments of the present technology may be presented prior to the following listed examples, or after the following listed examples.

In some embodiments in accordance with the present technology (example A1), a device includes a nanomotor operable to propel in a medium and penetrate into a living cell in the medium; and a nucleic acid attached to the nanomotor and including a nucleotide sequence configured to affect expression of a target gene of the cell having a complementary nucleotide sequence to that of the nucleic acid.

Example A2 includes the device of example A1, in which the nucleic acid is attached to the nanomotor via rolling circle amplification (RCA).

Example A3 includes the device of example A1, in which the nanomotor includes a gold nanowire.

Example A4 includes the device of example A3, in which the nucleic acid is attached to the gold nanowire via gold-thiol interactions.

Example A5 includes the device of example A1, in which the nanomotor is operable to propel in the medium based on a localized chemical conversion on the nanomotor that creates a force to drive the nanomotor.

Example A6 includes the device of example A1, in which the nanomotor is operable to propel in the medium based on an applied external energy source including one or more of acoustic energy, electrical energy, magnetic energy, or optical energy.

Example A7 includes the device of example A6, in which the applied external energy source includes ultrasound.

Example A8 includes the device of example A7, in which the nanomotor includes a nanowire structured to include a concave shape at one end of the nanowire that is acoustically responsive to applied acoustic energy.

Example A9 includes the device of example A8, in which the applied acoustic energy causes gaseous bubbles in the medium to form and exit the concave shape to propel the nanomotor to move in the medium.

Example A10 includes the device of example A1, in which the nucleic acid includes one or more of siRNA, a miRNA, shRNA, antisense oligonucleotide, RNA or DNA.

Example A11 includes the device of example A1, further including a small molecular payload attached to the nanomotor.

Example A12 includes the device of example A1, in which the medium includes an in vitro medium including the cell, or in which the medium includes an in vivo medium including tissue that includes the cell.

In some embodiments in accordance with the present technology (example A13), a method for gene therapy includes providing nanomotors each including a nanowire and a nucleic acid attached to the nanowire in a medium including a plurality of cells, in which the nucleic acid includes a nucleotide sequence configured to affect expression of a target gene of the cell having a complementary nucleotide sequence to that of the nucleic acid; propelling the nanomotors in the medium to cause at least some of the nanomotors to penetrate into the cell; and suppressing the target gene of the cell based on interaction of the nucleic acid.

Example A14 includes the method of example A13, in which the propelling the nanomotor includes applying ultrasound energy.

Example A15 includes the method of example A14, further including pre-concentrating the nanomotors and the cells into a localized pressure node region of the medium based on the application of the ultrasound energy, in which the nanomotors bombard the wall of the cells, leading to piercing and penetration of the nanomotors into the cells.

Example A16 includes the method of any of examples A13-A15, in which the nanomotor includes the device according to any of examples A1-A12.

In some embodiments in accordance with the present technology (example B1), a method for intracellular delivery of a compound to a living cell includes providing a plurality of nanomotors operable to propel in a medium comprising a cell, in which a nanomotor of the plurality of nanomotors includes a functionalization layer on an outer surface of the nanomotor coupling a payload substance in a biologically active conformation to the nanomotor; propelling the nanomotors in the medium to cause at least some of the nanomotors to penetrate into an intracellular region of the cell; and administering the payload substance within the intracellular region of the cell to initiate an interaction of the biologically active payload substance with an intracellular constituent of the cell.

Example B2 includes the method of example B1, in which penetration of the cell by the at least some of the nanomotors through the cell membrane of the cell does not cause cell death.

Example B3 includes the method of example B1, in which the propelling the nanomotors in the medium includes applying an external energy source including one or more of acoustic energy, electrical energy, or magnetic energy to cause the nanomotors to move in the medium toward the cell.

Example B4 includes the method of example B1, in which the nanomotors are structured to include a rigid and asymmetric nanowire body having a concave cavity at one end of the nanowire body.

Example B5 includes the method of example B4, in which the propelling the nanomotors includes applying ultrasound energy to produce a remote ultrasound pulse or pulse stream that interacts with the concave end of the nanomotors to propel the nanomotors in a direction opposite the concave cavity.

Example B6 includes the method of example B5, in which the medium includes a plurality of cells in an in vitro container, and the method further including pre-concentrating the nanomotors and the cells into a localized pressure node region of the medium based on the application of the ultrasound energy, in which the pre-concentrated nanomotors penetrate the exterior of the cells to enter the intracellular region of the cells.

Example B7 includes the method of example B4, in which the nanowire body includes one or more of gold, platinum, nickel, silver, iron, or polyaniline (PANT) polymer.

Example B8 includes the method of example B4, in which the nanowire body includes a diameter in a range of 50 nm to 500 nm, and a length in a range of 500 nm to 10 µm.

Example B9 includes the method of example B1, in which the biologically active payload substance includes a nucleotide sequence configured to affect a gene expression of a target gene of the cell having a complementary nucleotide sequence.

Example B10 includes the method of example B9, in which the interaction of the biologically active payload substance with the target gene includes a silencing of the gene or an alteration of the gene.

Example B11 includes the method of example B9, in which the biologically active payload substance includes a small interfering ribonucleic acid (siRNA), and the functionalization layer includes a rolling circle amplification (RCA) nucleic acid strand that binds the siRNA.

Example B12 includes the method of example B11, in which the RCA nucleic acid strand is attached to a gold surface of the nanomotor via a gold-thiol interaction.

Example B13 includes the method of example B1, in which the biologically active payload substance includes a protein 9 (Cas9) nuclease complexed with a clustered regularly interspaced short palindromic repeats RNA (CRISPR RNA) and a trans-activating CRISPR RNA (tracrRNA) and fused in a single guided RNA (sgRNA) to cause a targeted gene alteration of a target gene of the cell.

Example B14 includes the method of example B13, in which the functionalization layer includes a disulfide linkage including cysteine functional groups that reversibly attach the Cas9-sgRNA complex to the nanomotor, and facilitate detachment of the Cas9-sgRNA in the intracellular region.

Example B15 includes the method of example B1, in which the biologically active payload substance includes a protein configured to affect a cellular function of the cell.

Example B16 includes the method of example B15, in which the biologically active payload substance includes a caspase-3 enzyme to trigger apoptosis of the cell.

Example B17 includes the method of example B16, in which the functionalization layer includes a biocompatible pH-responsive polymer coating on the nanomotor that encapsulates caspase-3 enzyme in an active conformation and prevents release of the caspase-3 enzyme in the medium, and that dissolves in a neutral or alkaline pH environment above 5.5 pH.

Example B18 includes the method of example B1, in which the nanomotors undergo a spinning motion inside the cell to accelerates the interaction at multiple locations within the intracellular region.

Example B19 includes the method of example B1, in which the propulsion of the nanomotors in the medium is based on a localized chemical reaction between substances of the nanomotor and the medium that creates a force to propel the nanomotor in the medium.

In some embodiments in accordance with the present technology (example B20), a nanomotor for intracellular payload delivery includes an asymmetric body having a concave cavity at one end of the nanowire body; a functionalization layer on an outer surface of the nanowire body; and a payload substance coupled to the nanomotor by the functionalization layer in a biologically active conformation, in which the payload substance is attached to a portion of the functionalization layer or at least partially encapsulated within the functionalization layer, in which the nanomotor is operable to propel in a biological medium and into an intracellular region of a living cell to initiate an interaction of the biologically active payload substance with an intracellular constituent of the living cell.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for intracellular delivery of a compound to a living cell, comprising:
providing a plurality of nanomotors operable to propel in a medium comprising a cell, wherein each nanomotor of the plurality of nanomotors includes a functionalization layer on an outer surface of the nanomotor coupling a payload substance in a biologically active conformation to the nanomotor; and
propelling the nanomotors in the medium to cause at least some of the nanomotors to penetrate into an intracellular region of the cell;
wherein the payload substance within the intracellular region of the cell initiates an interaction of the biologically active payload substance with an intracellular constituent of the cell, and
wherein the biologically active payload substance includes a protein 9 (Cas9) nuclease complexed with a clustered regularly interspaced short palindromic repeats RNA (CRISPR RNA) and a trans-activating CRISPR RNA (tracrRNA) and fused in a single guided RNA (sgRNA) to cause a targeted gene alteration of a target gene of the cell.

2. The method of claim 1, wherein the functionalization layer includes a disulfide linkage including cysteine functional groups that reversibly attach the Cas9-sgRNA complex to the nanomotor, and facilitate detachment of the Cas9-sgRNA in the intracellular region.

3. A method for intracellular delivery of a compound to a living cell, comprising:
providing a plurality of nanomotors operable to propel in a medium comprising a cell, wherein each nanomotor of the plurality of nanomotors includes a functionalization layer on an outer surface of the nanomotor coupling a payload substance in a biologically active conformation to the nanomotor; and
propelling the nanomotors in the medium to cause at least some of the nanomotors to penetrate into an intracellular region of the cell;
wherein the payload substance within the intracellular region of the cell initiates an interaction of the biologically active payload substance with an intracellular constituent of the cell, and
wherein the biologically active payload substance includes a protein configured to affect a cellular function of the cell.

4. The method of claim 3, wherein the biologically active payload substance includes a caspase-3 enzyme to trigger apoptosis of the cell.

5. The method of claim 4, wherein the functionalization layer includes a biocompatible pH-responsive polymer coating on the nanomotor that encapsulates caspase-3 enzyme in an active conformation and prevents release of the caspase-3 enzyme in the medium, and that dissolves in a neutral or alkaline pH environment above 5.5 pH.

6. A method for intracellular delivery of a compound to a living cell, comprising:
providing a plurality of nanomotors operable to propel in a medium comprising a cell, wherein each nanomotor of the plurality of nanomotors includes a functionalization layer on an outer surface of the nanomotor coupling a payload substance in a biologically active conformation to the nanomotor; and
propelling the nanomotors in the medium to cause at least some of the nanomotors to penetrate into an intracellular region of the cell;
wherein the payload substance within the intracellular region of the cell initiates an interaction of the biologically active payload substance with an intracellular constituent of the cell, and
wherein the biologically active payload substance includes a nucleotide sequence configured to affect a gene expression of a target gene of the cell having a complementary nucleotide sequence,
wherein the biologically active payload substance includes a small interfering ribonucleic acid (siRNA), and the functionalization layer includes a rolling circle amplification (RCA) nucleic acid strand that binds the siRNA.

7. The method of claim 6, wherein the RCA nucleic acid strand is attached to a gold surface of the nanomotor via a gold-thiol interaction.

* * * * *

UNITED STATES PATENT AND TRADEMARK OFFICE
CERTIFICATE OF CORRECTION

Page 1 of 2

PATENT NO.        : 11,007,281 B2
APPLICATION NO.   : 15/939104
DATED             : May 18, 2021
INVENTOR(S)       : Joseph Wang et al.

It is certified that error appears in the above-identified patent and that said Letters Patent is hereby corrected as shown below:

On the Title Page

In Item (73), under "Assignee", in Column 1, Line 2, delete "CALIFORNA" and insert -- CALIFORNIA --, therefor.

On Page 2, in Item (56), under "OTHER PUBLICATIONS", in Column 1, Line 1, delete "al,." and insert -- al., --, therefor at each occurrence throughout the patent.

On Page 2, in Item (56), under "OTHER PUBLICATIONS", in Column 2, Line 55, delete "toweard" and insert -- toward --, therefor.

On Page 3, in Item (56), under "OTHER PUBLICATIONS", in Column 1, Line 36, delete "Impriving" and insert -- Improving --, therefor.

On Page 3, in Item (56), under "OTHER PUBLICATIONS", in Column 2, Line 5, delete "Inititation" and insert -- Initiation --, therefor.

On Page 4, in Item (56), under "OTHER PUBLICATIONS", in Column 1, Line 9, delete "Poweed" and insert -- Powered --, therefor.

In the Specification

In Column 2, Line 46, delete "FIG." and insert -- FIGS. --, therefor.

In Column 2, Line 47, delete "an a" and insert -- a --, therefor.

In Column 3, Line 30, delete "casepase" and insert -- caspase --, therefor.

In Column 5, Lines 37-38, delete "to be delivered to delivered" and insert -- to be delivered --, therefor.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,007,281 B2

In Column 6, Line 59, delete "threat" and insert -- threaten --, therefor.

In Column 7, Line 45, delete "(PANT)" and insert -- (PANI) --, therefor.

In Column 9, Line 48, delete "treatment" and insert -- of treatment --, therefor.

In Column 12, Line 29, delete "an a" and insert -- a --, therefor.

In Column 15, Line 61, delete "nanomotor treatment." and insert -- of nanomotor treatment. --, therefor.

In Column 16, Line 22, delete "change" and insert -- chance --, therefor.

In Column 16, Line 66, delete "be" and insert -- to be --, therefor.

In Column 17, Line 35, delete "for during" and insert -- during --, therefor.

In Column 19, Line 63, delete "($CuSO^4.5H_2O$),") and insert -- ($CuSO_4.5H_2O$), --, therefor.

In Column 27, Line 48, delete "platting" and insert -- plating --, therefor.

In Column 27, Line 60, delete "nitic" and insert -- nitric --, therefor.

In Column 28, Line 63, delete "where" and insert -- were --, therefor.

In Column 32, Line 53, delete "FIG." and insert -- FIGS. --, therefor.

In Column 42, Line 22, delete "(PANT)" and insert -- (PANI) --, therefor.